US012612371B2

(12) United States Patent
Bourguignon et al.

(10) Patent No.: US 12,612,371 B2
(45) Date of Patent: Apr. 28, 2026

(54) SIGMA-1 RECEPTOR LIGANDS AND THERAPEUTIC USES THEREOF

(71) Applicants: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE DE MONTPELLIER, Montpellier (FR); ECOLE PRATIQUE DES HAUTES ETUDES, Paris (FR)

(72) Inventors: Jean-Jacques Bourguignon, Illkrich (FR); Martine Schmitt, Strasbourg (FR); Jacques Bricard, Illkirch-Graffenstaden (FR); Tangui Maurice, Saint Gely-du-Fesc (FR)

(73) Assignees: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE DE MONTPELLIER, Montpellier (FR); ECOLE PRATIQUE DES HAUTES ETUDES, Paris (FR)

( * ) Notice: Subject to any disclaimer, the term of this patent is extended or adjusted under 35 U.S.C. 154(b) by 732 days.

(21) Appl. No.: 17/785,941

(22) PCT Filed: Dec. 18, 2020

(86) PCT No.: PCT/EP2020/087032

§ 371 (c)(1),
(2) Date: Jun. 16, 2022

(87) PCT Pub. No.: WO2021/123174

PCT Pub. Date: Jun. 24, 2021

(65) Prior Publication Data

US 2023/0076057 A1 Mar. 9, 2023

(30) Foreign Application Priority Data

Dec. 19, 2019 (EP) .................................... 19306706

(51) Int. Cl.

| | |
|---|---|
| ***C07D 213/64*** | (2006.01) |
| ***A61K 31/4412*** | (2006.01) |
| ***A61K 31/505*** | (2006.01) |
| ***A61P 15/18*** | (2006.01) |
| ***A61P 25/16*** | (2006.01) |
| ***A61P 25/28*** | (2006.01) |
| ***C07D 237/14*** | (2006.01) |
| ***C07D 237/18*** | (2006.01) |
| ***C07D 237/26*** | (2006.01) |
| ***C07D 239/36*** | (2006.01) |
| ***C07D 241/18*** | (2006.01) |
| ***C07D 401/06*** | (2006.01) |
| ***C07D 401/10*** | (2006.01) |
| ***C07D 403/04*** | (2006.01) |
| ***C07D 403/06*** | (2006.01) |
| ***C07D 405/04*** | (2006.01) |
| ***C07D 405/06*** | (2006.01) |

(Continued)

(52) U.S. Cl.
CPC ......... *C07D 237/14* (2013.01); *C07D 237/18* (2013.01); *C07D 239/36* (2013.01); *C07D 241/18* (2013.01); *C07D 401/06* (2013.01); *C07D 401/10* (2013.01); *C07D 403/04* (2013.01); *C07D 405/12* (2013.01); *C07D 451/06* (2013.01)

(58) Field of Classification Search
CPC .. C07D 213/64; C07D 237/14; C07D 237/18; C07D 2379/26; C07D 241/18; C07D 401/06; C07D 403/04; C07D 403/06; C07D 405/04; C07D 405/06; C07D 237/26; A61K 31/4412; A61K 31/505; A61P 25/16; A61P 15/18; A61P 25/28
See application file for complete search history.

(56) References Cited

U.S. PATENT DOCUMENTS 4,826,845 A * 5/1989 Kasztreiner .......... C07D 249/08 544/239
2023/0049619 A1 2/2023 Bourguignon et al.

FOREIGN PATENT DOCUMENTS

EP 1 057 820 12/2000
EP 1 336 602 8/2003

(Continued)

OTHER PUBLICATIONS

Yamada et al. (Journal of Medicinal Chemistry (1983), 26(3), 373-81). Abstract.*

(Continued)

*Primary Examiner* — Bruck Kifle
(74) *Attorney, Agent, or Firm* — SALIWANCHIK, LLOYD & EISENSCHENK

(57) ABSTRACT

The present invention relates to the field of medicine. More specifically, the present invention relates to compounds that are sigma-1 receptor agonists and their use for the treatment of central nervous system disorders, including cognitive or neurodegenerative disorders, such as Alzheimer's disease, Parkinson's disease, Huntington's disease, Amyotrophic lateral sclerosis, and multiple sclerosis.

14 Claims, No Drawings

(51) Int. Cl.
*C07D 405/12* (2006.01)
*C07D 451/06* (2006.01)

(56) References Cited

FOREIGN PATENT DOCUMENTS

| | | |
|---|---|---|
| EP | 1 947 086 | 7/2008 |
| WO | WO 2009/050183 | 4/2009 |
| WO | WO 2012/006419 | 1/2012 |
| WO | WO 2014/100716 | 6/2014 |
| WO | WO 2016/191658 | 12/2016 |
| WO | WO 2019/068771 | 4/2019 |
| WO | WO 2021/123145 | 6/2021 |

OTHER PUBLICATIONS

Wermuth (Agressologie (1965), 6(4), 383-98). Abstract.*

Biancalani, C. et al. "Further Studies on Arylpiperazinyl Alkyl Pyridazinones: Discovery of an Exceptionally Potent, Orally Active, Antinociceptive Agent in Thermally Induced Pain" *Journal of Medicinal Chemistry* 2009, pp. 7397-7409, vol. 52, No. 23.

Fernandez, C. et al. "Reactions of 1,ω-bis(2-bronopyridinium)alkanes with hydroxide ion in aqueous solutions" *Journal of Physical Organic Chemistry*, 1998, pp. 25-30, vol. 11. No. 1.

Intagliata, S. et al. "New N- and O-arylpiperazinylalkyl pyrimidines and 2-methylquinazolines derivatives as 5-$HT_7$ and 5-$HT_{1A}$ receptor ligands: Synthesis, structure-activity relationships, and molecular modeling studies" *Bioorganic & Medicinal Chemistry*, 2017, pp. 1250-1259, vol. 25, No. 3.

Matyus, P. et al. "Synthesis, antihypertensive and α-adrenoceptor activity of novel 2-aminoalkyl-3(2H)-pyridazinones" *Eur J Med Chem*, 1992, pp. 107-114, vol. 27, No. 2.

Spulak, M. et al. "Novel bronchodilatory quinazolines and quinoxalines: Synthesis and biological evaluation" *European Journal of Medicinal Chemistry*, 2014, pp. 65-72, vol. 74.

Wu, W. et al. "Copper-catalyzed interrupted click reaction: The synthesis of 3-difluoromethyl-substituted 1,2,4-triazinones" *Journal of Fluorine Chemistry*, 2019, pp. 1-5, vol. 226.

Written Opinion in International Application No. PCT/EP2020/087032, Apr. 7, 2021, pp. 1-12.

* cited by examiner

SIGMA-1 RECEPTOR LIGANDS AND THERAPEUTIC USES THEREOF

CROSS-REFERENCE TO RELATED APPLICATION

This application is the U.S. national stage application of International Patent Application No. PCT/EP2020/087032, filed Dec. 18, 2020.

FIELD OF THE INVENTION

The present invention relates to the field of medicine. More specifically, the present invention relates to compounds that are sigma-1 receptor agonists and their use for the treatment of central nervous system disorders, including cognitive or neurodegenerative disorders, such as Alzheimer's disease, Parkinson's disease, Huntington's disease, Amyotrophic lateral sclerosis, and multiple sclerosis.

BACKGROUND OF THE INVENTION

Two sigma receptor subtypes have been identified based on their pharmacological profile. The sigma-1 receptor is a membrane-associated protein, found throughout the body and widely expressed in the central nervous system, neurons, astrocytes, oligodendrocytes and microglia.

The sigma-1 receptor is a membrane-associated protein, found throughout the body and widely expressed in the central nervous system, neurons, astrocytes, oligodendrocytes and microglia. The sigma-1 receptor is a single polypeptide transmembrane protein comprising 223 amino acids. As a single 25 kD polypeptide and chaperone protein, it is highly expressed at the mitochondria-associated endoplasmic reticulum (ER) membranes and plasma membranes. Among its identified partner proteins are the glucose-related protein 78/binding immunoglobulin protein (BiP) and the inositol-1,4,5 trisphosphate (IP3) receptor. The sigma-1 receptor is a ligand-operated chaperone protein, that binds and is activated/inactivated by diverse classes of pharmacological compounds, including for instance the dextrogyre isomers of benzomorphans, such as (+)-pentazocine and (+)-SKF-10,047. Although certain endogenous ligands have been identified interacting with the sigma-1 receptor, such as neuro (active) steroids, neuropeptides, choline or trace amines, the existence of a high-affinity endogenous sigma-1 receptor ligand is still unclear. Activation of the sigma-1 receptor by agonist has several cellular consequences but mainly results in an amplification of calcium exchanges between the ER and mitochondria, by interacting with the IP3 receptor on ER membranes, and in the induction of ER stress pathways, by interacting with ER stress sensors such as BiP or IRE-1.

Sigma-1 receptor agonists have been reported as having antidepressant effects in several animal models. For example, the selective mi receptor agonists (+)-pentazocine, (+)-SKF-10,047, igmesine, OPC14523, DTG or SA4503 reduce freezing in the conditioned fear stress test or immobility time in the forced swim test or are active in the tail suspension test (Matsuno et al., Eur J Pharmacol 312:267-71, 1996; Tottori et al. Neuropharmacology 2001 41:976-88; Urani et al., J Pharmacol Exp Ther 298:1269-79, 2001).

It has also been reported to play a role in cell survival (Wang et al., Exp Cell Res 312:1439-46, 2006; Hayashi & Su, Cell 131:596-610, 2007; Jiang et al., Invest Ophthalmol Vis Sci 47:5576-82, 2006). Sigma-1 receptor ligands have been reported to be neuroprotective. The sigma-1 receptor ligand opipramol was reported as protected against ischemia in gerbils. In addition, other sigma ligands, including BMY-14802, caramiphen and haloperidol, exhibited properties in in vivo models that are consistent with protective effects (Pontecorvo et al., Brain Res Bull 26:461-5, 1991). Several sigma ligands were reported to inhibit ischemia-induced glutamate release from hippocampal slice preparations in vitro (Lobner et al., Neurosci Lett 1 17:169-74, 1990). It has also been reported that the sigma-1 receptor agonist (+)-pentazocine can protect the retinal cells against stress (Dun et al., Invest Ophthalmol Vis Sci 48:4785-94, 2007; Smith et al., Invest Ophthalmol Vis Sci 49:4154-61, 2008).

Particular note is made of the utility of a sigma-1 receptor agonist with low sigma-2 receptor affinity in treating ischemic brain/neuronal injury such as from focal ischemia. Sigma-1 receptor agonists are also believed useful in improving cognitive impairment such as exhibited with impaired neurotransmitter function (e.g., acetylcholine) as well as age associated cognitive impairment, and anxiety associated impairment (including pregnancy stress resulting in learning deficits of offspring).

Agonists of the sigma-1 receptor are effective anti-amnesic compounds. This has been demonstrated in a number of pharmacological and pathological models of learning and memory impairment in rodents. In particular, sigma-1 receptor agonists are routinely validated in vivo against scopolamine-induced learning deficits, a model of muscarinic acetylcholine receptor (mAChR) blockade. For instance, the sigma-1 receptor agonists LS-1-137 (Malik et al., Br J Pharmacol 172:2519-31, 2015), the sigma-1 positive modulators E1R (Zvejniece et al., Br J Pharmacol 171:761-71, 2014) or OZP002 (Maurice et al., Pharmacol Res 144:315-30, 2019) or the mixed mAChR/mi agonists ANAVEX1-41 or ANAVEX2-73 (blarcamesine), two diphenyl-3-furan-methanamine derivatives (Espallergues et al., Br J Pharmacol 152:267-79, 2017; Villard et al. Neuropsychopharmacology 34:1552-66, 2009), have recently been characterized as anti-amnesic drugs against scopolamine-induced learning impairments. The efficacy of sigma-1 receptor agonists as symptomatic drugs in cognition has been described not only in cholinergic amnesia models (e.g., scopolamine, mecamylamine, p-chloroamphetamine, forebrain lesions) but also in glutamatergic models of learning deficit. Learning impairment induced by the non-competitive NMDA receptor antagonist dizocilpine (MK-081) has been used to demonstrate that the positive modulation exerted by the sigma-1 receptor on NMDA neurotransmission, suggested in vitro or in vivo using extracellular recordings of the NMDA-induced firing of pyramidal neurons in the CA3 hippocampal area has behavioral consequences. The efficacy of sigma-1 receptor agonists in alleviating dizocilpine-induced learning impairment also points to the potential utility of these drugs in treating schizophrenia-related cognitive deficits, in particular since hypoglutamatergy models have been considered as highly pertinent for mimicking the negative symptoms of schizophrenia (Meltzer et al., Int J Neuropsychopharmacol 16:2181-94, 2013). Interestingly, sigma-1 receptor ligands tested in both the scopolamine and dizocilpine models showed a similar active dose-range in vivo. Activation of the sigma-1 receptor therefore appeared to similarly modulate the activity of the two neurotransmission systems involved in memory processes in the limbic and cortical structures, namely cholinergic and particularly glutamatergic systems. The sigma-1 receptor agonists enhance NMDA-induced firing in the hippocampus at very low doses. (+)-SKF-10,047 (also known as Alazocine), PRE084, and (+)-pentazocine increased the expression of the NR2A and NR2B subunits of NMDA receptor, as well as PSD95 (also known as SAP-90), in the rat hippocampus. The sigma-1 receptor agonist treatment leads to increased interaction between NR2 subunits and sigma-1 receptors and promotes trafficking of NMDA receptors to the cell surface. The sigma-1 receptor interacts with NMDA receptors through the regulation of a small conductance $Ca^{2+}$-activated $K^+$ current (SK channels). At the behavioral level, young male sigma-1 KO mice, at 2 months of age, showed signs of anxiety in procedures including the open-field, passive avoidance and elevated plus-maze, and an enhanced response to stress in the forced swim test. In male animals, the mi receptor ablation therefore increased stress and anxiety responses but memory responses were unchanged. However, female sigma-1 KO mice showed memory alterations in spontaneous alternation and water-maze learning paradigms, and this phenotype increased with age. Of note, both 2- and 14-month old female sigma-I KO mice showed decreased plasma levels of 17β-estradiol and a supplementation treatment with the hormone reversed the memory deficits in young and aged mice (Chevallier et al., J Psychopharmacol 25:960-75, 2011). This suggested that sigma-1 receptor ablation has a developmental impact on the steroidal tonus.

The sigma-1 receptor agonists are therefore promising symptomatic drugs in rodent models of cognitive alterations related to pathological ageing and neurodegenerative diseases. First, igmesine and PRE-084, in the low mg/kg dose-range, improved learning ability in the senescence-accelerated mouse SAMP/8 (Maurice et al. Brain Res 733: 219-30, 1996). Second, these compounds also alleviated the memory deficits induced by amyloid toxicity in pharmacological models of Alzheimer's disease (AD). (+)-pentazocine, PRE-084, cutamesine, dimemorphan, ANAVEX1-41, blarcamesine, OZP002 and the sigma-1 receptor binding neuroactive steroids attenuated the learning deficits in mice that received a direct intracerebroventricular injection of oligomerized A025-35 peptide, which produces neurotoxicity closely related to AD pathology (Meunier et al., Br J Pharmacol. 149: 998-1012, 2006; Villard et al., J Psychopharmacol 25: 1101-17, 2011; Maurice et al., Pharmacol Res 144:315-30, 2019). All sigma-1 receptor agonists or positive modulators alleviated the A025-35-induced learning impairments in spatial or nonspatial tasks involving short-term as well as long-term memory. These effects were blocked by BD1047, haloperidol, BMY-14,802, and progesterone, all putative sigma-1 receptor antagonists. Of note, whereas they blocked sigma-1 receptor agonist effects, the antagonists alone did not alter behavior (positively or negatively) in these models. The sigma-1 receptor agonists are thus promising agents to treat AD symptoms, with active doses similar to or lower than the reference drugs donepezil, rivastigmine, galantamine, and memantine (Meunier et al., Br J Pharmacol 149: 998-1012, 2006).

Finally, blarcamesine, which is a mixed muscarinic and sigma-1 drug, has successfully completed a phase 2 clinical trial in AD. The drug stabilized ADAS-ADL scores and limited MMSE score decrease in patients after a 3-year treatment in patients showing the highest drug bioavailability (Hample et al., CTAD Abstracts, 2018).

Thus, there is nowadays a strong need for the development of new sigma-1 receptor agonists for the treatment of cognitive disorders related to psychiatric pathologies, neurodegenerative diseases, such as Alzheimer, Huntington and Parkinson diseases, amyotrophic lateral sclerosis (ALS) or multiple sclerosis, and genetic diseases associated with MAM (Mitochondria Associated Membranes) dysfunctions.

The present invention seeks to meet this and other needs. Compounds according to the invention have been found to have affinity for sigma-1 receptors.

SUMMARY OF THE INVENTION

In this respect, the present invention relates to a compound having the following formula (I):

(I)

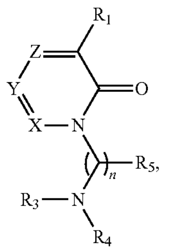

wherein:

$R_1$ represents:
- H;
- an aryl($C_1$-$C_6$)alkyl group;
- an aryl($C_2$-$C_6$)alkenyl group;
- an aryl group;
- a heteroaryl group;
- a heterocycloalkyl group;
- a cycloalkyl group; or
- a -QR group, with Q being O or S, and R being alkyl, aryl or aralkyl;
  - said group being optionally substituted by at least one —OH, halogen, ($C_1$-$C_6$)alkyl optionally substituted by one or more fluorine atoms, or ($C_1$-$C_6$) alkyloxy;

Z represents N or $CR_2$;

$R_2$ represents H, a ($C_1$-$C_4$)alkyl or a phenyl group;

X and Y are either $CR_6$ and N, or N and $CR_6$, or $CR_6$ and CH, respectively;

$R_6$ is H or a ($C_1$-$C_4$)alkyl group;

n is 3, 4, 5, or 6;

$R_3$ and $R_4$:
- represent independently a radical selected from a hydrogen atom, a ($C_1$-$C_6$)alkyl, ($C_2$-$C_6$)alkenyl, cycloalkyl, heterocycloalkyl, aryl, heteroaryl, and aryl($C_1$-$C_6$)alkyl, said radical being optionally substituted by at least one substituent selected from the group consisting of a hydroxy, a ($C_1$-$C_6$)alkyl, a ($C_1$-$C_6$)alcoxy, a cycloalkyl, a heterocycloalkyl, an aryl, and a heteroaryl; or
- form, together with the nitrogen to which they are bound, a nitrogen-based heterocycloalkyl, said nitrogen-based heterocycloalkyl being optionally substituted by at least one substituent selected from the group consisting of a hydroxy, oxo, ($C_1$-$C_6$)alkyl, ($C_2$-$C_6$)alkenyl, cycloalkyl, aryl, heteroaryl, heterocycloalkyl, aryl($C_1$-$C_6$)alkyl, and hydroxy($C_1$-$C_6$) alkyl, and said nitrogen-based heterocycloalkyl being optionally fused with at least one 5-14 membered ring selected from aryl and heteroaryl;

each of $R_5$ represents independently H, OH, or a ($C_1$-$C_4$) alkyl group;

an isomer, a solvate or any pharmaceutical salt thereof.

It also relates to a compound as defined above for use as a medicine.

It further relates to a pharmaceutical composition comprising a compound as defined above, and a pharmaceutically acceptable support.

Another object of the invention is a compound or pharmaceutical composition as defined above, for use in the treatment of disorder modulated by sigma-1 receptor, including cognitive or neurodegenerative disorders. In a particular embodiment, said disorder is selected from the group consisting of (1) neurodegenerative diseases such as Alzheimer disease, Parkinson's disease, Huntington's disease, Amyotrophic lateral sclerosis, multiple sclerosis; (2) cognitive and memory alterations such as pathological ageing, ischemic amnesia, schizophrenia-related cognitive deficits and depression; (3) developmental cognitive disorders such as autism-related disorders and mental retardation-related disorders; and (4) genetic diseases associated with MAM dysfunctions.

DETAILED DESCRIPTION

Definitions

According to the present invention, the terms below have the following meanings:

The terms mentioned herein with prefixes such as for example $C_1$-$C_3$, $C_1$-$C_6$ or $C_2$-$C_6$ can also be used with lower numbers of carbon atoms such as $C_1$-$C_2$, $C_1$-$C_5$, or $C_2$-$C_5$. If, for example, the term $C_1$-$C_3$ is used, it means that the corresponding hydrocarbon chain may comprise from 1 to 3 carbon atoms, especially 1, 2 or 3 carbon atoms. If, for example, the term $C_1$-$C_6$ is used, it means that the corresponding hydrocarbon chain may comprise from 1 to 6 carbon atoms, especially 1, 2, 3, 4, 5 or 6 carbon atoms. If, for example, the term $C_2$-$C_6$ is used, it means that the corresponding hydrocarbon chain may comprise from 2 to 6 carbon atoms, especially 2, 3, 4, 5 or 6 carbon atoms.

The term "alkyl" refers to a saturated, linear or branched aliphatic group. Preferably, the alkyl group has 1 to 6 carbon atoms. The term "($C_1$-$C_3$)alkyl" more specifically means methyl, ethyl, propyl, or isopropyl. The term "($C_1$-$C_6$)alkyl" more specifically means methyl, ethyl, propyl, isopropyl, butyl, isobutyl, tert-butyl, pentyl or hexyl. In a preferred embodiment, the "alkyl" is a methyl, an ethyl, or a propyl, more preferably a methyl or an ethyl. The alkyl group includes halogenated alkyl group, such as perhalogenated alkyl (e.g. $—CF_3$).

The term "alkenyl" refers to an unsaturated, linear or branched aliphatic group comprising at least one carbon-carbon double bound. The term "($C_2$-$C_6$)alkenyl" more specifically means ethenyl, propenyl, isopropenyl, butenyl, isobutenyl, pentenyl, prenyl or hexenyl. In a preferred embodiment, the "alkenyl" is an ethenyl.

The term "alkoxy" or "alkyloxy" corresponds to the alkyl group as above defined bonded to the molecule by an —O-(ether) bond. ($C_1$-$C_3$)alkoxy includes methoxy, ethoxy, propyloxy, and isopropyloxy. ($C_1$-$C_6$)alkoxy includes methoxy, ethoxy, propyloxy, isopropyloxy, butyloxy, isobutyloxy, tert-butyloxy, pentyloxy and hexyloxy. In a preferred embodiment, the "alkoxy" or "alkyloxy" is a methoxy.

The term "cycloalkyl" corresponds to a saturated or unsaturated ("unsaturated" refers preferably to "at least one double carbon-carbon bond") mono-, bi- or tri-cyclic alkyl group having between 3 and 20 atoms of carbons (also named ($C_3$-$C_{20}$)cycloalkyl). It also includes fused, bridged, or spiro-connected cycloalkyl groups. The term "cycloalkyl" includes for instance cyclopropyl, cyclobutyl, cyclopentyl, cyclohexyl, and cyclohexenyl. The term "cycloalkyl" may also refer to a 5-10 membered bridged carbocyclyl such as bicyclo[2,2,1]heptanyl, bicyclo[2,2,2]octanyl, or adamantyl. In a preferred embodiment, the "cycloalkyl" is a cyclohexyl, cyclohexenyl or an adamantanyl.

The term "heterocycloalkyl" corresponds to a saturated or unsaturated (preferably at least one double carbon-carbon bond) cycloalkyl group as above defined further comprising at least one heteroatom or heteroatomic group such as nitrogen, oxygen, or sulphur atom. It also includes fused, bridged, or spiro-connected heterocycloalkyl groups. Representative heterocycloalkyl groups include, but are not limited to 3-dioxolane, benzo [1,3] dioxolyl, pyranyl, tetrahydropyranyl, thiomorpholinyl, pyrazolidinyl, piperidyl, piperazinyl, azepanyl, 1,4-dioxanyl, imidazolinyl, pyrrolinyl, pyrrolidinyl, piperidinyl, imidazolidinyl, morpholinyl, 1,4-dithianyl, pyrrolidinyl, quinolizinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydro-2H-pyranyl, tetrahydrofuranyl, and tetrahydrothiophenyl. The term "heterocycloalkyl" may also refer to a 5-10 membered bridged heterocyclyl such as 7-oxabicyclo[2,2,1]heptanyl. In a preferred embodiment, the heterocycloalkyl is morpholinyl, piperidinyl, piperazinyl, oxazepanyl, azepanyl, azocanyl, nortropanyl, decahydroquinolinyl, thiomorpholinyl, or 6-azabicyclo[3.2.1]octanyl.

The term "aryl" corresponds to a mono- or bi-cyclic aromatic hydrocarbons having from 6 to 14 carbon atoms (also named ($C_6$-$C_{14}$)aryl). For instance, the term "aryl" includes phenyl, or naphthyl. In a preferred embodiment, the aryl is a phenyl.

The term "heteroaryl" as used herein corresponds to an aromatic, mono- or poly-cyclic group comprising between 5 and 14 atoms and comprising one or more heteroatoms, such as nitrogen (N), oxygen (O) or sulphur (S) atom, or heteroatomic groups. Examples of such mono- and poly-cyclic heteroaryl group may be: pyridinyl, thiazolyl, thiophenyl, furanyl, pyrrolyl, imidazolyl, triazolyl, tetrazolyl, benzofuranyl, thianaphthalenyl, indolyl, indolinyl, quinolinyl, isoquinolinyl, benzimidazolyl, triazinyl, thianthrenyl, isobenzofuranyl, phenoxanthinyl, isothiazolyl, isoxazolyl, pyrazinyl, pyridazinyl, indolizinyl, isoindolyl, indazolyl, purinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, benzotriazolyl, benzoxazolyl, benzisoxazolyl, oxindolyl, benzothienyl, benzothiazolyl, s-triazinyl, oxazolyl, or thiofuranyl. In a preferred embodiment, the heteroaryl is furanyl, benzofuranyl, pyridyl, pyrrolyl or thiophenyl.

The term "nitrogen-based heterocycloalkyl" (also named "nitrogen-containing heterocycloalkyl") refers to a heterocycloalkyl as defined above, containing at least one nitrogen atom. The nitrogen-based heterocycloalkyl may further comprise other heteroatoms, such as O or S. Examples of nitrogen-based heterocycloalkyl include, but are not limited to, piperidinyl, pyrrolidinyl, morpholinyl, azepanyl, pyrrolyl, or imidazolyl, preferably piperidinyl.

The term "nitrogen-based heteroaryl" (also named "nitrogen-containing heteroaryl") refers to a heteroaryl as defined above, containing at least one nitrogen atom. The nitrogen-based heteroaryl may further comprise other heteroatoms, such as O or S. Examples of nitrogen-based heteroaryl are imidazolyl, pyrrolyl, and pyrazolyl.

The term "arylalkyl" or "aralkyl" as used herein corresponds to an alkyl as defined above, substituted by at least one aryl group as defined above. More specifically, "aryl $(C_1-C_6)$alkyl" refers to a $(C_1-C_6)$alkyl as defined above, substituted by at least one aryl group as defined above. Examples of arylalkyl may be benzyl or phenylethyl (also named, phenethyl).

The term "arylalkenyl" as used herein corresponds to an alkenyl as defined above, substituted by at least one aryl group as defined above. More specifically, "aryl$(C_2-C_6)$ alkenyl" refers to a $(C_2-C_6)$alkenyl as defined above, substituted by at least one aryl group as defined above. An example of aryl$(C_2-C_6)$alkenyl is phenylethenyl (also named "phenethenyl").

The term "alkylcycloalkyl" as used herein corresponds to a cycloalkyl as defined above, substituted by at least one alkyl group as defined above. More specifically, "$(C_1-C_6)$ alkylcycloalkyl" refers to a cycloalkyl as defined above, substituted by at least one $(C_1-C_6)$alkyl group as defined above.

The term "alkylheterocycloalkyl" as used herein corresponds to a heterocycloalkyl as defined above, substituted by at least one alkyl group as defined above. More specifically, "$(C_1-C_6)$alkylheterocycloalkyl" refers to a heterocycloalkyl as defined above, substituted by at least one $(C_1-C_6)$alkyl group as defined above.

The term "alkylaryl" as used herein corresponds to an aryl as defined above, substituted by at least one alkyl group as defined above. More specifically, "$(C_1-C_6)$alkylaryl" refers to an aryl as defined above, substituted by at least one $(C_1-C_6)$alkyl group as defined above.

The term "alkylheteroaryl" as used herein corresponds to a heteroaryl as defined above, substituted by at least one alkyl group as defined above. More specifically, "$(C_1-C_6)$ alkylheteroaryl" refers to a heteroaryl as defined above, substituted by at least one $(C_1-C_6)$alkyl group as defined above.

The term "halogen" corresponds to a fluorine, chlorine, bromine, or iodine atom, preferably a fluorine, chlorine or bromine, and more preferably a chlorine or a fluorine.

The expression "substituted by at least" means that the radical is substituted by one or several groups of the list.

It is understood that the substitution by two or more substituents on a hydrocarbon chain, such as an alkyl or cycloalkyl chain, may occur on the same carbon and/or on different carbons. For instance, the structures of an ethyl chain substituted by two given radicals "A" and "B", include, but is not limited to, structures of formulae (Va) or (Vb):

(Va)

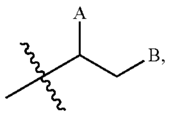

(Vb)

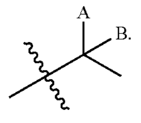

Unless specified otherwise, the alkyl, alkenyl, cycloalkyl, heterocycloalkyl, aryl, and heteroaryl groups as defined above may be unsubstituted or substituted by at least one substituent, said at least one substituent being selected from the group consisting of halogen, preferably fluorine and chlorine, CN, $NO_2$, $SO_3H$, alkyl, cycloalkyl, heterocycloalkyl, aryl, heteroaryl, —C(O)R, —$C(O)_2R$, —OH, —OR, —CHOHR, —C(O)NRR', —CONHOR, —$CONHSO_2R$, —NRR', —N(R)C(O)R', —N(R)NR'R", —$N(R)C(O)_2R'$, —N(R)C(O)NR'R", —$N(R)S(O)_2R'$, —SR, —S(O)R, —$S(O_2)R$, —S(O)NRR', —$S(O)_2NRR'$; R, R', and R" being independently H, $(C_1-C_6)$alkyl, cycloalkyl, aryl, heterocycloalkyl, heteroaryl, $(C_1-C_6)$alkylcycloalkyl, $(C_1-C_6)$alkylaryl, $(C_1-C_6)$alkylheterocycloalkyl), or $(C_1-C_6)$alkylheteroaryl.

As used herein, the terms "treatment", "treat" or "treating" refer to any act intended to ameliorate the health status of patients such as therapy, prevention, prophylaxis and retardation of a disease. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, even more preferably to a human, including adult, child, newborn and human at the prenatal stage. However, the term "subject" can also refer to non-human animals, in particular mammals such as dogs, cats, horses, cows, pigs, sheep and non-human primates, among others.

The terms "quantity," "amount," and "dose" are used interchangeably herein and may refer to an absolute quantification of a molecule.

As used herein, the terms "active principle", "active ingredient" and "active pharmaceutical ingredient" are equivalent and refer to a component of a pharmaceutical composition having a therapeutic effect.

As used herein, the term "therapeutic effect" refers to an effect induced by an active ingredient, or a pharmaceutical composition according to the invention, capable to prevent or to delay the appearance of a disease, such as a neurodegenerative or cognitive disease, or to cure or attenuate the effects of a disease.

As used herein, the term "effective amount" refers to a quantity of an active ingredient or of a pharmaceutical composition which prevents, removes or reduces the deleterious effects of the disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the active ingredients.

Compounds

It is the purpose of the present invention to provide compounds, or pharmaceutically acceptable salts thereof, especially for use in the treatment of disorder modulated by $\sigma_1$ receptor (such as cognitive or neurodegenerative disorders), said compounds having the formula (I) as shown below,

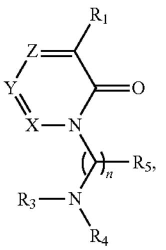

(I)

wherein:

$R_1$ represents:

H;

an aryl($C_1$-$C_6$)alkyl group;

an aryl($C_2$-$C_6$)alkenyl group;

an aryl group;

a heteroaryl group;

a heterocycloalkyl group;

a cycloalkyl group; or a -QR group, with Q being O or S, and R being alkyl, aryl or aralkyl;

said group being optionally substituted by at least one —OH, halogen, ($C_1$-$C_6$)alkyl optionally substituted by one or more fluorine atoms, or ($C_1$-$C_6$) alkyloxy;

Z represents N or $CR_2$;

$R_2$ represents H, a ($C_1$-$C_4$)alkyl or a phenyl group;

X and Y are either $CR_6$ and N, or N and $CR_6$, or $CR_6$ and CH, respectively;

$R_6$ is H or a ($C_1$-$C_4$)alkyl group;

n is 3, 4, 5, or 6;

$R_3$ and $R_4$:

represent independently a radical selected from a hydrogen atom, a ($C_1$-$C_6$)alkyl, ($C_2$-$C_6$)alkenyl, cycloalkyl, heterocycloalkyl, aryl, heteroaryl, and aryl($C_1$-$C_6$)alkyl, said radical being optionally substituted by at least one substituent selected from the group consisting of a hydroxy, a ($C_1$-$C_6$)alkyl, a ($C_1$-$C_6$)alcoxy, a cycloalkyl, a heterocycloalkyl, an aryl, and a heteroaryl; or form, together with the nitrogen to which they are bound, a nitrogen-based heterocycloalkyl, said nitrogen-based heterocycloalkyl being optionally substituted by at least one substituent selected from the group consisting of a hydroxy, oxo, ($C_1$-$C_6$)alkyl, ($C_2$-$C_6$)alkenyl, cycloalkyl, aryl, heteroaryl, heterocycloalkyl, aryl($C_1$-$C_6$)alkyl, and hydroxy($C_1$-$C_6$) alkyl, and said nitrogen-based heterocycloalkyl being optionally fused with at least one 5-14 membered ring selected from aryl and heteroaryl;

each of $R_5$ represents independently H, OH, or a ($C_1$-$C_4$) alkyl group;

an isomer, a solvate or any pharmaceutical salt thereof.

In a particular embodiment, a compound of the invention is of formula (I) wherein $R_1$ represents:

an aryl group, such as a phenyl optionally substituted by at least one —OH, halogen, ($C_1$-$C_6$)alkyl optionally substituted by one or more fluorine atoms, or ($C_1$-$C_6$) alkyloxy;

a heteroaryl, such as thiophenyl, furanyl, benzofuranyl, pyridyl, or pyrrolyl;

a heterocycloalkyl, such as piperidinyl; or a group selected from cyclohexenyl, phenethyl, phenethenyl, —OPh, and —SPh.

Preferably, $R_1$ represents a phenyl optionally substituted by at least one —OH, halogen (such as fluorine or chlorine), ($C_1$-$C_6$)alkyl optionally substituted by one or more fluorine atoms (such as —$CF_3$), or ($C_1$-$C_6$)alkyloxy (such as methoxy). According to a particular embodiment, $R_1$ represents a phenyl optionally substituted by at least one chlorine.

In a particular embodiment where $R_1$ is a heterocycloalkyl, it is preferred that $R_1$ is a nitrogen-based heterocycloalkyl.

In a particular embodiment where $R_1$ is a heteroaryl, it is preferred that $R_1$ is a nitrogen-based heteroaryl.

According to a particular embodiment, when $R_1$ represents a nitrogen-based heterocycloalkyl or heteroaryl group, said group is preferably attached to the rest of the molecule by a nitrogen atom of said nitrogen-based heterocycloalkyl or heteroaryl.

In a particular embodiment, $R_2$ is H or ($C_1$-$C_4$)alkyl. In a more particular embodiment, $R_2$ is H, methyl or a phenyl group. Preferably, $R_2$ is H or a methyl, more preferably $R_2$ is H.

In a particular embodiment, a compound of the invention is of formula (I) wherein Z is $CR_2$.

Preferably, Z is $CR_2$ and $R_2$ represents H.

X and Y in formula (I) may be either $CR_6$ and N, or N and $CR_6$, or $CR_6$ and CH, respectively, with $R_6$ being H or a ($C_1$-$C_4$)alkyl group.

Preferably, $R_6$ is H or a methyl, and more preferably $R_6$ is H.

In a particular embodiment, a compound of the invention is of formula (I) wherein X and Y are N and $CR_6$, respectively ($R_6$ being preferably H or methyl).

In another particular embodiment, a compound of the invention is of formula (I) wherein X and Y are $CR_6$ and CH, respectively ($R_6$ being preferably H).

In a preferred embodiment, a compound of the invention is of formula (I) wherein X and Y are N and $CR_6$, respectively, and more preferably N and CH respectively.

In a particular embodiment, a compound of the invention is of formula (I) wherein n is 4, 5 or 6. In another particular embodiment, n is 3, 4 or 5. Preferably, n is 4.

In a compound of formula (I) according to the invention, each of $R_5$ represents independently H, OH, or a ($C_1$-$C_4$) alkyl group. Preferably, each of $R_5$ represents independently H, OH, or methyl, more preferably H or OH, and even more preferably H.

It is understood that when n is 3, 4, 5, or 6, then 3, 4, 5, or 6 $R_5$'s are present respectively, and each of $R_5$ is as defined above. For instance, when n is 4, a compound of formula (I) is represented as follows:

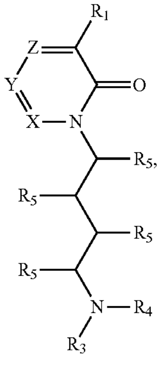

wherein X, Y, Z, $R_1$, $R_3$, $R_4$ are as defined above, and each of $R_5$ represents independently H, OH, or a $(C_1-C_4)$alkyl group (preferably, H, OH, or methyl, more preferably H or OH, and even more preferably H).

In a particular embodiment, a compound of the invention is of formula (I) wherein one of $R_5$ is H, OH or a $(C_1-C_4)$ alkyl group (such as a methyl), and the other ones of $R_5$ are H.

Preferably, each of $R_5$ is H.

In a particular embodiment, a compound of the invention is of formula (I) wherein $R_3$ and $R_4$:

represent independently a radical selected from:
- a hydrogen atom,
- a $(C_1-C_6)$alkyl, preferably a methyl or an ethyl,
- a cycloalkyl, preferably a cyclohexyl or an adamantanyl, and
- an aryl$(C_1-C_6)$alkyl, preferably a benzyl, said radical being optionally substituted by one or two substituents independently selected from the group consisting of:
- a hydroxy,
- a $(C_1-C_6)$alcoxy, preferably a methoxy,
- a heterocycloalkyl, preferably a tetrahydrofuranyl or a tetrahydropyranyl; and
- an aryl, preferably a phenyl; or form together with the nitrogen to which they are bound a nitrogen-based heterocycloalkyl, preferably a morpholinyl, piperidinyl, piperazinyl, oxazepanyl, azepanyl, azocanyl, nortropanyl, decahydroquinolinyl, thiomorpholinyl, or 6-azabicyclo[3.2.1]octanyl, said nitrogen-based heterocycloalkyl being optionally substituted by at most three substituents independently selected from the group consisting of
- hydroxy, oxo,
- $(C_1-C_6)$alkyl, preferably a methyl,
- aryl, preferably a phenyl,
- aryl$(C_1-C_6)$alkyl, preferably a benzyl,
- hydroxy$(C_1-C_6)$alkyl, preferably hydroxymethyl or hydroxyethyl, and said nitrogen-based heterocycloalkyl being optionally fused with one aryl group, preferably a phenyl.

In a more particular embodiment, $R_3$ and $R_4$ form together with the nitrogen to which they are bound a nitrogen-based heterocycloalkyl, preferably a morpholinyl, piperidinyl, piperazinyl, oxazepanyl, azepanyl, azocanyl, nortropanyl, decahydroquinolinyl, thiomorpholinyl, or 6-azabicyclo[3.2.1]octanyl, said nitrogen-based heterocycloalkyl being optionally substituted by at most three substituents independently selected from the group consisting of
- hydroxy, oxo,
- $(C_1-C_6)$alkyl, preferably a methyl,
- aryl, preferably a phenyl,
- aryl$(C_1-C_6)$alkyl, preferably a benzyl,
- hydroxy$(C_1-C_6)$alkyl, preferably hydroxymethyl or hydroxyethyl, and said nitrogen-based heterocycloalkyl being optionally fused with one aryl group, preferably a phenyl.

Especially, $R_3$ and $R_4$ may form, together with the nitrogen to which they are bound, a nitrogen-based heterocycloalkyl represented by the following formula (II):

(II)

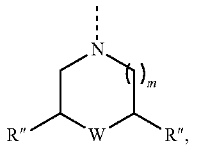

wherein
- m is 1 or 2;
- W represents O, S, NR', $(CH_2)_2$, or CHR';
- R' represents a hydrogen atom, $(C_1-C_6)$alkyl (preferably a methyl), aryl (preferably a phenyl), or aryl$(C_1-C_6)$alkyl (preferably a benzyl); and
- each R" represents independently a hydrogen atom, hydroxy, oxo, $(C_1-C_6)$alkyl (preferably a methyl), aryl (preferably a phenyl), aryl$(C_1-C_6)$alkyl (preferably a benzyl), or hydroxy$(C_1-C_6)$alkyl (preferably hydroxymethyl or hydroxyethyl).

In a particular embodiment, each R" represents independently a hydrogen atom, $(C_1-C_6)$alkyl (preferably a methyl), aryl (preferably a phenyl), or aryl$(C_1-C_6)$alkyl (preferably a benzyl).

In a particular embodiment, $R_3$ and $R_4$ form, together with the nitrogen to which they are bound, a morpholinyl group.

In a particular embodiment, the compound of the invention is a compound of formula (I) wherein at least one of, and preferably all, the following features is (are) fulfilled:
- n is 4; and/or
- X and Y are N and $CR_6$, respectively, with $R_6$ being H or methyl (preferably H); and/or
- $R_1$ represents an aryl group (preferably a phenyl) optionally substituted by at least one —OH, halogen (such as fluorine or chlorine), $(C_1-C_6)$alkyl optionally substituted by one or more fluorine atoms (such as —$CF_3$), or $(C_1-C_6)$alkyloxy (such as methoxy); and/or
- Z is $CR_2$ and, $R_2$ represents H, methyl or phenyl (preferably H); and/or
- $R_3$ and $R_4$ represent independently a radical selected from:
- a hydrogen atom,
- a $(C_1-C_6)$alkyl, preferably a methyl or an ethyl,
- a cycloalkyl, preferably a cyclohexyl or an adamantanyl, and
- an aryl$(C_1-C_6)$alkyl, preferably a benzyl, said radical being optionally substituted by one or two substituents independently selected from the group consisting of:
- a hydroxy,
- a $(C_1-C_6)$alcoxy, preferably a methoxy,
- a heterocycloalkyl, preferably a tetrahydrofuranyl or a tetrahydropyranyl;

and
- an aryl, preferably a phenyl; or form together with the nitrogen to which they are bound a nitrogen-based heterocycloalkyl, preferably a morpholinyl, piperidinyl, piperazinyl, oxazepanyl, azepanyl, azocanyl, nortropanyl, decahydroquinolinyl, thiomorpholinyl, or 6-azabicyclo[3.2.1]octanyl, said nitrogen-based heterocycloalkyl being optionally substituted by at most three substituents independently selected from the group consisting of hydroxy, oxo, $(C_1\text{-}C_6)$alkyl, preferably a methyl, aryl, preferably a phenyl, aryl$(C_1\text{-}C_6)$alkyl, preferably a benzyl, hydroxy$(C_1\text{-}C_6)$alkyl, preferably hydroxymethyl or hydroxyethyl, and said nitrogen-based heterocycloalkyl being optionally fused with one aryl group, preferably a phenyl; and/or each $R_5$ is H;

and a pharmaceutical salt thereof.

In a particular embodiment, a compound of the invention is of formula (I), wherein:

Z represents CH or N, preferably CH;

X and Y are either N and $CR_6$, or CH and CH, respectively (preferably N and $CR_6$), with $R_6$ being H or $(C_1\text{-}C_4)$alkyl (e.g. methyl); and n is 3 or 4, preferably n is 4.

In a particular embodiment, a compound of the invention is of formula (I), wherein $R_1$ represents:

an aryl group, such as a phenyl;

a heteroaryl group, such as a thiophenyl; or a heterocycloalkyl group, such as a piperidinyl;

said group being optionally substituted by at least one —OH, halogen, $(C_1\text{-}C_6)$alkyl optionally substituted by one or more fluorine atoms, or $(C_1\text{-}C_6)$alkyloxy.

In such embodiment, $R_1$ is preferably an aryl group or a heterocycloalkyl group, and more preferably an aryl.

In a particular embodiment, a compound of the invention is of formula (I), wherein $R_3$ and $R_4$ represent independently a radical selected from H, $(C_1\text{-}C_6)$alkyl (e.g. methyl or ethyl), cycloalkyl (e.g. adamantanyl), and aryl$(C_1\text{-}C_6)$alkyl (e.g. benzyl), said radical being optionally substituted by at least one substituent selected from the group consisting of a $(C_1\text{-}C_6)$alcoxy, a heterocycloalkyl (e.g. tetrahydrofuranyl or tetrahydropyranyl), and an aryl (e.g. phenyl).

In another particular embodiment, a compound of the invention is of formula (I), wherein $R_3$ and $R_4$ form, together with the nitrogen to which they are bound, a nitrogen-based heterocycloalkyl, said nitrogen-based heterocycloalkyl being optionally substituted by at least one substituent selected from the group consisting of $(C_1\text{-}C_6)$alkyl, aryl, and aryl$(C_1\text{-}C_6)$alkyl, and said nitrogen-based heterocycloalkyl being optionally fused with at least one 5-14 membered ring selected from aryl (e.g. a phenyl).

Preferred nitrogen-based heterocycloalkyl groups are azepanyl, oxazepanyl, piperidinyl, azocanyl, morpholinyl, thiomorpholinyl, or piperazinyl.

In a particular embodiment, a compound of the invention is of formula (I), wherein:

Z represents CH;

X and Y are either N and $CR_6$, or CH and CH, respectively, with $R_6$ being H or $(C_1\text{-}C_4)$alkyl (e.g. methyl);

n is 3 or 4, preferably n is 4;

$R_1$ represents:

an aryl group, such as a phenyl;

a heteroaryl group, such as a thiophenyl; or a heterocycloalkyl group, such as a piperidinyl;

said group being optionally substituted by at least one —OH, halogen, $(C_1\text{-}C_6)$alkyl optionally substituted by one or more fluorine atoms, or $(C_1\text{-}C_6)$alkyloxy;

$R_3$ and $R_4$:

represent independently a radical selected from H, $(C_1\text{-}C_6)$alkyl (e.g. methyl or ethyl), cycloalkyl (e.g. adamantanyl), and aryl$(C_1\text{-}C_6)$alkyl (e.g. benzyl), said radical being optionally substituted by at least one substituent selected from the group consisting of a $(C_1\text{-}C_6)$alcoxy, a heterocycloalkyl (e.g. tetrahydrofuranyl or tetrahydropyranyl), and an aryl (e.g. phenyl); or form, together with the nitrogen to which they are bound, a nitrogen-based heterocycloalkyl, said nitrogen-based heterocycloalkyl being optionally substituted by at least one substituent selected from the group consisting of $(C_1\text{-}C_6)$alkyl, aryl, and aryl$(C_1\text{-}C_6)$alkyl, and said nitrogen-based heterocycloalkyl being optionally fused with at least one 5-14 membered ring selected from aryl (e.g. a phenyl); and each of $R_5$ represents independently a H.

In a particular embodiment, a compound of the invention is of formula (I), wherein:

Z represents CH or N, preferably CH;

X and Y are either N and $CR_6$, or CH and CH, respectively (preferably N and $CR_6$), with $R_6$ being H or $(C_1\text{-}C_4)$alkyl (e.g. methyl);

n is 3 or 4, preferably n is 4;

$R_1$ represents:

an aryl group, such as a phenyl; or a heterocycloalkyl group, such as a piperidinyl;

$R_3$ and $R_4$:

represent independently a radical selected from H, $(C_1\text{-}C_6)$alkyl (e.g. methyl or ethyl), and aryl$(C_1\text{-}C_6)$alkyl (e.g. benzyl), or form, together with the nitrogen to which they are bound, a nitrogen-based heterocycloalkyl, said nitrogen-based heterocycloalkyl being optionally substituted by at least one substituent selected from the group consisting of aryl, and aryl$(C_1\text{-}C_6)$alkyl, and said nitrogen-based heterocycloalkyl being optionally fused with at least one 5-14 membered ring selected from aryl (e.g. a phenyl); and each of $R_5$ represents independently a H.

In a particular embodiment, a compound of the invention is of formula (I) wherein:

$R_1$ is chosen from H, an aryl$(C_1\text{-}C_6)$alkyl group, an aryl$(C_2\text{-}C_6)$alkenyl group, an aryl group, a heteroaryl group, or a -Q-R group with Q being O or S, and R being an aryl;

said group being optionally substituted by at least one —OH, halogen, $(C_1\text{-}C_6)$alkyl optionally substituted by one or more fluorine atoms, or $(C_1\text{-}C_6)$alkyloxy;

Z is $CR_2$, with $R_2$ being H or a phenyl;

X and Y are N and $CR_6$, respectively;

n is 3, 4, 5, or 6, preferably 4 or 5; and $R_5$ is H;

with the proviso that one of $R_1$ and $R_2$ is different from a hydrogen atom and the other one of $R_1$ and $R_2$ is a hydrogen atom (preferably $R_1$ is different from H and $R_2$ is H).

In such an embodiment, $R_1$ is preferably chosen from H, an aryl group, and a heteroaryl group.

Preferably, a compound of the invention is of formula (I) wherein:

$R_1$ is H or an aryl group (said aryl group being preferably a phenyl);

said aryl group being optionally substituted by at least one halogen (preferably chlorine);

Z is $CR_2$, with $R_2$ being H or a phenyl;

X and Y are N and $CR_6$, respectively;

n is 3, 4, 5 or 6, preferably 4 or 5; and $R_5$ is H;

with the proviso that one of $R_1$ and $R_2$ is different from a hydrogen atom and the other one of $R_1$ and $R_2$ is a hydrogen atom (such as disclosed by the final formula depicted in Scheme 1).

In a more preferred embodiment, a compound of the invention is of formula (I) wherein:

$R_1$ is an aryl group (said aryl group being preferably a phenyl) optionally substituted by at least one halogen (preferably chlorine);

Z is $CR_2$, with $R_2$ being H;

X and Y are N and $CR_6$, respectively;

n is 3, 4, 5 or 6, preferably 4 or 5; and $R_5$ is H.

This embodiment can in particular be illustrated by formulae 9-13 depicted in Scheme 1.

In another more preferred embodiment, a compound of the invention is of formula (I) wherein:

$R_1$ is H;

Z is $CR_2$, with $R_2$ being a phenyl;

X and Y are N and $CR_6$, respectively ($R_6$ being preferably H or methyl);

n is 4 or 5; and $R_5$ is H.

This embodiment can in particular be illustrated by formulae 14-15 depicted in Scheme 1.

As used herein, "a compound of the invention" means a compound described above or a pharmaceutically acceptable salt, any isomer or solvate form thereof.

The term "isomer" refers to compounds which have identical molecular formulae as identified herein but which differ by nature or in the binding sequence of their atoms or in the layout of their atoms in space. Isomers which differ in the layout of their atoms in space are designated by "stereoisomers". Stereoisomers which are not mirror images of each other, are designated as "diastereoisomers", and stereoisomers which are non-superposable mirror images of each other are designated as "enantiomers" or "optical isomers". "Stereoisomers" refer to racemates, enantiomers and diastereoisomers.

The person skilled in the art will recognize that stereocenters exist in the compounds of the invention. Any chiral center of a compound of the invention can be (R), (S) or racemate. Accordingly, the present invention includes all possible stereoisomers and geometric isomers of the compounds of formula (I) and includes not only racemic compounds but also the optically active isomers as well. When a compound of formula (I) is desired as a single enantiomer, it may be obtained either by resolution of the final product or by stereospecific synthesis from either isomerically pure starting material or any suitable intermediate. Resolution of the final product, an intermediate or a starting material may be carried out by any suitable method known in the art. See, for example, Stereochemistry of Carbon Compounds by E. L. Eliel (Mcgraw Hill, 1962) and Tables of Resolving Agents by S. H. Wilen.

The specialist in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of formula (I) are within the scope of the present invention.

It will also be appreciated by the specialist in organic chemistry that many organic compounds can exist in more than one crystalline form. For example, crystalline form may vary from solvate to solvate. Thus, all crystalline forms of the compounds of the invention or the pharmaceutically acceptable solvates thereof are within the scope of the present invention.

The term "pharmaceutically acceptable salts" or "pharmaceutical salts" of the compounds of the invention include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic etc. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

For example, preferred salt forms include hydrochloride.

In a particular embodiment, the compound of formula (I) is selected in the group consisting of:

2-(4-morpholinobutyl)-4-phenylpyridazin-3(2H)-one hydrochloride salt (10b—HCl);

2-(3-(benzyl(methyl)amino)propyl)-4-phenylpyridazin-3(2H)-one (9a);

2-(3-(azepan-1-yl)propyl)-4-phenylpyridazin-3(2H)-one (9b);

2-[3-(morpholin-4-yl)propyl]-4-phenyl-2,3-dihydro-pyridazin-3-one (9c);

2-(4-morpholinobutyl)-4-phenylpyridazin-3(2H)-one (10b);

2-(4-(benzyl(methyl)amino)butyl)-4-phenylpyridazin-3(2H)-one (10a);

2-(4-(1,4-oxazepan-4-yl)butyl)-4-phenylpyridazin-3(2H)-one (10c);

4-phenyl-2-(4-(piperidin-1-yl)butyl)pyridazin-3(2H)-one (10d);

2-(4-(azepan-1-yl)butyl)-4-phenylpyridazin-3(2H)-one (10e);

2-(4-(azocan-1-yl)butyl)-4-phenylpyridazin-3(2H)-one (10f);

2-(4-(3,4-dihydroisoquinolin-2(1H)-yl)butyl)-4-phenylpyridazin-3(2H)-one (10g);

4-phenyl-2-(4-(1,2,4,5-tetrahydro-3H-benzo[d]azepin-3-yl)butyl)pyridazin-3(2H)-one (10h);

2-(4-(adamantan-1-ylamino)butyl)-4-phenylpyridazin-3(2H)-one (10i);

2-(4-(adamantan-1-yl(methyl)amino)butyl)-4-phenylpyridazin-3(2H)-one (10j);

4-phenyl-2-(4-(1,3,3-trimethyl-6-azabicyclo[3.2.1]octan-6-yl)butyl)pyridazin-3(2H)-one (10k);

8-(4-(6-oxo-5-phenylpyridazin-1(6H)-yl)butyl-8-azabicyclo[3.2.1octan-3-one (10l);

2-(4-(benzyl((tetrahydrofuran-2-yl)methyl)amino)butyl)-4-phenylpyridazin-3(2H)-one (10m);

2-(4-((2-methoxy-1-phenylethyl)amino)butyl)-4-phenylpyridazin-3(2H)-one (10n);

2-(4-((2-methoxy-1-phenylethyl)(methyl)amino)butyl)-4-phenylpyridazin-3(2H)-one (10o);

2-(4-((2-hydroxyethyl)(methyl)amino)butyl)-4-phenylpyridazin-3(2H)-one (10p);

2-(4-(methyl((tetrahydro-2H-pyran-4-yl)methyl)amino)butyl)-4-phenylpyridazin-3(2H)-one (10q);

4-phenyl-2-(4-(3-phenylpiperidin-1-yl)butyl)pyridazin-3(2H)-one (10r);

4-phenyl-2-(4-(4-phenylpiperidin-1-yl)butyl)pyridazin-3(2H)-one (10s);

2-(4-(3-(hydroxymethyl)piperidin-1-yl)butyl)-4-phenylpyridazin-3(2H)-one (10t);

2-(4-(2-(2-hydroxyethyl)piperidin-1-yl)butyl)-4-phenylpyridazin-3(2H)-one (10u);

4-phenyl-2-(4-(3-phenylmorpholino)butyl)pyridazin-3(2H)-one (10v);
4-phenyl-2-(4-(2-phenylmorpholino)butyl)pyridazin-3(2H)-one (10w);
2-(4-(2,6-dimethylmorpholino)butyl)-4-phenylpyridazin-3(2H)-one (10x);
2-[4-(4-benzylpiperazin-1-yl)butyl]-4-phenyl-2,3-dihydropyridazin-3-one (10z);
2-[4-(4-benzylpiperidin-1-yl)butyl]-4-phenyl-2,3-dihydropyridazin-3-one (11a);
2-{4-[benzyl(ethyl)amino]butyl}-4-phenyl-2,3-dihydropyridazin-3-one (11b);
2-{4-[cyclohexyl(methyl)amino]butyl}-4-phenyl-2,3-dihydropyridazin-3-one (11c);
4-phenyl-2-[4-(4-phenylpiperazin-1-yl)butyl]-2,3-dihydropyridazin-3-one (11d);
2-{4-[(4aR,8aS)-decahydroquinolin-1-yl]butyl}-4-phenyl-2,3-dihydropyridazin-3-one (11e);
2-(4-{2-oxa-6-azaspiro[3.3]heptan-6-yl}butyl)-4-phenyl-2,3-dihydropyridazin-3-one (11t);
4-phenyl-2-[4-(thiomorpholin-4-yl)butyl]-2,3-dihydropyridazin-3-one (11u);
2-{4-[cyclohexyl(ethyl)amino]butyl}-4-phenyl-2,3-dihydropyridazin-3-one (11g);
4-(4-fluorophenyl)-2-(4-morpholinobutyl)pyridazin-3(2H)-one (11h);
4-(4-hydroxyphenyl)-2-(4-morpholinobutyl)pyridazin-3(2H)-one (11i);
2-(5-morpholinopentyl)-4-phenylpyridazin-3(2H)-one (12);
2-[6-(morpholin-4-yl)hexyl]-4-phenyl-2,3-dihydropyridazin-3-one (13);
2-(4-morpholinobutyl)-5-phenylpyridazin-3(2H)-one (14);
2-(5-morpholinopentyl)-5-phenylpyridazin-3(2H)-one (15);
2-(4-(3-hydroxy-8-azabicyclo[3.2.1]octan-8-yl)butyl)-4-phenylpyridazin-3(2H)-one (16);
4-(4-methoxyphenyl)-2-[4-(morpholin-4-yl)butyl]-2,3-dihydro pyridazin-3-one (11j);
4-(4-chlorophenyl)-2-[4-(morpholin-4-yl)butyl]-2,3-dihydropyridazin-3-one (11k);
4-(3-chlorophenyl)-2-[4-(morpholin-4-yl)butyl]-2,3-dihydropyridazin-3-one (11l);
4-(2-chlorophenyl)-2-[4-(morpholin-4-yl)butyl]-2,3-dihydropyridazin-3-one (11m);
2-[4-(morpholin-4-yl)butyl]-4-[4-(trifluoromethyl)phenyl]-2,3-dihydropyridazin-3-one (11n);
2-[4-(morpholin-4-yl)butyl]-4-(thiophen-3-yl)-2,3-dihydropyridazin-3-one (11o);
4-(furan-3-yl)-2-[4-(morpholin-4-yl)butyl]-2,3-dihydropyridazin-3-one (11p);
4-(3a,7a-dihydro-1-benzofuran-2-yl)-2-[4-(morpholin-4-yl)butyl]-2,3-dihydropyridazin-3-one (11q);
2-[4-(morpholin-4-yl)butyl]-4-(pyridin-3-yl)-2,3-dihydropyridazin-3-one (11r);
2-{4-[benzyl(methyl)amino]butyl}-6-methyl-4-phenyl-2,3-dihydropyridazin-3-one (11v);
2-[4-(azepan-1-yl)butyl]-6-methyl-4-phenyl-2,3-dihydropyridazin-3-one (11w);
2-[4-(morpholin-4-yl)butyl]-4-[(E)-2-phenylethenyl]-2,3-dihydropyridazin-3-one (20a);
2-[4-(morpholin-4-yl)butyl]-4-(2-phenylethyl)-2,3-dihydropyridazin-3-one (21a);
4-(cyclohex-1-en-1-yl)-2-[4-(morpholin-4-yl)butyl]-2,3-dihydropyridazin-3-one (23a);
2-(4-morpholinobutyl)-4-(piperidin-1-yl)pyridazin-3(2H)-one (25a);
2-[4-(morpholin-4-yl)butyl]-4-(1H-pyrrol-1-yl)-2,3-dihydropyridazin-3-one (27a);
2-[4-(morpholin-4-yl)butyl]-4-(phenylsulfanyl)-2,3-dihydropyridazin-3-one (28a);
2-[4-(morpholin-4-yl)butyl]-4-phenoxy-2,3-dihydropyridazin-3-one (29a);
2-(4-(benzyl(methyl)amino)-3-hydroxybutyl)-4-phenylpyridazin-3(2H)-one (33a);
2-methyl-3-(4-morpholinobutyl)-5-phenylpyrimidin-4(3H)-one (40a);
3-[4-(morpholin-4-yl)butyl]-5-phenyl-3,4-dihydropyrimidin-4-one (40b);
1-[4-(morpholin-4-yl)butyl]-3-phenyl-1,2-dihydropyridin-2-one (41a);
1-[4-(morpholin-4-yl)butyl]-3-phenyl-1,2-dihydropyrazin-2-one (46a); and
1-{4-[benzyl(methyl)amino]butyl}-3-phenyl-1,2-dihydropyrazin-2-one (41b).

Preferably, said compound is selected in the group consisting of:

2-(3-(benzyl(methyl)amino)propyl)-4-phenylpyridazin-3(2H)-one (9a);
2-(3-(azepan-1-yl)propyl)-4-phenylpyridazin-3(2H)-one (9b);
2-(4-(benzyl(methyl)amino)butyl)-4-phenylpyridazin-3(2H)-one (10a);
2-(4-(1,4-oxazepan-4-yl)butyl)-4-phenylpyridazin-3(2H)-one (10c);
4-phenyl-2-(4-(piperidin-1-yl)butyl)pyridazin-3(2H)-one (10d);
2-(4-(azepan-1-yl)butyl)-4-phenylpyridazin-3(2H)-one (10e);
2-(4-(azocan-1-yl)butyl)-4-phenylpyridazin-3(2H)-one (10f);
2-(4-(3,4-dihydroisoquinolin-2(1H)-yl)butyl)-4-phenylpyridazin-3(2H)-one (10g);
4-phenyl-2-(4-(1,2,4,5-tetrahydro-3H-benzo[d]azepin-3-yl)butyl)pyridazin-3(2H)-one (10h);
2-(4-(adamantan-1-ylamino)butyl)-4-phenylpyridazin-3(2H)-one (10i);
2-(4-(benzyl((tetrahydrofuran-2-yl)methyl)amino)butyl)-4-phenylpyridazin-3(2H)-one (10m);
2-(4-((2-methoxy-1-phenylethyl)(methyl)amino)butyl)-4-phenylpyridazin-3(2H)-one (10o);
2-(4-(methyl((tetrahydro-2H-pyran-4-yl)methyl)amino)butyl)-4-phenylpyridazin-3(2H)-one (10q);
4-phenyl-2-(4-(3-phenylpiperidin-1-yl)butyl)pyridazin-3(2H)-one (10r);
4-phenyl-2-(4-(4-phenylpiperidin-1-yl)butyl)pyridazin-3(2H)-one (10s);
2-(4-(2,6-dimethylmorpholino)butyl)-4-phenylpyridazin-3(2H)-one (10x);
4-phenyl-2-(4-(2-phenylmorpholino)butyl)pyridazin-3(2H)-one (10w);
2-[4-(4-benzylpiperazin-1-yl)butyl]-4-phenyl-2,3-dihydropyridazin-3-one (10z);
2-[4-(4-benzylpiperidin-1-yl)butyl]-4-phenyl-2,3-dihydropyridazin-3-one (11a);
2-{4-[benzyl(ethyl)amino]butyl}-4-phenyl-2,3-dihydropyridazin-3-one (11b);
2-[4-(morpholin-4-yl)butyl]-4-(thiophen-3-yl)-2,3-dihydropyridazin-3-one (11o);
4-phenyl-2-[4-(thiomorpholin-4-yl)butyl]-2,3-dihydropyridazin-3-one (11u);
2-{4-[benzyl(methyl)amino]butyl}-6-methyl-4-phenyl-2,3-dihydropyridazin-3-one (11v);
2-[4-(azepan-1-yl)butyl]-6-methyl-4-phenyl-2,3-dihydropyridazin-3-one (11w);

2-(4-morpholinobutyl)-4-(piperidin-1-yl)pyridazin-3(2H)-one (25a); and

1-{4-[benzyl(methyl)amino]butyl}-3-phenyl-1,2-dihydropyrazin-2-one (41b).

More preferably, said compound is selected in the group consisting of:

2-(3-(benzyl(methyl)amino)propyl)-4-phenylpyridazin-3(2H)-one (9a);

2-(4-(benzyl(methyl)amino)butyl)-4-phenylpyridazin-3(2H)-one (10a);

2-(4-(azocan-1-yl)butyl)-4-phenylpyridazin-3(2H)-one (10f);

2-(4-(3,4-dihydroisoquinolin-2(1H)-yl)butyl)-4-phenylpyridazin-3(2H)-one (10g);

4-phenyl-2-(4-(1,2,4,5-tetrahydro-3H-benzo[d]azepin-3-yl)butyl)pyridazin-3(2H)-one (10h);

4-phenyl-2-(4-(3-phenylpiperidin-1-yl)butyl)pyridazin-3(2H)-one (10r);

4-phenyl-2-(4-(4-phenylpiperidin-1-yl)butyl)pyridazin-3(2H)-one (10s);

2-[4-(4-benzylpiperazin-1-yl)butyl]-4-phenyl-2,3-dihydropyridazin-3-one (10z);

2-[4-(4-benzylpiperidin-1-yl)butyl]-4-phenyl-2,3-dihydropyridazin-3-one (11a);

2-{4-[benzyl(ethyl)amino]butyl}-4-phenyl-2,3-dihydropyridazin-3-one (11b);

4-phenyl-2-[4-(thiomorpholin-4-yl)butyl]-2,3-dihydropyridazin-3-one (11u);

2-{4-[benzyl(methyl)amino]butyl}-6-methyl-4-phenyl-2,3-dihydropyridazin-3-one (11v);

2-[4-(azepan-1-yl)butyl]-6-methyl-4-phenyl-2,3-dihydropyridazin-3-one (11w); and 2-(4-morpholinobutyl)-4-(piperidin-1-yl)pyridazin-3(2H)-one (25a).

The compounds of the invention can be prepared by several methods, and in particular the methods as illustrated in the examples. The starting products are commercial products or products prepared according to known synthesis from commercial compounds or known to one skilled in the art.

Therapeutic Use of the Compounds

The present invention relates to a pharmaceutical or veterinary composition comprising a compound according to the invention. Preferably, the pharmaceutical composition further comprises a pharmaceutically or veterinary acceptable carrier (or "support") or excipient. The invention further relates to a method for treating a disease in a subject, wherein a therapeutically effective amount of a compound according to the invention, is administered to said subject in need thereof. The present invention relates to the use of a compound according to the invention as a medicine. The invention also relates to the use of a compound according to the invention, for the manufacture of a medicine.

In addition, the present invention relates to a method for treating of a disorder modulated by mi receptor (e.g. cognitive or neurodegenerative disorders), in a subject, wherein a therapeutically effective amount of a compound according to the invention, is administered to said subject suffering of a disorder modulated by sigma-1 receptor (e.g. cognitive or neurodegenerative disorders).

The invention also relates to the use of the compounds according to the invention, for the manufacture of a medicine for the treatment of a disorder modulated by sigma-1 receptor (e.g. cognitive or neurodegenerative disorders). The invention relates to a compound according to the invention for use in the treatment of a disorder modulated by sigma-1 receptor (e.g. cognitive disorders).

In a particular embodiment of the invention, said disorder modulated by sigma-1 receptor is selected from the group consisting of (1) neurodegenerative diseases including, but not limited to, Alzheimer disease, Parkinson's disease, Huntington's disease, Amyotrophic lateral sclerosis, multiple sclerosis; (2) cognitive and memory alterations including, but not limited to, pathological ageing, ischemic amnesia, schizophrenia-related cognitive deficits, depression; (3) developmental cognitive disorders including, but not limited to, autism-related disorders, mental retardation-related disorders; and (4) genetic diseases associated with MAM dysfunctions.

Pharmaceutical Compositions

The present invention also relates to a pharmaceutical composition comprising a compound of the present invention. The composition further comprises at least one pharmaceutically acceptable carrier (or "support") or excipient.

The invention also concerns the pharmaceutical composition of the invention for use in the treatment of a disease. The invention also relates to the use of a pharmaceutical composition according to the invention for the manufacture of a medicine for treating a disease in a subject.

The invention further relates to a method for treating a disease in a subject, wherein a therapeutically effective amount of a pharmaceutical composition according to the invention is administered to said subject suffering from said disease.

Preferably, the disease is a disorder modulated by sigma-1 receptor. More preferably, the disease is selected from the group consisting of (1) neurodegenerative diseases including, but not limited to, Alzheimer disease, Parkinson's disease, Huntington's disease, Amyotrophic lateral sclerosis, multiple sclerosis; (2) cognitive and memory alterations including, but not limited to, pathological ageing, ischemic amnesia, schizophrenia-related cognitive deficits, depression; (3) developmental cognitive disorders including, but not limited to, autism-related disorders, mental retardation-related disorders; and (4) genetic diseases associated with MAM dysfunctions.

Subject, Regimen and Administration

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human subject according to the invention may be a human at the prenatal stage, a newborn, a child, an infant, an adolescent or an adult, in particular an adult of at least 40 years old, preferably an adult of at least 50 years old.

In a preferred embodiment, the subject has been diagnosed with a disease. Preferably, the subject has been diagnosed with a disease modulated by sigma-1 receptor.

Diagnostic methods of these diseases are well known by the man skilled in the art.

The compound according to the invention or the pharmaceutical composition according to the invention may be administered by any conventional route of administration. In particular, the compound or the pharmaceutical composition of the invention can be administered by a topical, enteral, oral, parenteral, intranasal, intravenous, intra-arterial, intramuscular, intratumoral, subcutaneous or intraocular administration and the like.

In particular, the compound according to the invention or the pharmaceutical composition according to the invention can be formulated for a topical, enteral, oral, parenteral, intranasal, intravenous, intra-arterial, intramuscular, subcutaneous or intraocular administration and the like.

Preferably, the compound according to the invention or the pharmaceutical composition according to the invention is administered by enteral or parenteral route of administration. When administered parenterally, the compound according to the invention or the pharmaceutical composition according to the invention is preferably administered by intravenous route of administration. When administered enterally, the compound according to the invention or the pharmaceutical composition according to the invention is preferably administered by oral route of administration.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatin, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Preferably, the treatment with the compound according to the invention or the pharmaceutical composition according to the invention starts no longer than one year, preferably no longer than six, five, four, three, two or one month(s), after the diagnosis of the disease.

The compound according to the invention or the pharmaceutical composition according to the invention may be administered as a single dose or preferably in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, such as 2 or 3 times a day.

The duration of treatment with the compound according to the invention or the pharmaceutical composition according to the invention is preferably comprised between one week, more preferably between one week and one or more year(s). Alternatively, the treatment may last as long as the disease persists.

The amount of compound according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient. In a preferred embodiment, the total compound dose for each administration of the compound according to the invention or of the pharmaceutical composition according to the invention is comprised between 0.00001 and 1 g, preferably between 0.01 and 10 mg.

The form of the pharmaceutical compositions, the route of administration and the dose of administration of the compound according to the invention, or the pharmaceutical composition according to the invention can be adjusted by the man skilled in the art according to the type and severity of the disease, and to the patient, in particular its age, weight, sex, and general physical condition.

The invention will also be described in further detail in the following examples, which are not intended to limit the scope of this invention, as defined by the attached claims.

EXAMPLES

The following synthetic methods and schemes illustrate the general procedures by which the compounds of the present invention can be prepared. Starting materials have been obtained from commercially sources or prepared by using methods well known to those of ordinary skill in the art. For example, the compounds of the present invention can be prepared in accordance with or in analogy to the synthetic routes described in detail in the examples section. In particular compounds of the general formula (I) and their pharmaceutically acceptable salts can be synthesized according to methods described in the following schemes where X represents a halogen and R any group at the corresponding position of the general formula (I). While the numbering of the groups R in the following schemes differs from the designation of the groups in the general formula (I), it will be understood that these schemes explain the preparation of compounds of formula (I) and thus these groups R are defined in accordance with the corresponding groups at the same positions in attachment in the general formula (I). Purification of intermediates and final products was carried out via normal or reverse phase chromatography using a Dionex UltiMate 300 with the following parameters: Flow rate of 0.5 mL/min, column temperature: 30° C., solvent system: A (MeOH) and B (0.05% of TFA in $H_2O$), t=0 min to 1 min: 50 to 60% of B then t=1 min to t=10 min: 60 to 100% of B and t=10 min to t=15 min: 100% of B.

Part A. Preparation of Compounds According to the Invention

General Synthetic Methods and Examples

Method 1: Preparation of N-substituted 4-Ar (5-Ar)-pyridazine 3(2H)-one: 9-15

The preparation of compounds of formula 9-15 can be carried out along various synthetic routes using conventional methods (see Scheme 1). Starting from commercially available or previously described 4 or 5-halogeno pyridazinones a Suzuki-Miyaura cross coupling reaction with aryl boronic acids in presence of tetrakis(triphenylphosphine) palladium led to the corresponding 4 or 5 Aryl pyridazinone derivatives 1-2. N-Alkylation of intermediate 1-2 with appropriate alkyl-dihalides with the use of NaH in DMF led to intermediates 3-8. Finally a nucleophilic substitution reaction was performed with appropriate aliphatic amines $NHR_3R_4$ leading to compounds of general formula 9-15.

Scheme 1

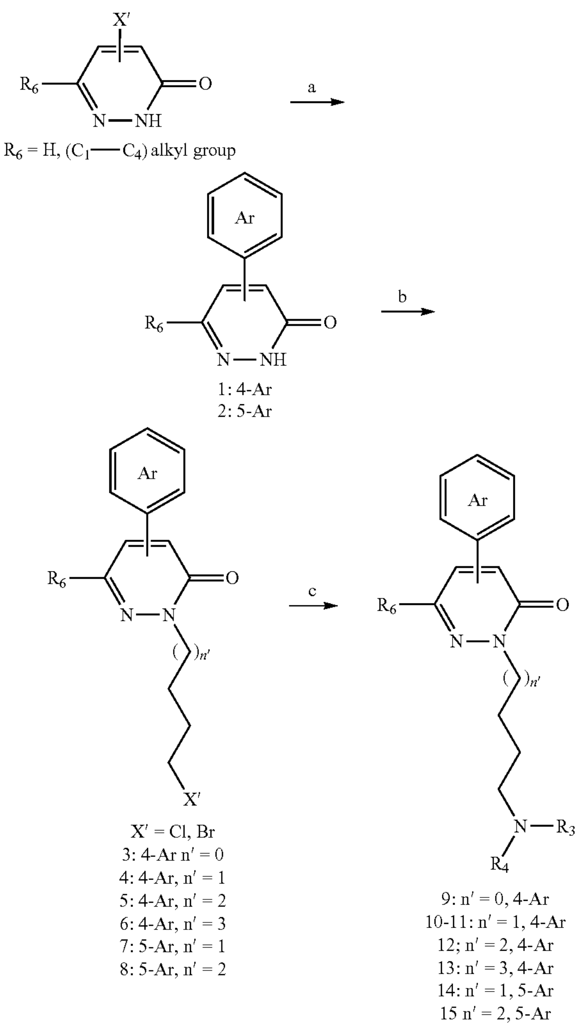

$R_6$ = H, ($C_1$—$C_4$) alkyl group

1: 4-Ar
2: 5-Ar

X' = Cl, Br
3: 4-Ar n' = 0
4: 4-Ar, n' = 1
5: 4-Ar, n' = 2
6: 4-Ar, n' = 3
7: 5-Ar, n' = 1
8: 5-Ar, n' = 2

9: n' = 0, 4-Ar
10-11: n' = 1, 4-Ar
12; n' = 2, 4-Ar
13: n' = 3, 4-Ar
14: n' = 1, 5-Ar
15 n' = 2, 5-Ar

Conditions: a) Ar—$B(OH)_2$, $Pd(PPh_3)_4$, $Na_2CO_3$, Toluene, EtOH, $H_2O$, 120° C., 16 h. b) $Br(CH_2)_{n'+3}$—X, NaH, DMF, 0° C. → 25° C., 12 h. c) $K_2CO_3$, $HNR_3R_4$, MeCN. n' = 0, 1, 2, or 3

4-phenylpyridazin-3(2H)-one 1a

A microwave vial (oven-dried and under-3-one (2.0 g, 15.32 mmol, 1.0 equiv.), sodium carbonate (4.87 g, 45.97 mmol, 3 equiv.), Tetrakis (triphenylphosphine) palladium (0) (885.3 mg, 5 mol %) was then added, followed by toluene (38 mL), $H_2O$ (8 mL) and EtOH (8 mL). The vial was properly capped and the mixture vessel was evacuated and backfilled with argon (argon) was charged with phenylboronic acid (2.06 g, 16.85 mmol, 1.1 equiv.), 4-chloro-2,3-dihydropyridazin process repeated 3 times), and heated at 120° C. until complete conversion of the starting material. The reaction conversion was monitored by HPLC and was usually completed within 16 hours. After cooling to room temperature, the reaction mixture was evaporated to dryness. The crude was partitioned through EtOAc (30 mL) and $H_2O$ (50 mL). The aqueous phase was extracted twice with EtOAc (20 mL). The organic phases were combined, washed with brine and dried ($Na_2SO_4$) and evaporated. The crude material was purified by silica gel chromatography (EtOAc/heptane, 1/1, 7/3 to 1/0) to yield a yellow solid (masse=2.34 g, yield=89%).

$^1H$ NMR (400 MHz, DMSO-$d_6$) δ 13.20 (bs, 1H), 7.95 (d, J=3.9 Hz, 1H), 7.89-7.84 (m, 2H), 7.58 (d, J=3.9 Hz, 1H), 7.49-7.41 (m, 3H). $^{13}C$ NMR (101 MHz, DMSO-$d_6$) δ 160.9, 138.7, 137.8, 134.2, 129.8, 129.2, 128.9, 128.7.

4-(4-fluorophenyl)pyridazin-3(2H)-one 1b

Using the same procedure than described for preparation of compound 1a and starting from 4-chloro-2,3-dihydropyridazin-3-one (180.0 mg, 1.37 mmol, 1 equiv.) and 4-fluoro benzene boronic acid (212.2 mg, 1.51 mmol, 1.1 equiv.) the title compound was obtained as an orange powder (masse=160.1 mg, yield=61%).

$^1H$ NMR (400 MHz, DMSO-$d_6$) δ 13.19 (s, 1H), 7.96-7.90 (m, 2H), 7.89 (d, J=4.1 Hz, 1H), 7.53 (d, J=4.1 Hz, 1H), 7.20 (t, J=8.6 Hz, 2H). $^{13}C$ NMR (101 MHz, DMSO-$d_6$) δ 163.7, 161.3, 160.3, 137.7, 137.5, 131.2, 131.1, 130.5, 130.4, 129.8, 129.7, 128.1, 114.9, 114.7.

4-(4-((tetrahydro-2H-pyran-2-yl)oxy)phenyl) pyridazin-3(2H)-one 1c

Using the same procedure than described for preparation of compound 1a and starting from 4-chloro-2,3-dihydropyridazin-3-one (180.0 mg, 1.37 mmol, 1 equiv.) and 4-(2-tetrahydropyranyloxy) phenylboronic acid (336.8 mg, 1.51 mmol, 1.1 equiv.) the title compound was obtained as a yellow solid (masse=173.1 mg, yield=46%).

$^1H$ NMR (400 MHz, DMSO-$d_6$) δ 13.1 (s, 1H), 7.92 (J=4.3 Hz, 1H), 7.88 (d, J=8.8 Hz, 1H), 7.55 (d, J=4.3 Hz, 1H), 7.09 (d, J=8.8 Hz, 1H), 5.59-5.53 (m, 1H), 3.79-3.71 (m, 1H), 3.61-3.53 (m, 1H), 1.94-1.70 (m, 3H), 168-1.47 (m, 3H). $^{13}C$ NMR (101 MHz, DMSO-$d_6$) δ 161.1, 157.9, 136.1, 137.8, 130.3, 127.9, 127.2, 116.5, 96.1, 62.0, 30.2, 25.1, 19.0.

6-methyl-4-phenyl-2,3-dihydropyridazin-3-one 1d[1]: For Preparation See

[1a]—Chin. J. Org. Chem., 2014, 34, 722-728;

[1b]—Pest Manag Sci., 2006, 62, 522-530.

5-phenylpyridazin-3(2H)-one 2[2]: For Preparation See

[2]—Tetrahedron, 2004, 60(52), 12177-12189.

2-(3-chloropropyl)-4-phenylpyridazin-3(2H)-one 3a

The reaction was performed in anhydrous conditions under argon atmosphere. To a solution of 4-phenylpyridazin-3(2H)-one 1 (50 mg, 0.29 mmol, 1 equiv.) in dry DMF (1.0 mL) cooled to 0° C. was added portionwise NaH (1.5 eq., 10.45 mg, 0.43 mmol) and the mixture was stirred at 0° C. for 30 min. Then, 1-bromo-3-chloropropane (137.2 mg, 86 μL, 0.87 mmol, 3.0 equiv.) was added dropwise at 0° C. and the mixture was allowed to warm up to rt and stirred for 3 h. The mixture was quenched with $H_2O$ (5 mL) and extracted with EtOAc (2×5 mL). The combined organic layers were washed with brine, dried over $Na_2SO_4$, filtered and concentrated to dryness. The crude was purified by column chromatography over silica gel (solid loading, eluent: Heptane/EtOAc: 3/1) to give the title compound as a yellow oil (masse=49 mg, yield=68%).

$^1$H NMR (400 MHz, $CDCl_3$) δ 7.81 (d, J=4.2 Hz, 1H), 7.77-7.72 (m, 2H), 7.44-7.37 (m, 3H), 7.26 (d, J=4.2 Hz, 1H), 4.38 (t, J=6.8 Hz, 2H), 3.60 (t, J=6.5 Hz, 2H), 2.31 (quin, J=6.8 Hz, 2H). $^{13}$C NMR (101 MHz, $CDCl_3$) δ 160.1, 139.8, 136.4, 133.7, 129.6, 128.6, 128.4, 127.6, 50.2, 42.1, 31.2.

2-(4-chlorobutyl)-4-phenylpyridazin-3(2H)-one 4a

Using the same procedure described for 3a and starting from 4-phenylpyridazin-3(2H)-one 1 (620 mg, 3.60 mmol, 1 equiv.) and 1-bromo-4 chlorobutane (1.85 g, 1.25 mL, 10.8 mmol, 3 equiv.) and NaH 60% dispersion in mineral oil (216 mg, 5.40 mmol, 1.5 equiv.), the title compound was obtained as a yellow gum (masse=753 mg, yield=80%).

$^1$H NMR (400 MHz, $CDCl_3$) δ 7.66 (d, J=4.1 Hz, 1H), 7.64-7.59 (m, 2H), 7.32-7.22 (m, 3H), 7.12 (d, J=4.1 Hz, 1H), 4.12 (t J=7.1 Hz, 2H), 3.43 (t, J=6.5 Hz, 2H), 1.87 (quin, J=7.1 Hz, 2H), 1.87 (quin, J=6.8 Hz, 2H). $^{13}$C NMR (101 MHz, $CDCl_3$) δ 160.0, 139.8, 136.3, 133.9, 129.6, 128.7, 128.4, 127.5, 51.6, 44.4, 33.0, 29.6, 25.7.

2-(4-chlorobutyl)-4-(4-fluorophenyl)-2,3-dihydropyridazin-3-one 4b

Using the same procedure described for 3a and starting from 4-(4-fluorophenyl)pyridazin-3(2H)-one 1b (150 mg, 0.79 mmol, 1 equiv.) and 1-bromo-4 chlorobutane (405.7 mg, 274 μL, 2.4 mmol, 3 equiv.) and NaH 95% (29.9 mg, 1.18 mmol, 1.5 equiv.), the title compound was obtained as a yellow oil (masse=115 mg, yield=52%).

HPLC C18: 10%- 100% 8 min: 4b (retention time (RT): 3.99 min); diadduct (RT: 4.11 min.).

$^1$H NMR (400 MHz, $CDCl_3$) δ 7.83-7.77 (m, 3H), 7.25 (d, J=4.2 Hz, 1H), 7.15-7.08 (m, 2H), 4.27 (t, J=7.2 Hz, 2H), 3.58 (t, J=6.6 Hz, 2H), 2.06-1.98 (m, 2H), 1.89-1.81 (m, 2H).

$^1$H NMR diadduct (400 MHz, $CDCl_3$) 8.83-7.77 (m, 3H), 7.25 (d, J=4.2 Hz, 1H), 7.15-7.08 (m, 2H), 4.27 (t, J=7.2 Hz, 2H), 3.45 (m, 2H), 2.06-1.90 (m, 2H).

2-(4-chlorobutyl)-4-(4-((tetrahydro-2H-pyran-2-yl)oxy)phenyl)pyridazin-3(2H)-one 4c Using the same procedure described for 3a and starting from 4-(4-((tetrahydro-2H-pyran-2-yl)oxy)phenyl)pyridazin-3(2H)-one 1c (150 mg, 0.55 mmol, 1 equiv.) and 1-bromo-4 chlorobutane (283.4 mg, 191 μL, 1.65 mmol, 3 equiv.) and NaH 95% (20.9 mg, 0.83 mmol, 1.5 equiv.), the title compound was obtained as a yellow oil (masse=80 mg, yield=40%).

$^1$H NMR (400 MHz, $CDCl_3$) δ 7.79-7.73 (m, 3H), 7.21 (d, J=4.3 Hz, 1H), 7.10-7.06 (m, 2H), 5.46 (t, J=3.2 Hz, 1H), 4.25 (t, J=7.1 Hz, 2H), 3.85 (ddd, J=11.4 Hz, J=9.8 Hz, J=3.2 Hz, 1H), 3.61-3.54 (m, 1H), 3.56 (t, J=6.5 Hz, 2H), 2.04-1.95 (m, 3H), 1.87-1.79 (m, 4H), 1.72-1.64 (m, 3H).

2-(4-chlorobutyl)-6-methyl-4-phenyl-2,3-dihydropyridazin-3-one 4d

Using the same procedure described for 3a and starting from 6-methyl-4-phenyl-2,3-dihydropyridazin-3-one 1d (75 mg, 0.4 mmol, 1 equiv.), and 1-bromo-4 chlorobutane (207.2 mg, 140 μL, 1.20 mmol, 3 equiv.) and NaH 100% (14.5 mg, 0.60 mmol, 1.5 equiv.), the title compound was obtained as a yellow oil (masse=97 mg, yield=87%).

$^1$H NMR (400 MHz, $CDCl_3$) δ 7.77-7.72 (m, 2H), 7.44-7.35 (m, 3H), 7.16 (s, 1H), 4.21 (t, J=7.222 Hz, 2H), 3.57 (t, J=6.6 Hz, 2H), 2.35 (s, 3H), 1.99 (quin, J=7.2 Hz, 2H), 1.88-1.80 (m, 2H). $^{13}$C NMR (101 MHz, $CDCl_3$) δ 159.3, 144.5, 139.4, 134.0, 129.5, 129.4, 128.7, 128.3, 51.3, 44.5, 29.7, 25.8, 21.1.

2-(5-bromopentyl)-4-phenyl-2,3-dihydropyridazin-3-one 5a

Using the same procedure described for 3a and starting from 4-phenylpyridazin-3(2H)-one 1 (120 mg, 0.70 mmol, 1 equiv.) and 1,5-dibromopentane (490.8 mg, 0.29 mL, 2.09 mmol, 3 equiv.) and NaH 60% dispersion in mineral oil (41.8 mg, 1.04 mmol, 1.5 equiv.), the title compound was obtained as an gum (masse=110 mg, yield=49%). The presence of the diadduct 2,2'-(butane-1,4-diyl)bis(4-(4-fluorophenyl)pyridazin-3(2H)-one) was detected by $^1$H NMR and HPLC (~20%). The product was used in the next step without further purification.

$^1$H NMR (400 MHz, $CDCl_3$) δ 7.83 (d, J=4.2 Hz, 1H), 7.81-7.77 (m, 2H), 7.48-7.40 (m, 3H), 7.28 (d, J=4.2 Hz, 1H), 4.26 (t, J=7.6 Hz, 2H), 3.42 (J=6.8 Hz, 2H), 1.97-1.90 (m, 4H), 1.58-1.50 (m, 2H).

2-(6-chlorohexyl)-4-phenyl-2,3-dihydropyridazin-3-one 6a

Using the same procedure described for 3a and starting from 4-phenylpyridazin-3(2H)-one 1 (50 mg, 0.29 mmol, 1 equiv.) and 1-bromo-6-chlorohexane (173.8 mg, 0.87 mmol, 130 μL, 3 equiv.) and NaH, (10.4 mg, 0.43 mmol, 1.5 equiv.), the title compound was obtained as a yellow oil (masse=52.3 mg, yield=62%).

$^1$H NMR (400 MHz, $CDCl_3$) δ 7.66 (d, J=4.2 Hz, 1H), 7.64-7.60 (m, 2H), 7.31-7.23 (m, 3H), 7.11 (d, J=4.2 Hz, 1H), 4.08 (t, J=7.5 Hz, 2H), 3.36 (t, J=6.7 Hz, 2H), 1.71 (quin, J=7.5 Hz, 2H), 1.62 (quin, J=6.7 Hz, 2H), 1.39-1.20 (m, 4H). $^{13}$C NMR (101 MHz, $CDCl_3$) δ 160.0, 139.7, 136.2, 134.0, 129.5, 128.7, 128.4, 127.4, 52.5, 45.0, 32.4, 28.1, 26.5, 26.0.

2-(4-chlorobutyl)-5-phenylpyridazin-3(2H)-one 7a

Using the same procedure described for 3a and starting from 5-phenylpyridazin-3(2H)-one 2 (200 mg, 1.16 mmol, 1 equiv.) and 1-bromo-4 chlorobutane (597.5 mg, 0.40 mL, 3.48 mmol, 3 equiv.) and NaH 60% dispersion in mineral oil (41.8 mg, 1.04 mmol, 1.5 equiv.), the title compound was obtained as an gum (masse=209 mg, yield=68%). The presence of the diadduct (2,2'-(butane-1,4-diyl)bis(5-phenylpyridazin-3(2H)-one) was detected by $^1$H NMR and HPLC (~20%). The product was used in the next step without further purification.

HPLC: C18: 10%-100%, 8 min: 4a (RT: 4.00); diadduct (RT: 4.017)

$^1$H NMR (400 MHz, $CDCl_3$) δ 8.06 (d, J=2.3 Hz, 1H), 7.60-7.54 (m, 2H), 7.53-7.47 (m, 3H), 7.06 (d, J=2.3 Hz, 1H), 4.24 (t, J=7.1 Hz, 2H), 3.6 (t, J=6.5 Hz, 2H), 2.06-1.98 (m, 2H), 1.91-1.83 (m, 2H).

$^1$HNMR diadduct (400 MHz, $CDCl_3$) δ 0.06 (d, J=2.3 Hz, 2H), 7.60-7.54 (m, 4H), 7.53-7.47 (m, 6H), 7.06 (d, J=2.3 Hz, 2H), 4.24 (t, J=7.1 Hz, 2H), 3.6 (t, J=6.5 Hz, 2H), 2.06-1.98 (m, 2H), 1.98-1.93 (m, 2H).

2-(5-chloropentyl)-5-phenylpyridazin-3(2H)-one 8a

Using the same procedure described for 3a and starting from 5-phenylpyridazin-3(2H)-one 2 (200 mg, 1.16 mmol, 1 equiv.) and 1,5-dibromopentane (801.3 mg, 0.48 mL, 3.48 mmol, 3 equiv.) and NaH 60% dispersion in mineral oil (69.7 mg, 1.74 mmol, 1.5 equiv.), the title compound was obtained (masse=256 mg, yield=69%). The presence of the diadduct (2,2'-(pentane-1,5-diyl)bis(5-phenylpyridazin-3(2H)-one) was detected by $^1$H NMR and HPLC (~15%). The product was used in the next step without further purification.

$^1$H NMR (400 MHz, $CDCl_3$) δ 8.06 (d, J=2.3 Hz, 1H), 7.61-7.55 (m, 2H), 7.53-7.48 (m, 3H), 7.06 (d, J=2.3 Hz, 1H), 4.22 (t, J=7.3 Hz, 2H), 3.42 (t, J=6.8 Hz, 2H), 1.98-1.84 (m, 4H), 1.60-1.49 (m, 2H).

Example A-1: 4-phenyl-2-(4-(piperidin-1-yl)butyl) pyridazin-3(2H)-one 10d

To a solution of 2-(4-chlorobutyl)-4-phenylpyridazin-3(2H)-one 4a (125 mg, 0.38 mmol, 1 equiv) in MeCN (1.35 mL) and under argon was added piperidine (129.6 mg, 1.52 mmol, 4 equiv), $K_2CO_3$ (105.2 mg, 0.76 mmol, 2 equiv.) and NaI (5.7 mg, 10 mol %) and the reaction mixture was heated at 80° C. overnight under argon. The mixture was then quenched with $H_2O$ (15 mL) and extracted twice with EtOAc (10 mL). The combined organic layers were dried over $Na_2SO_4$, filtered and evaporated to dryness. The resulting residue was purified by silica gel flash chromatography using a gradient of 2% to 5% of MeOH in EtOAc to give the title compound 10d (masse=95 mg, yield=80%).

$^1$H NMR (400 MHz, $CDCl_3$) δ 7.62 (d, J=4.2 Hz, 1H), 7.80-7.75 (m, 2H), 7.47-7.38 (m, 3H), 7.27 (d, J=4.2 Hz, 1H), 4.26 (t, J=7.4 Hz, 2H), 2.49-2.32 (m, 6H), 1.87 (quin, J=7.5 Hz, 2H), 1.66-1.54 (m, 6H), 1.47-1.39 (m, 2H). $^{13}$C NMR (101 MHz, $CDCl_3$) δ 160.0, 140.4, 136.1, 134.0, 129.5, 128.7, 128.4, 127.4, 58.9, 54.5, 52.4, 26.5, 25.7, 24.3, 23.9.

4-phenyl-2-(4-(piperidin-1-yl)butyl)pyridazin-3(2H)-one hydrochloride salt of 10d 95 mg of the above solid was dissolved in a minimum of methanol and the solution was treated with an excess of 2N HCl in $Et_2O$ (180 μL). After stirring for 15 min the resulting mixture was concentrated under vacuum, coevaporated twice with $Et_2O$ and then triturated with ice-cooled pentane. The supernatant was removed and the residue was dried under vacuum than lyophilized to yield the title compounds as a hydrochloride salt (masse=98 mg).

LC/MS (M+H)=312.20

2-(4-morpholinobutyl)-4-phenylpyridazin-3(2H)-one, 10b

Using the same procedure described for 10d and starting from 2-(4-chlorobutyl)-4-phenylpyridazin-3(2H)-one 4a (90 mg, 0.325 mmol, 1 equiv.) and morpholine (87.1 mg, 143 μL, 1.62 mmol), NaI (4.9 mg, 10 mol %) and $K_2CO_3$ (138.2 mg, 0.65 mmol, 2 equiv.), the title compound was obtained after salification and lyophilization (masse=58 mg, yield=94%).

$^1$H NMR (400 MHz, $CDCl_3$): δ ppm 7.81 (d, 1H, J=4.4 Hz), 7.79-7.76 (m, 2H), 7.46-7.40 (m, 3H), 7.26 (d, J=4.4 Hz, 1H), 4.26 (t, J=7.2 Hz, 2H), 3.71 (t, J=4.8 Hz, 4H), 2.45-2.37 (m, 6H), 1.90 (quin, J=7.5 Hz, 2H), 1.59 (quin, J=7.7 Hz, 2H). $^{13}$CNMR (100 MHz, $CDCl_3$): δ ppm 160.0, 139.7, 136.1, 133.9, 129.5, 128.7, 128.4, 127.4, 66.9, 58.5, 53.7, 52.3, 26.3, 23.6.

LC/MS (M+H)=314.18

2-(3-(benzyl(methyl)amino)propyl)-4-phenylpyridazin-3(2H)-one 9a

Using the same procedure described for 10d and starting from 2-(3-chloropropyl)-4-phenylpyridazin-3(2H)-one 3a (96 mg, 0.39 mmol, 1 equiv.) and N-methylbenzylamine (93.5 mg, 0.77 mmol, 2 equiv.), NaI (5.8 mg, 0.039 mmol, 0.1 equiv), $Na_2CO_3$ (61.4 mg, 0.6 mmol, 1.5 equiv.), the title compound was obtained after salification and lyophilization (masse=62 mg, yield=43%).

$^1$H NMR (400 MHz, $CDCl_3$) δ 7.81-7.78 (m, 3H), 7.49-7.40 (m, 3H), 7.33-7.21 (m, 6H), 4.21 (t, J=7.9 Hz, 2H), 3.51 (s, 2H), 2.51 (t, J=7.1 Hz, 2H), 2.22 (s, 3H), 2.08 (q, J=7.1 Hz, 2H) $^{13}$C NMR (101 MHz, $CDCl_3$) δ 160.0, 139.7, 139.2, 136.2, 134.1, 129.5, 129.1, 128.8, 128.4, 128.2, 127.5, 126.9, 62.3, 54.5, 51.2, 42.0, 26.1.

LC/MS (M+H)=334.17

2-(3-(azepan-1-yl)propyl)-4-phenylpyridazin-3(2H)-one 9b

Using the same procedure described for 10d and starting from 2-(3-chloropropyl)-4-phenylpyridazin-3(2H)-one 3a (80 mg, 0.32 mmol, 1 equiv.) and azepane (63.8 mg, 72.5 μL, 0.64 mmol, 2 equiv.), NaI (4.8 mg, 0.032 mmol, 0.1 equiv), $Na_2CO_3$ (51.1 mg, 0.48 mmol, 1.5 equiv.), the title compound was obtained after salification and lyophilization (masse=64 mg, yield=57%).

$^1$H NMR (400 MHz, $CDCl_3$) δ 7.79 (d, J=4.2 Hz, 1H), 7.78-7.74 (m, 2H), 7.44-7.36 (m, 3H), 7.24 (d, J=4.2 Hz, 1H), 4.26 (t, J=7.2 Hz, 2H), 2.66-2.56 (m, 6H), 2.02 (quin, J=7.2 Hz, 2H), 1.65-1.62 (m, 8H).

$^{13}$C NMR (101 MHz, $CDCl_3$) δ 160.1, 139.7, 136.2, 134.2, 129.6, 128.8, 128.5, 127.5, 55.5, 55.4, 51.4, 28.1, 27.1, 26.4.

LC/MS (M+H)=312.18

2-[3-(morpholin-4-yl)propyl]-4-phenyl-2,3-dihydropyridazin-3-one 9c

Using the same procedure described for 10d and starting from 2-(3-chloropropyl)-4-phenylpyridazin-3(2H)-one 3a (49 mg, 0.2 mmol, 1 equiv.) and morpholine (85.8 mg, 0.98 mmol, 5 equiv.), NaI (2.9 mg, 0.02 mmol, 0.1 equiv.), $Na_2CO_3$ (42 mg, 0.4 mmol, 2 equiv.), the title compound was obtained after salification and lyophilization (masse=28 mg, yield=48%).

$^1H$ NMR (400 MHz, $CDCl_3$) δ 7.65 (d, J=4.2 Hz, 1H), 7.63-7.59 (m, 2H), 7.31-7.23 (m, 3H), 7.11 (d, J=4.2 Hz, 2H), 4.14 (t, J=7.1 Hz, 2H), 3.52 (t, J=4.6 Hz, 4H), 2.33-2.25 (m, 6H), 1.88 (quin, J=7.1 Hz, 2H). $^{13}C$ NMR (101 MHz, $CDCl_3$) δ 160.1, 139.7, 136.1, 134.0, 129.5, 128.7, 128.4, 127.4, 66.9, 56.1, 53.4, 51.2, 25.0.

LC/MS (M+H)=300.16

2-(4-(benzyl(methyl)amino)butyl)-4-phenylpyridazin-3(2H)-one 10a

Using the same procedure described for 10d and starting from 2-(4-chlorobutyl)-4-phenylpyridazin-3(2H)-one 4a (37 mg, 0.14 mmol, 1 equiv.) and N-methylbenzylamine (25.6 mg, 27.2 μL, 0.21 mmol, 2 equiv.), NaI (2.1 mg, 0.014 mmol, 0.1 equiv), $Na_2CO_3$ (22.3 mg, 0.21 mmol, 1.5 equiv.), the title compound 10a was obtained after salification and lyophilization (masse=64 mg, yield=57%).

$^1H$ NMR (400 MHz, $CDCl_3$) δ 7.65-7.58 (m, 3H), 7.29-7.20 (m, 3H), 7.16-7.03 (m, 6H), 4.08 (t, J=7.2 Hz, 2H), 3.30 (s, 2H), 2.25 (t, J=7.2 Hz, 2H), 2.00 (s, 3H), 1.72 (q, J=7.3 Hz, 2H), 1.43 (q, J=7.3 Hz, 2H).

$^{13}C$ NMR (101 MHz, $CDCl_3$) δ 160.1, 139.8, 139.1, 136.2, 134.2, 129.6, 129.2, 128.9, 128.5, 128.4, 127.5, 127.0, 62.5, 57.1, 52.6, 42.2, 26.4, 24.7

LC/MS (M+H)=348.2

2-(4-(1,4-oxazepan-4-yl)butyl)-4-phenylpyridazin-3(2H)-one 10c

Using the same procedure described for 10d and starting from 2-(4-chlorobutyl)-4-phenylpyridazin-3(2H)-one 4a (90 mg, 0.32 mmol, 1 equiv.) and 1,4-oxazepane (69.3 mg, 0.65 mmol, 2 equiv.), NaI (4.9 mg, 0.032 mmol, 0.1 equiv.), $K_2CO_3$ (90.0 mg, 0.65 mmol, 2.0 equiv.), the title compound was obtained after salification and lyophilization (masse=70 mg, yield=59%).

$^1H$ NMR (400 MHz, $CDCl_3$) δ 7.83 (d, J=4.2 Hz, 1H), 7.81-7.75 (m, 2H), 7.48-7.39 (m, 3H), 7.28 (d, J=4.2 Hz, 1H), 4.27 (t, J=7.4 Hz, 2H), 3.79 (t, J=6.1 Hz, 2H), 3.75-3.70 (m, 2H), 2.73-2.67 (m, 4H), 2.59-2.53 (m, 2H), 1.94-1.84 (m, 4H), 1.64-1.52 (m, 2H)$^{13}C$ NMR (101 MHz, $CDCl_3$) δ 160.0, 139.7, 136.1, 134.0, 129.5, 128.7, 128.4, 127.4, 69.1, 68.7, 57.8, 57.6, 53.8, 52.4, 29.7, 26.3, 24.7.

LC/MS (M+H)=328.19

4-phenyl-2-(4-(piperidin-1-yl)butyl)pyridazin-3(2H)-one 10d

Using the same procedure described for 10d and starting from 2-(4-chlorobutyl)-4-phenylpyridazin-3(2H)-one 4a (125 mg, 0.38 mmol, 1 equiv.) and piperidine (129.6 mg, 1.52 mmol, 4 equiv.), NaI (5.7 mg, 0.038 mmol, 0.1 equiv.), $K_2CO_3$ (105.2 mg, 0.76 mmol, 2.0 equiv.), the title compound was obtained after salification and lyophilization (masse=95 mg, yield=80%).

$^1H$ NMR (400 MHz, $CDCl_3$) δ 7.62 (d, J=4.2 Hz, 1H), 7.80-7.75 (m, 2H), 7.47-7.38 (m, 3H), 7.27 (d, J=4.2 Hz, 1H), 4.26 (t, J=7.4 Hz, 2H), 2.49-2.32 (m, 6H), 1.87 (quin, J=7.5 Hz, 2H), 1.66-1.54 (m, 6H), 1.47-1.39 (m, 2H). $^{13}C$ NMR (101 MHz, $CDCl_3$) δ 160.0, 140.4, 136.1, 134.0, 129.5, 128.7, 128.4, 127.4, 58.9, 54.5, 52.4, 26.5, 25.7, 24.3, 23.9.

LC/MS (M+H)=312.20

2-(4-(azepan-1-yl)butyl)-4-phenylpyridazin-3(2H)-one 10e

Using the same procedure described for 10d and starting from 2-(4-chlorobutyl)-4-phenylpyridazin-3(2H)-one 4a (80 mg, 0.30 mmol, 1 equiv.) and azepane (60.4 mg, 0.6 mmol, 2 equiv.), NaI (4.6 mg, 0.030 mmol, 0.1 equiv.), $Na_2CO_3$ (48.4 mg, 0.46 mmol, 1.5 equiv.), the title compound was obtained after salification and lyophilization (masse=96.6 mg, yield=88%).

LC/MS (M+H)=326.18

2-(4-(azocan-1-yl)butyl)-4-phenylpyridazin-3(2H)-one 10f

Using the same procedure described for 10d and starting from 2-(4-chlorobutyl)-4-phenylpyridazin-3(2H)-one 4a (90 mg, 0.32 mmol, 1 equiv.) and azocane (73.7 mg, 0.65 mmol, 2 equiv.), NaI (4.9 mg, 0.03 mmol, 0.1 equiv.), $K_2CO_3$ (90.0 mg, 0.65 mmol, 2.0 equiv.), the title compound was obtained after salification and lyophilization (masse=106.2 mg, yield=96%).

$^1H$ NMR (400 MHz, $CDCl_3$) δ 7.82 (d, J=4.2 Hz, 1H), 7.80-7.76 (m, 2H), 7.47-7.38 (m, 3H), 7.27 (d, 1H, J=4.2 Hz), 4.26 (t, J=7.4 Hz, 2H), 2.59-2.53 (m, 4H), 2.50 (t, J=7.1 Hz, 2H), 1.9 (quin, J=7.4 Hz, 2H), 1.65-1.48 (m, 12H). $^{13}C$ NMR (101 MHz, $CDCl_3$) δ 160.1, 139.7, 136.1, 134.1, 129.5, 128.7, 128.4, 127.4, 58.3, 53.9, 52.5, 27.7, 27.2, 26.3, 26.2, 25.2.

LC/MS (M+H)=320.24

2-(4-(3,4-dihydroisoquinolin-2(1H)-yl)butyl)-4-phenylpyridazin-3(2H)-one 10g

Using the same procedure described for 10d and starting from 2-(4-chlorobutyl)-4-phenylpyridazin-3(2H)-one 4a (80 mg, 0.30 mmol, 1 equiv.) and 1,2,3,4-tetrahydroisoquinoline (81.1 mg, 0.61 mmol, 2 equiv.), NaI (4.6 mg, 0.03 mmol, 0.1 equiv.), $Na_2CO_3$ (48.4 mg, 0.46 mmol, 1.5 equiv.), the title compound was obtained as a beige solid after salification and lyophilization (masse=40.0 mg, yield=33%).

$^1H$ NMR (400 MHz, $CDCl_3$) δ 7.82 (d, J=4.2 Hz, 1H), 7.81-7.77 (m, 2H), 7.47-7.39 (m, 3H), 7.27 (d, J=4.2 Hz, 1H), 7.14-7.06 (m, 3H), 7.04-6.98 (m, 1H), 4.3 (t, J=7.4 Hz, 2H), 3.64 (s, 2H), 2.9 (t, J=5.8 Hz, 2H), 2.73 (t, J=5.8 Hz, 2H), 2.58 (t, J=7.6 Hz, 2H), 1.95 (quin, J=7.5 Hz, 2H), 1.70 (m, J=7.5 Hz, 2H).

$^{13}C$ NMR (101 MHz, $CDCl_3$) δ 160.1, 139.8, 136.2, 134.8, 134.4, 134.1, 129.6, 128.8, 128.7, 128.5, 127.5, 126.7, 126.2, 125.7, 58.0, 56.2, 52.5, 51.0, 29.1, 26.5, 24.4.

LC/MS (M+H)=360.17

4-phenyl-2-(4-(1,2,4,5-tetrahydro-3H-benzo[d]azepin-3-yl)butyl)pyridazin-3(2H)-one 10h Using the same procedure described for 10d and starting from 2-(4-chlorobutyl)-4-phenylpyridazin-3(2H)-one 4a (80 mg, 0.30 mmol, 1 equiv.) and 1,2,3,4-tetrahydroisoquinoline (89.7 mg, 0.61 mmol, 2 equiv.), NaI (4.6 mg, 0.03 mmol, 0.1 equiv.), $Na_2CO_3$ (48.4 mg, 0.46 mmol, 1.5 equiv.), the title compound was obtained as an off white solid after salification and lyophilization (masse=85.0 mg, yield=68%).

$^1H$ NMR (400 MHz, $CDCl_3$) δ 7.82 (d, J=4.2 Hz, 1H), 7.81-7.76 (m, 2H), 7.48-7.39 (m, 3H), 7.27 (d, J=4.2 Hz, 1H), 7.13-7.06 (m, 4H), 4.28 (t, J=7.4 Hz, 2H), 2.91 (dd,

J=6.4 Hz, J=3.8 Hz, 4H), 2.64 (d, J=6.4 Hz, 4H), 2.57-2.51 (m, 2H), 1.9 (quin, J=7.5 Hz, 2H), 1.67-1.57 (m, 2H)

$^{13}$C NMR (101 MHz, $CDCl_3$) δ 160.1, 142.3, 139.8, 136.2, 134.1, 129.6, 128.9, 128.8, 128.5, 127.5, 126.3, 58.7, 55.5, 52.6, 36.6, 26.6, 24.2.

LC/MS (M+H)=374.18

2-(4-(adamantan-1-ylamino)butyl)-4-phenylpyridazin-3(2H)-one 10i

Using the same procedure described for 10d and starting from 2-(4-chlorobutyl)-4-phenylpyridazin-3(2H)-one 4a (80 mg, 0.30 mmol, 1 equiv.) and 1-adamantylamine (69.1 mg, 0.46 mmol, 1.5 equiv.), NaI (4.6 mg, 0.03 mmol, 0.1 equiv.), $Na_2CO_3$ (48.4 mg, 0.46 mmol, 1.5 equiv.), the title compound was obtained as a beige solid after salification and lyophilization (masse=63.7 mg, yield=51%).

$^1$H NMR (400 MHz, $CDCl_3$) δ 7.81 (d, J=4.2 Hz, 1H), 7.75-7.67 (m, 2H), 7.44-7.37 (m, 3H), 7.26 (d, J=4.2 Hz, 1H), 4.22 (t, J=7.3 Hz, 2H), 3.00-2.91 (m, 3H), 2.6 (t, J=7.6 Hz, 2H), 2.07-1.97 (m, 4H), 1.86 (q, J=7.6 Hz, 2H), 1.69-1.45 (m, 18H).

LC/MS (M+H)=378.21

2-(4-(adamantan-1-yl(methyl)amino)butyl)-4-phenylpyridazin-3(2H)-one 10j

Using the same procedure described for 10d and starting from 2-(4-chlorobutyl)-4-phenylpyridazin-3(2H)-one 4a (80 mg, 0.30 mmol, 1 equiv.) and N-methyladamantyl1-amine (119.5 mg, 0.72 mmol, 2.5 equiv.), NaI (3.7 mg, 0.03 mmol, 0.1 equiv.), $K_2CO_3$ (80.0 mg, 0.58 mmol, 2.0 equiv.), the title compound was obtained as a beige solid after salification and lyophilization (masse=63.7 mg, yield=51%).

$^1$H NMR (400 MHz, $CDCl_3$) δ 7.28 (d, J=4.2 Hz, 1H), 7.80-7.75 (m, 2H), 7.47-7.37 (m, 3H), 7.27 (d, J=4.2 Hz, 1H), 4.27 (t, J=7.4 Hz, 2H), 2.60-2.43 (m, 2H), 2.28 (s, 3H), 2.12-2.05 (m, 3H), 1.88 (quin, J=7.4 Hz, 2H), 1.80-1.68 (m, 6H), 1.68-1.53 (m, 8H).

$^{13}$C NMR (101 MHz, $CDCl_3$) δ 160.0, 139.7, 136.2, 134.0, 129.4, 128.7, 128.3, 127.4, 52.4, 48.9, 38.2, 36.7, 33.5, 29.6, 26.3.

LC/MS (M+H)=392.19

4-phenyl-2-(4-(1,3,3-trimethyl-6-azabicyclo[3.2.1]octan-6-yl)butyl)pyridazin-3(2H)-one, 10k Using the same procedure described for 10d and starting from 2-(4-chlorobutyl)-4-phenylpyridazin-3(2H)-one 4a (80 mg, 0.30 mmol, 1 equiv.) and 1,3,3-trimethyl-6-azabicyclo[3.2.1]octane (88.7 mg, 0.58 mmol, 2.0 equiv.), NaI (4.3 mg, 0.03 mmol, 0.1 equiv.), $K_2CO_3$ (80.0 mg, 0.58 mmol, 2.0 equiv.), the title compound was obtained after salification and lyophilization (masse=71.0 mg, yield=65%).

$^1$H NMR (400 MHz, $CDCl_3$) δ 7.82 (d, J=4.2 Hz, 1H), 7.81-7.77 (m, 2H), 7.47-7.38 (m, 3H), 7.27 (d, J=4.2 Hz, 1H), 4.25 (t, J=7.4 Hz, 2H), 3.06-3.00 (m, 1H), 2.89 (d, J=9.6 Hz, 1H), 2.64 (dt, J=11.3 Hz, J=7.0 Hz), 2.49 (dt, J=11.3 Hz, J=7.0 Hz, 1H), 2.07 (d, J=9.5 Hz, 1H), 1.91 (tt, J=8.0 Hz, J=7.0 Hz), 1.60-1.43 (m, 4H), 1.34 (AB, J=14.0 Hz, 1H), 1.21 (s, 3H), 1.18-1.01 (m, 2H), 0.99 (s, 3H), 0.86 (s, 3H).

$^{13}$C NMR (101 MHz, $CDCl_3$) δ 160.0, 139.6, 136.0, 134.1, 129.4, 128.7, 128.3, 127.3, 65.1, 62.4, 57.4, 52.5, 52.1, 45.0, 41.6, 41.2, 36.8, 32.1, 30.1, 26.7, 26.1, 25.9.

LC/MS (M+H)=380.22

8-(4-(6-oxo-5-phenylpyridazin-1(6H)-yl)butyl)-8-azabicyclo[3.2.1]octan-3-one 101

Using the same procedure described for 9b and starting from 2-(4-chlorobutyl)-4-phenylpyridazin-3(2H)-one 4a (80 mg, 0.30 mmol, 1 equiv.) and 1,3,3-trimethyl-6-azabicyclo[3.2.1]octane hydrochloride (59.1 mg, 0.58 mmol, 2.0 equiv.), NaI (4.6 mg, 0.03 mmol, 0.1 equiv.), $Na_2CO_3$ (48.4 mg, 0.46 mmol, 1.5 equiv.), the title compound was obtained as an orange gum (masse=60.0 mg, yield=56%).

$^{13}$C NMR (101 MHz, $CDCl_3$) δ 7.83 (d, J=4.2 Hz, 1H), 7.80-7.75 (m, 2H), 7.46-7.38 (m, 3H), 7.28 (d, J=4.2 Hz, 1H), 4.3 (t, J=7.3 Hz, 2H), 3.56-3.47 (m, 2H), 2.67-2.57 (m, 4H), 2.17 (d, J=16.0 Hz, 2H), 2.05-1.901 (m, 4H), 1.64 (quin, J=7.6 Hz, 2H), 1.57 (q, 2H, J=7.4 Hz).

$^{13}$C NMR (101 MHz, $CDCl_3$) δ 210.3, 160.2, 139.9, 136.3, 134.1, 129.7, 128.8, 128.5, 127.5, 58.7, 52.4, 49.9, 47.5, 27.9, 26.4, 26.3.

LC/MS (M+H)=352.2

2-(4-(benzyl((tetrahydrofuran-2-yl)methyl)amino)butyl)-4-phenylpyridazin-3(2H)-one 10m N-benzyl-1-(tetrahydrofuran-2-yl)methanamine was prepared from benzaldehyde and tetrahydro-drofurfuryl amine by reductive amination according to literature procedure.[3]

[3(a)] Fujikura, T. *Chem. Pharm. Bull.* 1996, 44, 1865.

[3(b)] Shah, R. D. *J. Org. Chem.*, 1996, 61, 3849.

[3(c)] For analytical characteristics see, Kakiuchi, K., *J. Org. Chem.*, 2017, 82, 6748-6763.

Using the same procedure described for 10d and starting from 2-(4-chlorobutyl)-4-phenylpyridazin-3(2H)-one 4a (80 mg, 0.30 mmol, 1 equiv.) and N-benzyl-1-(tetrahydrofuran-2-yl)methanamine (116.5 mg, 0.61 mmol, 2.0 equiv.), NaI (4.6 mg, 0.03 mmol, 0.1 equiv.), $Na_2CO_3$ (48.4 mg, 0.46 mmol, 1.5 equiv.) in a mixture of MeCN (2.0 mL)-DMF (0.3 mL), the title compound was obtained after salification and lyophilization (masse=71.0 mg, yield=51%).

$^1$H NMR (400 MHz, $CDCl_3$) δ 7.79 (d, J=4.2 Hz, 1H), 7.79-7.77 (m, 2H), 7.46-7.39 (m, 3H), 7.34-7.27 (m, 4H), 7.26 (d, J=4.2 Hz, 1H), 7.22-7.18 (m, 1H), 4.22 (t, J=7.2 Hz, 2H), 3.99 (quin, J=6.2 Hz, 1H), 3.79 (dt, J=8.3 Hz, J=6.8 Hz, 1H), 3.74-3.66 (m, 2H), 3.55 (d, J=14.2 Hz, 1H), 2.62-2.43 (m, 4H), 1.96-1.76 (m, 5H), 1.56 (quin, J=7.7 Hz, 2H), 1.1-1.06 (m, 1H) $^{13}$C NMR (101 MHz, $CDCl_3$) δ 160.1, 139.7, 137.9, 136.2, 134.2, 129.6, 129.0, 128.8, 128.5, 128.2, 127.5, 126.9, 77.9, 68.0, 59.4, 58.3, 54.2, 52.6, 30.3, 26.3, 25.5, 24.4.

LC/MS (M+H)=418.21

2-(4-((2-methoxy-1-phenylethyl)amino)butyl)-4-phenylpyridazin-3(2H)-one 10n 2-methoxy-1-phenylethan-1-amine Commercially available 2-methoxy-1-phenylethan-1-one (200 mg, 1.26 mmol, 1 equiv.) was dissolved in dry EtOH (5 mL). Titanium tetraisopropanolate (741 mg, 0.77 mL, 2.53 mmol, 2 equiv.) was added followed by 7M $NH_3$ (0.90 mL, 6.33 mmol, 5 equiv.) and the resulting mixture was stirred overnight. $NaBH_4$ (86.2 mg, 2.27 mmol, 1.8 equiv.) was then added portionwise and stirred at room temperature overnight. Progress of the reaction was monitored by HPLC. The mixture was quenched with aqueous $NH_3$ (6 mL) leading to precipitation. The precipitate was filtered and washed with $H_2O$ (10 mL), and EtOAc (2×20 mL). The layers were separated and the aqueous phase was extracted with EtOAc (20 mL). The combined organic phases were dried over $Na_2SO_4$, filtered and evaporated to yield a yellow gum (masse=191 mg, purity~70%). The crude was used without further purification.

$^1$H NMR (400 MHz, $CDCl_3$) δ 7.39-7.29 (m, 5H), 4.19 (dd, J=8.7 Hz, J=4.0 Hz), 3.51 (dd, J=9.2 Hz, J=3.9 Hz), 3.38 (s, 3H), 3.40-3.35 (m, 1H). $^{13}$C NMR (101 MHz, $CDCl_3$) δ 142.5, 128.5, 127.5, 126.9, 78.9, 59.0, 55.5.

Using the same procedure described for 10d and starting from 2-(4-chlorobutyl)-4-phenylpyridazin-3(2H)-one 4a (80 mg, 0.30 mmol, 1 equiv.) and 2-methoxy-1-phenylethan-1-amine (146.2 mg, 0.61 mmol, 2.0 equiv.), NaI (4.6 mg, 0.03 mmol, 0.1 equiv.), $Na_2CO_3$ (48.6 mg, 0.46 mmol, 1.5 equiv.), the title compound was obtained as a beige solid after salification and lyophilization (masse=45.0 mg, yield=36%).

$^1$H NMR (400 MHz, $CDCl_3$) 7.79 (d, J=4.2 Hz, 1H), 7.80-7.76 (m, 2H), 7.47-7.40 (m, 3H), 7.37-7.29 (m, 4H), 7.27-7.23 (m, 2H), 4.22 (t, J=7.3 Hz, 1H), 3.46-3.36 (m, 2H), 3.35 (s, 3H), 2.50 (qt, J=12.2 Hz, J=7.1 Hz, 2H), 1.96-1.80 (m, 3H), 1.56 (quin, J=7.5 Hz, 2H). $^{13}$C NMR (101 MHz, $CDCl_3$) δ 160.1, 140.9, 139.8, 136.2, 134.2, 129.6, 128.9, 128.5, 128.4, 127.7, 127.5, 127.4, 77.9, 63.1, 59.0, 52.7, 47.4, 27.6, 26.3.

LC/MS (M+H)=378.17

2-(4-((2-methoxy-1-phenylethyl)(methyl)amino)butyl)-4-phenylpyridazin-3(2H)-one 10o

2-methoxy-N-methyl-1-phenylethan-1-amine

Using the same procedure described for the preparation of 2-methoxy-1-phenylethan-1-amine and starting from 2-methoxy-1-phenylethan-1-one (500 mg, 0.46 mL, 3.33 mmol) and $NH_2Me$ (5 equiv) the title compound was obtained as a yellow oil (m=90 mg, 16%).

$^1$H NMR (400 MHz, $CDCl_3$) δ 7.39-7.29 (m, 5H), 3.67 (dd, J=9.1 Hz, J=3.9 Hz), 3.37 (dd, J=9.2 Hz, J=3.9 Hz, 1H) 2.21 (s, 3H), 1.90 (bs, 1H)

Using the same procedure described for 10d and starting from 2-(4-chlorobutyl)-4-phenylpyridazin-3(2H)-one 4a (65 mg, 0.23 mmol, 1 equiv.) and 2-methoxy-N-methyl-1-phenylethan-1-amine (73.8 mg, 0.45 mmol, 1.9 equiv.), NaI (3.5 mg, 0.02 mmol, 0.1 equiv.), $K_2CO_3$ (64.9 mg, 0.47 mmol, 2.0 equiv.), the title compound was obtained after salification and lyophilization (masse=31.0 mg, yield=34%).

$^1$H NMR (400 MHz, $CDCl_3$) δ 7.81 (d, J=4.2 Hz, 1H), 7.80-7.76 (m, 2H), 7.47-7.39 (m, 3H), 7.34-7.22 (m, 6H), 4.23 (t, J=7.3 Hz, 2H), 3.81-3.75 (m, 1H), 3.72-3.67 (m, 1H), 3.59-3.57 (m, 1H), 3.32 (s, 3H), 2.55-2.30 (m, 2H), 2.22 (s, 3H), 1.84-1.82 (m, 2H), 1.56 (quin, J=7.9 Hz, 2H).

$^{13}$C NMR (101 MHz, $CDCl_3$) δ 160.0, 139.6, 136.0, 134.0, 129.5, 128.7, 128.5, 128.4, 128.1, 127.4, 127.2, 74.2, 67.6, 58.9, 54.2, 52.5, 38.8, 26.1; 24.4.

LC/MS (M+H)=392.23

2-(4-((2-hydroxyethyl)(methyl)amino)butyl)-4-phenylpyridazin-3(2H)-one 10p

Using the same procedure described for 10d and starting from 2-(4-chlorobutyl)-4-phenylpyridazin-3(2H)-one 4a (80 mg, 0.30 mmol, 1 equiv.) and 2-methylaminoethanol (45.7 mg, 0.61 mmol, 2.0 equiv.), NaI (4.6 mg, 0.03 mmol, 0.1 equiv.), $Na_2CO_3$ (48.5 mg, 0.46 mmol, 1.5 equiv.), the title compound was obtained as a beige solid after salification and lyophilization (masse=76.0 mg, yield=74%).

$^1$H NMR (400 MHz, $CDCl_3$) δ 7.83 (d, J=4.2 Hz, 1H), 7.81-7.76 (m, 2H), 7.46-7.38 (m, 3H), 7.26 (d, J=4.2 Hz, 1H), 4.27 (t, J=7.5 Hz, 2H), 3.59 (t, J=5.3 Hz, 2H), 3.12-3.03 (bs, 1H), 2.53 (t, J=5.4 Hz, 2H), 2.48 (t, J=7.3 Hz, 2H), 2.25 (s, 3H), 1.89 (quin; J=7.6 Hz, 2H), 1.58 (quin, J=7.4 Hz, 2H). $^{13}$C NMR (101 MHz, $CDCl_3$) δ 160.1, 139.8, 136.3, 134.0, 129.6, 128.8, 128.5, 127.6, 59.1, 58.5, 57.1, 52.4, 41.6, 26.1, 24.3.

LC/MS (M+H)=302.18

2-(4-(methyl((tetrahydro-2H-pyran-4-yl)methyl)amino)butyl)-4-phenylpyridazin-3(2H)-one 10q Using the same procedure described for 10d and starting from 2-(4-chlorobutyl)-4-phenylpyridazin-3(2H)-one 4a (80 mg, 0.30 mmol, 1 equiv.) and N-methyl-1-(tetrahydro-2H-pyran-4-yl)methanamine (74.8 mg, 0.58 mmol, 1.9 equiv.), NaI (4.3 mg, 0.03 mmol, 0.1 equiv.), $K_2CO_3$ (79.6 mg, 0.47 mmol, 2.0 equiv.), the title compound was obtained after salification and lyophilization (masse=36.0 mg, yield=35%).

$^1$H NMR (400 MHz, $CDCl_3$) δ 7.81 (d, J=4.2 Hz, 1H), 7.80-7.75 (m, 2H), 7.48-7.37 (m, 3H), 7.27 (d, J=4.2 Hz, 1H), 4.25 (t, J=7.3 Hz, 2H), 3.95 (ddd, J=11.8 Hz, J=10.9 Hz, J=4.4 Hz, 2H), 3.41-3.32 (m, 2H), 2.48 (d, J=6.8 Hz, 1H), 2.35 (t, J=7.4 Hz, 2H), 2.17 (s, 3H), 2.16-2.13 (m, 2H), 1.91-1.82 (m, 2H), 1.77-1.62 (m, 2H), 1.53 (quin, J=7.4 Hz, 2H), 1.35-1.15 (m, 2H).

LC/MS (M+H)=356.21

4-phenyl-2-(4-(3-phenylpiperidin-1-yl)butyl)pyridazin-3(2H)-one 10r

Using the same procedure described for 10d and starting from 2-(4-chlorobutyl)-4-phenylpyridazin-3(2H)-one 4a (80 mg, 0.30 mmol, 1 equiv.) and 3-phenylpiperidine (98.2 mg, 0.60 mmol, 2.0 equiv.), NaI (4.6 mg, 0.30 mmol, 0.1 equiv.), $K_2CO_3$ (84.2 mg, 0.60 mmol, 2.0 equiv.), the title compound was obtained after salification and lyophilization (masse=81.0 mg, yield=69%).

$^1$H NMR (400 MHz, $CDCl_3$) δ 7.80 (d, J=4.2 Hz, 1H), 7.79-7.75 (m, 2H), 7.46-7.39 (m, 3H), 7.32-7.17 (m, 6H), 4.26 (t, J=7.2 Hz, 2H), 3.00 (t, J=12.9 Hz, 2H), 2.87-2.76 (m, 1H), 2.42 (ddd, J=9.2 Hz, J=6.2 Hz, J=1.8 Hz, 2H), 2.01-1.83 (m, 5H), 1.81-1.67 (m, 2H), 1.66-1.57 (m, 2H), 1.45 (qd, J=12.4 Hz, J=4.6 Hz, 1H). $^{13}$C NMR (101 MHz, $CDCl_3$) δ 160.0, 144.7, 139.6, 134.0, 129.5, 128.7, 128.4, 127.4, 127.2, 126.3, 61.3, 58.7, 53.9, 52.5, 42.9, 31.6, 26.5, 25.8, 24.1.

LC/MS (M+H)=388.22

4-phenyl-2-(4-(4-phenylpiperidin-1-yl)butyl)pyridazin-3(2H)-one 10s

Using the same procedure described for 10d and starting from 2-(4-chlorobutyl)-4-phenylpyridazin-3(2H)-one 4a (80 mg, 0.30 mmol, 1 equiv.) and 4-phenylpiperidine (39.28 mg, 0.30 mmol, 1.0 equiv.), NaI (3.6 mg, 0.03 mmol, 0.1 equiv.), $K_2CO_3$ (84.2 mg, 0.60 mmol, 2.0 equiv.), the title compound was obtained after salification and lyophilization (masse=81.0 mg, yield=69%).

$^1$H NMR (400 MHz, $CDCl_3$) δ 7.83 (d, J=4.2 Hz, 1H), 7.81-7.76 (m, 2H), 7.49-7.39 (m, 3H), 7.32-7.16 (m, 6H), 4.29 (t, J=7.2 Hz, 2H), 3.1 (dq, J=11.2 Hz, J=2.8 Hz, 2H), 2.56-2.45 (m, 3H), 2.15-2.05 (m, 2H), 1.96-1.81 (m, 6H), 1.72-1.61 (m, 2H). $^{13}$C NMR (101 MHz, $CDCl_3$) δ160.0, 146.1, 139.7, 136.2, 134.0, 129.5, 128.7, 128.4, 128.3, 127.4, 126.9, 126.2, 58.5, 54.3, 52.3, 42.6, 33.2, 26.4, 24.0.

LC/MS (M+H)=388.23

2-(4-(3-(hydroxymethyl)piperidin-1-yl)butyl)-4-phenylpyridazin-3(2H)-one 10t

Using the same procedure described for 10d and starting from 2-(4-chlorobutyl)-4-phenylpyridazin-3(2H)-one 4a (80 mg, 0.30 mmol, 1 equiv.) and piperidin-3-ylmethanol (70.1 mg, 0.61 mmol, 1.0 equiv.), NaI (3.6 mg, 0.03 mmol, 0.1 equiv.), $K_2CO_3$ (84.2 mg, 0.60 mmol, 2.0 equiv.), the title compound was obtained after salification and lyophilization (masse=94.0 mg, yield=83%).

$^1$H NMR (400 MHz, $CDCl_3$) δ 7.82 (d, J=4.2 Hz, 1H), 7.80-7.76 (m, 2H), 7.47-7.38 (m, 3H), 7.27 (d, J=4.2 Hz, 1H), 4.26 (t, J=7.3 Hz, 2H), 3.62 (dd, J=10.5 Hz, J=5.3 Hz, 1H), 3.53 (dd, J=10.5 Hz, J=6.0 Hz, 1H), 2.82-2.76 (m, 1H), 2.68-2.55 (m, 2H), 2.38 (dd, J=8.8 Hz, J=6.9 Hz, 2H), 2.20-2.00 (m, 2H), 1.87 (quin, J=7.2 Hz, 2H), 1.83-1.73 (m, 2H), 1.72-1.52 (m, 4H), 1.20-1.08 (m, 1H). $^{13}$C NMR (101 MHz, $CDCl_3$) δ 160.0, 139.7, 136.2, 134.0, 129.5, 128.7, 128.4, 127.4, 67.1, 58.6, 57.4, 54.3, 52.4, 37.8, 27.6, 26.4, 24.5, 23.9.

LC/MS (M+H)=342.20

2-(4-(2-(2-hydroxyethyl)piperidin-1-yl)butyl)-4-phenylpyridazin-3(2H)-one 10u

Using the same procedure described for 10d and starting from 2-(4-chlorobutyl)-4-phenylpyridazin-3(2H)-one 4a (80 mg, 0.30 mmol, 1 equiv.) and 2-piperidineethanol (75.3 mg, 0.6 mmol, 2.0 equiv.), NaI (4.3 mg, 0.03 mmol, 0.1 equiv.), $K_2CO_3$ (80.0 mg, 0.57 mmol, 2.0 equiv.), the title compound was obtained after salification and lyophilization (masse=44.0 mg, yield=45%).

$^1$H NMR (400 MHz, $CDCl_3$) δ 7.82 (d, J=4.2 Hz, 1H), 7.80-7.75 (m, 2H), 7.46-7.38 (m, 3H), 7.27 (d, J=4.2 Hz, 1H), 4.26 (t, J=7.3 Hz, 2H), 3.87 (ddd, J=10.8 Hz, J=6.6 Hz, J=4.4 Hz, 1H), 3.72 (ddd, J=10.8 Hz, J=7.4 Hz, J=4.2 Hz, 1H), 3.05 (ddd, J=12.7 Hz, J=7.1 Hz, J=2.9 Hz, 1H), 2.88 (ddd, J=12.8 Hz, J=9.0 Hz, J=6.7 Hz, 1H), 2.73-2.66 (m, 1H), 2.55 (ddd, J=12.8 Hz, J=9.1 Hz, J=5.8 Hz, 1H), 2.35-2.27 (m, 1H), 1.93-1.78 (m, 3H), 1.72-1.63 (m, 3H), 1.62-1.51 (m, 3H), 1.48-1.35 (m, 3H). $^{13}$C NMR (101 MHz, $CDCl_3$) δ 160.0, 139.6, 136.2, 134.0, 129.5, 128.7, 128.4, 127.5, 61.9, 52.6, 52.2, 49.5, 31.6, 27.3, 26.2, 24.1, 22.6, 22.5.

LC/MS (M+H)=356.22

4-phenyl-2-(4-(3-phenylmorpholino)butyl)pyridazin-3(2H)-one 10v

Using the same procedure described for 10d and starting from 2-(4-chlorobutyl)-4-phenylpyridazin-3(2H)-one 4a (80 mg, 0.30 mmol, 1 equiv.) and 3-phenylmorpholine (85.0 mg, 0.52 mmol, 1.8 equiv.), NaI (4.3 mg, 0.03 mmol, 0.1 equiv.), $K_2CO_3$ (80.0 mg, 0.57 mmol, 2.0 equiv.), the title compound was obtained after salification and lyophilization (masse=50.0 mg, yield=39%).

$^1$HNMR (400 MHz, $CDCl_3$) δ 7.82-7.72 (m, 3H), 7.46-7.38 (m, 3H), 7.37-7.21 (m, 5H), 7.25 (d, J=4.2 Hz, 1H), 4.16 (t, J=7.4 Hz, 2H), 3.95-3.88 (m, 1H), 3.78-3.65 (m, 2H), 3.37 (t, J=11.3 Hz, 1H), 3.26 (dd, J=9.9 Hz, J=3.2 Hz, 1H), 2.97 (dt, J=11.6 Hz, J=2.0 Hz, 1H), 2.57-2.46 (m, 1H), 2.3 (td, J=11.8 Hz, J=3.1 Hz, 1H), 2.02-1.95 (m, 1H), 1.90-1.77 (m, 1H), 1.73-1.61 (m, 1H), 1.57-1.42 (m, 2H).

$^{13}$C NMR (101 MHz, $CDCl_3$) δ 159.9, 139.6, 136.0, 134.0, 129.5, 128.7, 128.5, 128.4, 128.2, 127.6, 127.3, 73.5, 67.7, 67.5, 54.3, 52.5, 51.7, 26.0, 23.4.

LC/MS (M+H)=390.21

4-phenyl-2-(4-(2-phenylmorpholino)butyl)pyridazin-3(2H)-one 10w

Using the same procedure described for 10d and starting from 2-(4-chlorobutyl)-4-phenylpyridazin-3(2H)-one 4a (80 mg, 0.30 mmol, 1 equiv.) and 3-phenylmorpholine (85.0 mg, 0.52 mmol, 1.8 equiv.), NaI (4.3 mg, 0.03 mmol, 0.1 equiv.), $K_2CO_3$ (80.0 mg, 0.57 mmol, 2.0 equiv.), the title compound was obtained after salification and lyophilization (masse=71.0 mg, yield=63%).

$^1$H NMR (400 MHz, $CDCl_3$) δ 7.82 (d, J=4.2 Hz, 1H), 7.81-7.75 (m, 2H), 7.48-7.41 (m, 3H), 7.39-7.31 (m, 4H), 7.30-7.25 (m, 1H), 7.28 (d, J=4.2 Hz, 1H), 4.56 (dd, J=10.0 Hz, J=2.4 Hz, 1H), 4.26 (t, J=7.2 Hz, 2H), 4.03 (ddd, J=11.4 Hz, J=3.5 Hz, J=1.8 Hz, 1H), 3.84 (td, J=11.7 Hz, J=2.7 Hz, 1H), 2.94 dt, J=11.5 Hz, J=2.1 Hz, 1H), 2.81 (dt, J=11.4 Hz, J=1.9 Hz, 1H), 2.44 (dd, J=8.5 Hz, J=6.6 Hz, 2H), 2.24 (td, J=11.2 Hz, J=3.2 Hz, 1H), 2.06 (t, J=10.9 Hz, 1H), 1.92 (quin, J=7.4 Hz, 2H), 1.82 (quin, J=7.6 Hz, 2H). $^{13}$C NMR (101 MHz, $CDCl_3$) δ 160.0, 140.4, 139.7, 136.1, 134.0, 129.5, 128.7, 128.4, 128.3, 127.7, 127.4, 126.2, 78.2, 67.1, 60.6, 52.9, 52.4, 26.3, 23.7.

LC/MS (M+H)=390.21

2-(4-(2,6-dimethylmorpholino)butyl)-4-phenylpyridazin-3(2H)-one 10x

Using the same procedure described for 10d and starting from 2-(4-chlorobutyl)-4-phenylpyridazin-3(2H)-one 4a (80 mg, 0.30 mmol, 1 equiv.) and 2,6-dimethylmorpholine (58.3 mg, 0.50 mmol, 2.0 equiv.), NaI (3.8 mg, 0.03 mmol, 0.1 equiv.), $K_2CO_3$ (70.0 mg, 0.50 mmol, 2.0 equiv.), the title compound was obtained after salification and lyophilization (masse=61.0 mg, yield=71%).

$^1$H NMR (400 MHz, $CDCl_3$) δ 7.80 (d, J=4.2 Hz, 1H), 7.78-7.73 (m, 2H), 7.45-7.36 (m, 3H), 7.25 (d, J=4.2 Hz, 1H), 4.25 (t, J=7.2 Hz), 3.70-3.60 (m, 2H), 2.72 (dd, J=11.1 Hz, J=1.8 Hz), 2.34 (dd, J=8.5 Hz, J=6.6 Hz), 1.87 (tt, J=8.1 Hz, J=6.8 Hz), 1.67 (t, J=10.7 Hz, 2H), 1.61-1.52 (m, 2H), 1.12 (d, J=6.1 Hz, 6H). $^{13}$C NMR (101 MHz, $CDCl_3$) δ 160.0, 139.7, 136.1, 134.0, 129.5, 128.7, 128.4, 127.4, 71.6, 59.5, 58.2, 52.3, 26.3, 23.7, 19.2.

2-[4-(4-benzylpiperazin-1-yl)butyl]-4-phenyl-2,3-dihydropyridazin-3-one 10z

Using the same procedure described for 10d and starting from 2-(4-chlorobutyl)-4-phenylpyridazin-3(2H)-one 4a (50 mg, 0.19 mmol, 1 equiv.) and 1-benzylpiperazine (67.1 mg, 0.38 mmol, 2.0 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=71.8 mg, yield=94%). Salification and lyophilization led to the corresponding hydrochloride salt.

$^1$H NMR (400 MHz, $CDCl_3$) δ 7.75 (d, J=4.2 Hz, 1H), 7.74-7.70 (m, 2H), 7.41-7.33 (m, 3H), 7.28-7.23 (m, 4H), 7.23-7.15 (m, 1H), 7.20 (d, J=4.2 Hz, 1H), 4.21 (t, J=7.4 Hz, 2H), 3.45 (s, 2H), 2.57-2.30 (m, 8H), 2.34 (t, J=7.7 Hz, 2H), 1.83 (quin, J=7.5 Hz, 2H), 1.53 (quin, J=7.6 Hz, 2H). $^{13}$C NMR (101 MHz, $CDCl_3$) δ 160.0, 139.6, 138.1, 136.1, 134.0, 129.5, 129.2, 128.7, 128.4, 128.2, 127.4, 127.0, 63.0, 58.2, 53.2, 53.0, 52.5, 26.4, 24.1.

LC/MS (M+H)=403.25

2-[4-(4-benzylpiperidin-1-yl)butyl]-4-phenyl-2,3-dihydropyridazin-3-one 11a

Using the same procedure described for 10d and starting from 2-(4-chlorobutyl)-4-phenylpyridazin-3(2H)-one 4a (50 mg, 0.19 mmol, 1 equiv.) and 4-benzylpiperazine (66.7 mg, 0.38 mmol, 2.0 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=59 mg, yield=77%). Salification and lyophilization led to the corresponding hydrochloride salt.

$^1$H NMR (400 MHz, $CDCl_3$) δ 7.81 (d, J=4.2 Hz, 1H), 7.83-7.77 (m, 2H), 7.48-7.40 (m, 3H), 7.32-7.24 (m, 3H), 7.22-7.12 (m, 3H), 4.27 (t, J=7.3 Hz, 2H), 2.31 (dt, J=11.0 Hz, J=3.2 Hz, 2H), 2.53 (d, J=7.1 Hz, 2H), 2.37 (t, J=7.6 Hz, 2H), 1.93-1.80 (m, 4H), 1.71-1.47 (m, 5H), 1.32 (qd, J=12.0 Hz, J=3.2 Hz, 2H). $^{13}$C NMR (101 MHz, $CDCl_3$) δ 160.0, 140.7, 139.6, 136.1, 134.0, 129.5, 129.1, 128.7, 128.4, 128.1, 127.4, 125.7, 58.6, 54.0, 52.5, 43.2, 37.9, 32.1, 26.5, 24.2.

LC/MS (M+H)=402.25

2-{4-[benzyl(ethyl)amino]butyl}-4-phenyl-2,3-dihydropyridazin-3-one 11b

Using the same procedure described for 10d and starting from 2-(4-chlorobutyl)-4-phenylpyridazin-3(2H)-one 4a (50 mg, 0.19 mmol, 1 equiv.) and N-ethylbenzylamine (77.2 mg, 0.57 mmol, 3.0 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=15 mg, yield=22%). Salification and lyophilization led to the corresponding hydrochloride salt.

$^1$H NMR (400 MHz, $CDCl_3$) δ 7.80 (d, J=4.2 Hz, 1H), 7.80-7.76 (m, 2H), 7.47-7.38 (m, 3H), 7.33-7.24 (m, 4H), 7.25 (d, J=4.2 Hz, 1H), 7.23-7.18 (m, 1H), 4.23 (t, J=7.3 Hz, 2H), 3.54 (s, 2H), 2.53-2.44 (m, 4H), 1.86 (quin, J=7.7 Hz, 2H), 1.55 (quin, J=7.4 Hz, 2H), 1.01 (t, J=7.1 Hz, 3H). $^{13}$C NMR (101 MHz, $CDCl_3$) δ 160.1, 140.0, 139.6, 136.1, 134.2, 129.5, 128.8, 128.7, 128.4, 128.1, 127.4, 126.7, 58.1, 52.8, 52.6, 47.2, 26.3, 24.3, 14.2.

LC/MS (M+H)=362.21

2-{4-[cyclohexyl(methyl)amino]butyl}-4-phenyl-2,3-dihydropyridazin-3-one 11c

Using the same procedure described for 10d and starting from 2-(4-chlorobutyl)-4-phenylpyridazin-3(2H)-one 4a (50 mg, 0.19 mmol, 1 equiv.) and N-methylcyclohexylamine (64.6 mg, 0.57 mmol, 3.0 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=43.7 mg, yield=68%). Salification and lyophilization led to the corresponding hydrochloride salt.

$^1$H NMR (400 MHz, $CDCl_3$) δ 7.80 (d, J=4.2 Hz, 1H), 7.79-7.74 (m, 2H), 7.45-7.36 (m, 3H), 7.25 (d, J=4.2 Hz, 1H), 4.25 (t, J=7.5 Hz, 2H), 2.46 (t, J=7.6 Hz, 2H), 2.41-2.29 (m, 2H), 2.22 (s, 3H), 1.85 (quin, J=7.5 Hz, 2H), 1.79-1.68 (m, 4H), 1.64-1.46 (m, 3H), 1.20-1.12 (m, 3H), 1.11-0.99 (m, 1H). $^{13}$C NMR (101 MHz, $CDCl_3$) δ 160.0, 139.6, 136.1, 134.0, 129.4, 128.7, 128.3, 127.4, 62.4, 53.12, 52.5, 37.6, 28.5, 26.4, 26.3, 26.0, 25.1.

LC/MS (M+H)=340.23

4-phenyl-2-[4-(4-phenylpiperazin-1-yl)butyl]-2,3-dihydropyridazin-3-one 11d

Using the same procedure described for 10d and starting from 2-(4-chlorobutyl)-4-phenylpyridazin-3(2H)-one 4a (50 mg, 0.19 mmol, 1 equiv.) and 1-phenylpiperazine (61.7 mg, 0.38 mmol, 2.0 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=57.3 mg, yield=78%). Salification and lyophilization led to the corresponding hydrochloride salt.

$^1$H NMR (400 MHz, $CDCl_3$) δ 7.82 (d, J=4.2 Hz, 1H), 7.81-7.76 (m, 2H), 7.48-7.39 (m, 3H), 7.30-7.22 (m, 3H), 6.96-6.89 (m, 2H), 6.85 (t, J=7.3 Hz, 1H), 4.29 (t, J=7.2 Hz, 2H), 3.22-3.17 (m, 4H), 2.66-2.55 (m, 4H), 2.45 (t, J=7.7 Hz, 2H), 1.92 (quin, J=7.6 Hz, 2H), 1.63 (quin, J=7.6 Hz, 2H). $^{13}$C NMR (101 MHz, $CDCl_3$) δ 160.3, 151.3, 139.7, 136.2, 134.0, 129.5, 129.1, 128.7, 128.4, 127.4, 119.6, 116.0, 58.2, 53.3, 52.4, 49.2, 26.4, 24.1.

LC/MS (M+H)=389.23

2-{4-[(4aR,8aS)-decahydroquinolin-1-yl]butyl}-4-phenyl-2,3-dihydropyridazin-3-one 11e Using the same procedure described for 10d and starting from 2-(4-chlorobutyl)-4-phenylpyridazin-3(2H)-one 4a (50 mg, 0.19 mmol, 1 equiv.) and (4aR,8aS)-decahydroquinoline (47.7 mg, 0.34 mmol, 1.8 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=27.6 mg, yield=40%). Salification and lyophilization led to the corresponding hydrochloride salt.

$^1$H NMR (400 MHz, $CDCl_3$) δ 7.79 (d, J=4.2 Hz, 1H), 7.77-7.72 (m, 2H), 7.44-7.35 (m, 3H), 7.24 (d, J=4.2 Hz, 1H), 4.23 (t, J=7.3 Hz, 1H), 3.02 (d, J=11.4 Hz, 1H), 2.86-2.77 (m, 1H), 2.69-2.58 (m, 1H), 2.31 (t, J=11.4 Hz, 1H), 2.07-1.99 (m, 1H), 1.94-1.69 (m, 6H), 1.65-1.51 (m, 6H), 1.44-1.31 (m, 1H), 1.28-0.89 (m, 6H). $^{13}$C NMR (101 MHz, $CDCl_3$) δ 160.1, 139.7, 136.3, 134.0, 129.5, 128.7, 128.4, 127.5, 66.1, 53.2, 52.1, 51.9, 41.0, 33.1, 32.0, 29.3, 26.4, 25.7, 25.5, 24.7, 21.1.

LC/MS (M+H)=366.25

4-phenyl-2-[4-(thiomorpholin-4-yl)butyl]-2,3-dihydropyridazin-3-one 11u

Using the same procedure described for 10d and starting from 2-(4-chlorobutyl)-4-phenylpyridazin-3(2H)-one 4a (50 mg, 0.19 mmol, 1 equiv.) and tetrahydro-2H-1,4-thiazine (98.2 mg, 0.95 mmol, 5.0 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=55.4 mg, yield=88%). Salification and lyophilization led to the corresponding hydrochloride salt.

$^1$H NMR (400 MHz, $CDCl_3$) δ 7.77 (d, J=4.2 Hz, 1H), 7.76-7.71 (m, 2H), 7.23 (d, J=4.1 Hz, 1H), 4.21 (t, J=7.3 Hz, 2H), 2.67-2.59 (m, 10H), 2.36 (t, J=7.4 Hz, 2H), 1.82 (quint, J=7.8 Hz, 2H), 1.25 (quint, J=7.3 Hz, 2H). $^{13}$C NMR (101 MHz, $CDCl_3$) δ 160.1, 139.8, 136.2, 134.0, 129.5, 128.7, 128.4, 127.4, 58.8, 55.0, 52.4, 27.9, 26.3, 23.6.

LC/MS (M+H)=330.16

2-{4-[cyclohexyl(ethyl)amino]butyl}-4-phenyl-2,3-dihydropyridazin-3-one 11g

Using the same procedure described for 10d and starting from 2-(4-chlorobutyl)-4-phenylpyridazin-3(2H)-one 4a (50 mg, 0.19 mmol, 1 equiv.) and N-ethylcyclohexanamine (43.6 mg, 0.34 mmol, 1.8 equiv.), NaI (2.9 mg, 0.019 mmol, 0.1 equiv.), $Na_2CO_3$ (40.5 mg, 0.38 mmol, 2.0 equiv.), the title compound was obtained after purification on by silica gel flash chromatography using a gradient of 0% to 10% of MeOH in EtOAc (masse=19.6 mg, yield=29%). Salification and lyophilization led to the corresponding hydrochloride salt.

$^1$H NMR (400 MHz, $CDCl_3$) δ 7.80 (d, J=4.2 Hz, 1H), 7.78-7.72 (m, 2H), 7.44-7.35 (m, 3H), 7.25 (d, J=4.2 Hz, 1H), 4.24 (t, J=7.2 Hz, 2H), 2.85-2.49 (m, 5H), 1.95-1.82 (m, 4H), 1.80-1.73 (m, 2H), 1.68-1.56 (m, 3H), 1.31-1.02 (m, 8H). $^{13}$C NMR (101 MHz, $CDCl_3$) δ 139.7, 136.3, 134.0, 129.5, 128.7, 128.4, 127.5, 60.4, 52.0, 49.4, 44.5, 28.5, 26.2, 26.1, 26.0, 25.9, 16.0.

LC/MS (M+H)=354.25

4-(4-fluorophenyl)-2-(4-morpholinobutyl)pyridazin-3(2H)-one 11h

Using the same procedure described for 10d and starting from 2-(4-chlorobutyl)-4-(4-fluorophenyl)-2,3-dihydropyridazin-3-one 4b (28 mg, 0.1 mmol, 1 equiv.) and 2,6-dimethylmorpholine (16.8 mg, 0.20 mmol, 2.0 equiv.), NaI (1.5 mg, 0.01 mmol, 0.1 equiv.), $K_2CO_3$ (26.6 mg, 0.19 mmol, 2.0 equiv.), the title compound 11h was obtained (masse=23.0 mg, yield=72%). Salification and lyophilization led to the corresponding hydrochloride salt.

$^1$H NMR (400 MHz, $CDCl_3$) δ 7.85-7.75 (m, 3H), 7.25 (d, J=4.2 Hz, 1H), 7.16-7.08 (m, 2H), 4.26 (t, J=7.2 Hz, 2H), 3.70 (dd, J=5.4 Hz, J=4.1 Hz, 4H), 2.47-2.33 (m, 6H), 1.89 (quin., J=7.6 Hz, 2H), 1.58 (m, J=7.7 Hz, 2H). $^{13}$C NMR (101 MHz, $CDCl_3$) δ 164.7, 162.3, 159.9, 103.6, 136.1, 130.7, 130.6, 127.1, 115.5, 115.3, 66.9, 58.6, 53.7, 52.4, 26.3, 23.7.

LC/MS (M+H)=332.15

4-(4-hydroxyphenyl)-2-(4-morpholinobutyl)pyridazin-3(2H)-one 11i

Step 1: 2-(4-morpholinobutyl)-4-(4-((tetrahydro-2H-pyran-2-yl)oxy)phenyl)pyridazin-3(2H)-one Using the same procedure described for 10d and starting from 2-(4-chlorobutyl)-4-(4-((tetrahydro-2H-pyran-2-yl)oxy)phenyl) pyridazin-3(2H)-one 4c (80 mg, 0.22 mmol, 1 equiv.) and morpholine (38.4 mg, 0.44 mmol, 2.0 equiv.), NaI (3.3 mg, 0.02 mmol, 0.1 equiv.), $K_2CO_3$ (61.0 mg, 0.44 mmol, 2.0 equiv.), the title compound 11i was obtained after purification by chromatography on silica gel using AcOEt/MeOH 95/5 as eluent (masse=47.0 mg, yield=50%). Salification and lyophilization led to the corresponding hydrochloride salt.

$^1$H NMR (400 MHz, $CDCl_3$) δ 7.77 (d, J=4.3 Hz, 1H), 7.78-7.73 (m, 2H), 7.21 (d, J=4.3 Hz, 1H), 7.10-7.06 (d, 2H), 5.47 (t, J=3.2 Hz, 1H), 4.23 (t, J=7.5 Hz, 2H), 3.86 (ddd, J=11.4 Hz, J=9.8 Hz, J=3.2 Hz, 1H), 3.68 (dd, J=4.8 Hz, J=4.4 Hz, 4H), 3.69 (dt, J=11.5 Hz, J=4.1 Hz, 1H), 2.43-2.33 (m, 6H), 2.07-1.94 (m, 1H), 1.91-1.81 (m, 4H), 1.73-1.61 (m, 2H), 1.62-1.50 (m, 3H). $^{13}$C NMR (101 MHz, $CDCl_3$) δ 160.4, 158.4, 139.4, 136.4, 130.3, 127.3, 126.4, 116.4, 96.3, 67.2, 62.2, 58.8, 53.9, 52.6, 30.5, 26.5, 25.4, 23.9, 18.8.

Step 2: 4-(4-hydroxyphenyl)-2-(4-morpholinobutyl)pyridazin-3(2H)-one hydrochloride 11i The above product (47 mg, 0.11 mmol, 1 equiv.) was dissolved in THF (0.45 mL) and 1N HCl (0.22 mL, 2 equiv.) was added. The resulting mixture was then stirred at rt for 1 hour. Volatiles were evaporated in vacuo, and the crude vas triturated with dry $Et_2O$. The precipitate was filtered yielding the title product as hydrochloride salt (masse=25 mg, yield=60%).

LC/MS (M+H)=330.13.

2-(4-{2-oxa-6-azaspiro[3.3]heptan-6-yl}butyl)-4-phenyl-2,3-dihydropyridazin-3-one, 11t Using the same procedure described for 10d and starting from 2-(4-chlorobutyl)-4-(4-((tetrahydro-2H-pyran-2-yl)oxy)phenyl) pyridazin-3(2H)-one 4c (60 mg, 0.23 mmol, 1 equiv.) and 2-oxa-6-azaspiro[3.3]heptane hemioxalate (90.5 mg, 0.91 mmol, 4.0 equiv.), NaI (3.4 mg, 0.02 mmol, 0.1 equiv.), $Na_2CO_3$ (48.6 mg, 0.46 mmol, 2.0 equiv.), the title compound 11t was obtained after purification by chromatography on silica gel using AcOEt/MeOH 95/5 as eluent (masse=43.1 mg, yield=58%). Salification and lyophilization led to the corresponding hydrochloride salt.

$^1$H NMR (400 MHz, $CDCl_3$) δ 7.65 (d, J=4.2 Hz, 1H), 7.63-7.58 (m, 2H), 7.31-7.22 (m, 3H), 7.11 (d, J=4.2 Hz, 1H), 4.56 (s, 4H), 4.07 (t, J=7.3 Hz, 2H), 3.18 (s, 4H), 2.26 (t, J=7.3 Hz, 2H), 1.69 (quin, J=7.5 Hz, 2H), 1.24 (quin, J=7.6 Hz, 2H).). $^{13}$C NMR (101 MHz, $CDCl_3$) δ 160.2, 139.8, 136.3, 134.1, 129.6, 128.8, 128.5, 127.6, 81.2, 63.8, 59.1, 52.3, 50.8, 26.2, 24.7.

LC/MS (M+H)=330.16

2-{4-[benzyl(methyl)amino]butyl}-6-methyl-4-phenyl-2,3-dihydropyridazin-3-one 11v Using the same procedure described for 10d and starting from 2-(4-chlorobutyl)-6-methyl-4-phenyl-2,3-dihydropyridazin-3-one 4d (60 mg, 0.22 mmol, 1 equiv.) and N-methylbenzylamine (39.4 mg, 42 μL, 0.32 mmol, 1.5 equiv.), NaI (3.2 mg, 0.02 mmol, 0.1 equiv.), $Na_2CO_3$ (34.5 mg, 0.32 mmol, 1.5 equiv.), the title compound was obtained after purification on by silica gel flash chromatography using a gradient of 0% to 10% of MeOH in EtOAc (masse=38.3 mg, yield=49%). Salification and lyophilization led to the corresponding hydrochloride salt.

$^1$HNMR (400 MHz, $CDCl_3$) δ 7.77-7.72 (m, 2H), 7.42-7.38 (m, 3H), 7.33-7.27 (m, 4H), 7.25-7.21 (m, 1H), 7.15 (s, 1H), 4.18 (t, J=7.4 Hz, 2H), 3.55 (s, 2H), 2.49 (t, J=7.5 Hz, 2H), 2.34 (s, 3H), 2.22 (s, 3H), 1.85 (quin, J=7.5 Hz, 2H), 1.67-1.60 (m, 2H). 13C NMR (101 MHz, $CDCl_3$) δ 159.3, 144.4, 139.6, 134.3, 129.7, 129.5, 129.4, 128.9, 128.6, 128.5, 127.5, 62.1, 56.9, 52.2, 41.9, 26.4, 24.2, 21.1.

LC/MS (M+H)=362.16

2-[4-(azepan-1-yl)butyl]-6-methyl-4-phenyl-2,3-dihydropyridazin-3-one 11w

Using the same procedure described for 10d and starting from 2-(4-chlorobutyl)-6-methyl-4-phenyl-2,3-dihydropyridazin-3-one 4d (50 mg, 0.18 mmol, 1 equiv.) and hexamethyleneimine (26.9 mg, 30.5 μL, 0.27 mmol, 1.5 equiv.), NaI (2.7 mg, 0.018 mmol, 0.1 equiv.), $Na_2CO_3$ (28.7 mg, 0.27 mmol, 1.5 equiv.), the title compound was obtained after purification on by silica gel flash chromatography using a gradient of 0% to 10% of MeOH in EtOAc (masse=37.3 mg, yield=61%). Salification and lyophilization led to the corresponding hydrochloride salt.

$^1$H NMR (400 MHz, $CDCl_3$) δ 7.74-7.71 (m, 2H), 7.40-7.35 (m, 3H), 7.13 (s, 1H), 4.16 (t, J=7.4 Hz, 2H), 2.60 (t, J=5.4 Hz, 4H), 2.50 (t, J=7.7 Hz, 2H), 2.32 (s, 3H), 1.80 (quin, J=7.6 Hz, 2H), 1.60-1.50 (m, 10H). 13C NMR (101 MHz, CDCl3) δ 159.3, 144.3, 139.5, 134.3, 129.6, 129.5, 128.9, 128.4, 57.9, 55.6, 52.3, 27.8, 27.1, 26.6, 24.7, 21.1.

LC/MS (M+H)=340.18

2-(5-morpholinopentyl)-4-phenylpyridazin-3(2H)-one 12

Using the same procedure described for 10d and starting from 2-(5-bromopentyl)-4-phenyl-2,3-dihydropyridazin-3-one 5a (110 mg, 0.34 mmol, 1 equiv.) and morpholine (149.2 mg, 151 μL, 1.7 mmol, 5.0 equiv.), NaI (4.3 mg, 0.03 mmol, 0.1 equiv.), $K_2CO_3$ (80.0 mg, 0.57 mmol, 2.0 equiv.), the title compound was obtained after salification and lyophilization (masse=92.0 mg, yield=82%).

$^1$H NMR (400 MHz, $CDCl_3$) δ 7.82 (d, J=4.2 Hz, 1H), 7.80-7.76 (m, 2H), 7.48-7.39 (m, 3H), 7.28 (d, J=4.2 Hz, 1H), 4.24 (t, J=7.4 Hz, 2H), 3.70 (t, J=4.7 Hz, 4H), 2.46-2.39 (m, 4H), 2.27-2.29 (m, 2H), 1.88 (quin, J=7.6 Hz, 2H), 1.60-1.52 (m, 2H), 1.47-1.37 (m, 2H). $^{13}$C NMR (101 MHz, $CDCl_3$) δ 160.2, 139.7, 136.5, 133.9, 129.6, 128.7, 128.4, 127.7, 63.6, 57.7, 51.8, 51.7, 27.6, 23.8, 22.7.

LC/MS (M+H)=328.20

2-[6-(morpholin-4-yl)hexyl]-4-phenyl-2,3-dihydropyridazin-3-one 13

Using the same procedure described for 10d and starting from 2-(6-chlorohexyl)-4-phenyl-2,3-dihydropyridazin-3-one 6a (50 mg, 0.17 mmol, 1 equiv.) and morpholine (74.9 mg, 76 μL, 0.86 mmol, 5 equiv.), NaI (2.6 mg, 0.017 mmol, 0.1 equiv.), $Na_2CO_3$ (36.6 mg, 0.34 mmol, 2 equiv.), the title compound was obtained after purification by silica gel flash chromatography using a gradient of 0% to 10% of MeOH in EtOAc (masse=43 mg, yield=73%). Salification and lyophilization led to the corresponding hydrochloride salt.

$^1$H NMR (400 MHz, $CDCl_3$) δ 7.66 (d, J=4.2 Hz, 1H), 7.65-7.60 (m, 2H), 7.30-7.23 (m, 3H), 7.11 (d, J=4.2 Hz, 1H), 4.08 (t, J=7.4 Hz, 2H), 3.54 (t, J=4.8 Hz, 4H), 2.31-2.21 (m, 4H), 2.16 (t, J=7.4 Hz, 2H), 1.7 (quin J=7.3 Hz, 2H), 1.34 (quin, J=7.0 Hz, 2H), 1.28-1.16 (m, 4H). $^{13}$C NMR (101 MHz, $CDCl_3$) δ 160.0, 139.6, 136.1, 134.0, 129.5, 128.7, 128.3, 127.4, 67.0, 59.0, 53.7, 52.6, 28.2, 27.1, 26.6, 26.3.

LC/MS (M+H)=342.22

2-(4-morpholinobutyl)-5-phenylpyridazin-3(2H)-one 14

Using the same procedure described for 10d and starting from 2-(4-chlorobutyl)-5-phenylpyridazin-3(2H)-one 6a (120 mg (~80% purity), 0.45 mmol, 1.0 equiv.) and morpholine (199 mg, 200 μL, 2.28 mmol, 5.0 equiv.), NaI (6.3 mg, 0.045 mmol., 0.1 equiv.), $K_2CO_3$ (126.2 mg, 0.91 mmol, 2.0 equiv.), the title compound was obtained (masse=94.0 mg, yield=66%). Salification and lyophilization led to the corresponding hydrochloride salt.

$^1$H NMR (400 MHz, $CDCl_3$) δ 8.04 (d, J=2.3 Hz, 1H), 7.59-7.54 (m, 2H), 7.53-7.47 (m, 3H), 7.04 (d, J=2.3 Hz, 1H), 4.22 (t, J=7.3 Hz, 2H), 3.71 (t, J=4.8 Hz, 4H), 2.45-2.38 (m, 6H), 1.88 (quin, J=7.4 Hz, 2H), 1.63-1.54 (m, 2H). $^{13}$C NMR (101 MHz, $CDCl_3$) δ 160.6, 143.5, 135.7, 133.9, 130.2, 129.4, 126.8, 124.6, 66.9, 58.5, 53.7, 51.3, 26.4, 23.6.

LC/MS (M+H)=314.18

2-(5-morpholinopentyl)-5-phenylpyridazin-3(2H)-one 15

Using the same procedure described for 9b and starting from 2-(4-chlorobutyl)-5-phenylpyridazin-3(2H)-one 6a (120 mg (~85% purity), 0.37 mmol, 1 equiv.) and morpholine (162.7 mg, 164 μL, 1.87 mmol, 5.0 equiv.), NaI (5.6 mg, 0.04 mmol, 0.1 equiv.), $K_2CO_3$ (103.3 mg, 0.74 mmol, 2.0 equiv.), the title compound was obtained (masse=104.0 mg, yield=85%). Salification and lyophilization led to the corresponding hydrochloride salt.

$^1$H NMR (400 MHz, $CDCl_3$) δ 8.05 (d, J=2.3 Hz, 1H), 7.60-7.55 (m, 2H), 7.53-7.47 (m, 3H), 7.05 (d, J=2.3 Hz, 1H), 4.2 (t, J=7.6 Hz, 2H), 3.71 (t, J=4.9 Hz, 4H), 2.45-2.41 (m, 4H), 2.37-2.31 (m, 2H), 1.87 (quin, J=7.3 Hz, 2H), 1.59-1.52 (m, 2H), 1.46-1.37 (m, 2H). $^{13}$C NMR (101 MHz, $CDCl_3$) δ 160.5, 143.4, 135.6, 134.0, 130.2, 129.4, 126.8, 124.6, 67.0, 58.9, 53.8, 51.5, 28.3, 26.2, 24.6.

LC/MS (M+H)=328.20

Method 2

When the nitrogen heterocycloalkyl group of general formula 9-15 presents in its structure a ketone, in this particular case this oxo function can be easily reduced to alcohol with the mean of borohydride reagent (for example sodium borohydride) to yield products of general formula 16.

Scheme 2

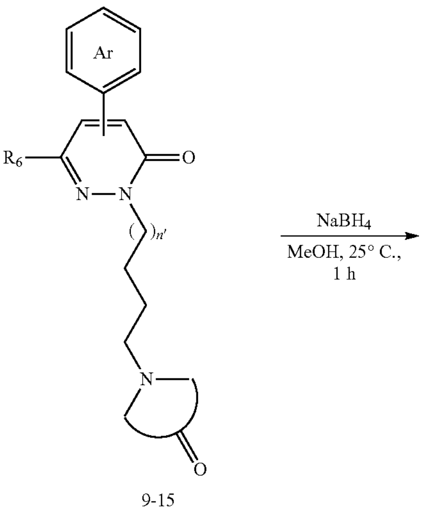

9-15
$R_6$ = H,
($C_1$—$C_4$)
alkyl group
n' = 0-3

-continued

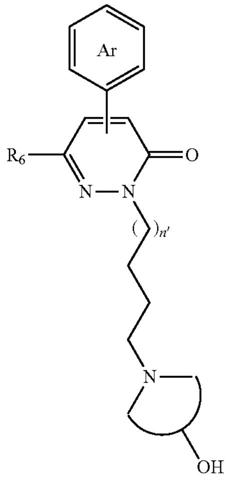

16

Example A-2: Preparation of 2-(4-(3-hydroxy-8-azabicyclo[3.2.1]octan-8-yl)butyl)-4-phenylpyridazin-3(2H)-one 16

To a solution of 8-(4-(6-oxo-5-phenylpyridazin-1(6H)-yl)butyl)-8-azabicyclo[3.2.1]octan-3-one 101 (50 mg, 0.14 mmol, 1 equiv.) in MeOH (1 mL) was added portionwise $NaBH_4$ (10.9 mg, 0.28 mmol, 2 equiv.) and the resulting mixture was stirred at 25° C. for 1 h. The progress of the reaction was monitoring by TLC (EtOAc/MeOH/33%. $NH_4OH$ 85/15/1). The resulting mixture was quenched with a saturated $NH_4Cl$ solution (3 mL), diluted with $H_2O$ (2 mL) and extracted twice with EtOAc (8 mL). The combined organic layers were dried over $Na_2SO_4$, filtered and evaporated in vacuo. The crude was purified by flash chromatography on silica gel using as eluent EtOAc/MeOH/33% $NH_4OH$ 85/15/1 to yield the title compound (masse=43.0 mg, yield=78%). Salification and lyophilization led to the corresponding hydrochloride salt.

LC/MS (M+H)=354.19

Method 3

Alternatively, the Suzuki-Miyaura cross coupling reaction can be performed later in the sequence enabling more convergent methods for the introduction of various aryl or aralkyl substituents on positions 4. Using the same conditions described previously, N-Alkylation of chloropyridazinone derivatives with appropriate alkyl-dihalides afforded intermediates 17. A derivatization step of 17 with suitable boronic acid reagents under Suzuki-Miyaura conditions led to intermediates 18, 19 and 22 which were finally involved in a nucleophilic substitution reaction, giving examples of the present invention (cpds 11 and 20). Catalytic Hydrogenation of 20 using Pd/C (10%) at atmospheric pressure furnished compounds of general formula 21 as depicted in scheme 3.

Scheme 3

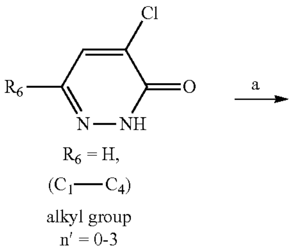

-continued

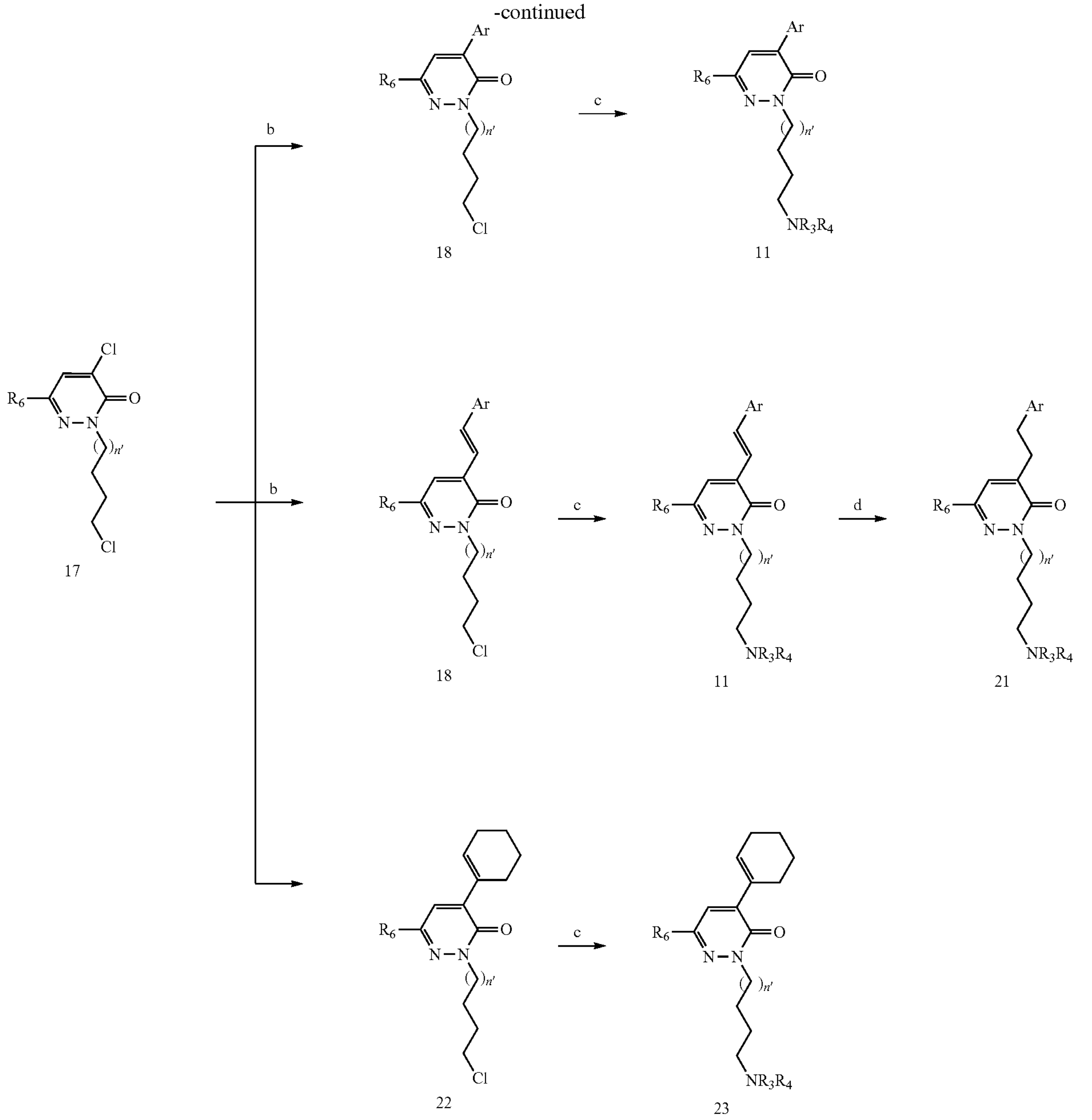

18 11 17 18 11 21 22 23

Conditions: a) $Br(CH_2)_{n'+3}$—Cl, NaH, DMF, 0° C. → 25° C., 12h; b) Ar—$B(OH)_2$ or $Ar(CH_2{=}CH_2)$—$B(OH)_2$, $Na_2CO_3$, $Pd(PPh_3)_4$, DME—$H_2O$, 100° C., 30 min, μwaves irradiations; c) $NHR_3R_4$, NaI, $Na_2CO_3$, MeCN, 80° C., overnight.

4-chloro-2-(4-chlorobutyl)-2,3-dihydropyridazin-3-one 17

The reaction was performed in anhydrous conditions under argon atmosphere. To a solution of 4-chloropyridazin-3(2H)-one 1 (1.0 g, 7.67 mmol, 1 equiv.) in dry DMF (26.5 mL) cooled to 0° C. was added portionwise NaH (1.5 eq., 276 mg, 11.5 mmol) and the mixture was stirred at 0° C. for 30 min. Then, 1-bromo-4-chlorobutane (3.95 g, 2.66 mL, 22.9 mmol, 3.0 equiv.) was added at 0° C. and the mixture was allowed to warm up to rt and stirred for 3 h. The mixture was quenched with $H_2O$ (5 mL) and extracted with EtOAc (2×5 mL). The combined organic layers were washed with brine, dried over $Na_2SO_4$, filtered and concentrated to dryness. The crude was purified by column chromatography over silica gel (solid loading, eluent: Heptane/EtOAc: 1/2) to give the title compound as a yellow oil (masse=1.48 g, yield=88%).

$^1H$ NMR (400 MHz, $CDCl_3$) δ 7.85-7.77 (m, 3H), 7.25 (d, J=4.3 Hz, 1H), 7.00-6.94 (m, 2H), 4.28 (t, J=7.1 Hz, 2H), 3.85 (s, 3H), 3.59 (t, J=6.5 Hz, 2H), 2.10-1.97 (m, 2H), 1.91-1.81 (m, 2H). $^{13}C$ NMR (101 MHz, $CDCl_3$) δ 160.9, 160.4, 139.3, 136.5, 130.3, 126.3, 114.0, 55.5, 51.7, 44.6, 29.8, 25.9.

2-(4-chlorobutyl)-4-(4-methoxyphenyl)-2,3-dihydropyridazin-3-one 18 a

A microwave vial (oven-dried and under argon) was charged with 4-methoxyphenylboronic acid (68.7 mg, 0.45 mmol, 2.0 equiv.), 4-chloro-2-(4-chlorobutyl)-2,3-dihydropyridazin-3-one 17 (50 mg, 0.23 mmol, 1.0 equiv.), sodium carbonate (72.3 mg, 0.68 mmol, 3 equiv.). Tetrakis(triphenylphosphine) palladium(0) (13.2 mg, 5 mol %) was then added, followed by DME (1.2 mL) and $H_2O$ (0.36 mL) The vial was properly capped and the mixture vessel was evacuated and backfilled with argon (process repeated 3 times), and heated at 100° C. under microwaves irradiations until complete conversion of the starting material. The reaction conversion was monitored by HPLC and was usually completed within 30 min. After cooling to room temperature, the reaction mixture was evaporated to dryness. The crude was partitioned through EtOAc (30 mL) and $H_2O$ (50 mL). The aqueous phase was extracted twice with EtOAc (20 mL). The organic phases were combined, washed with brine and dried ($Na_2SO_4$) and evaporated. The crude material was purified by silica gel chromatography (EtOAc/heptane, 1/4, to yield the title compound (masse=60 mg, yield=91%).

$^1$H NMR (400 MHz, $CDCl_3$) δ 7.85-7.77 (m, 3H), 7.25 (d, J=4.3 Hz, 1H), 7.00-6.94 (m, 2H), 4.28 (t, J=7.1 Hz, 2H), 3.85 (s, 3H), 3.59 (t, J=6.5 Hz, 2H), 2.10-1.97 (m, 2H), 1.91-1.81 (m, 2H). $^{13}$C NMR (101 MHz, $CDCl_3$) δ 160.9, 160.4, 139.3, 136.5, 130.3, 126.3, 114.0, 55.5, 51.7, 44.6, 29.8, 25.9.

2-(4-chlorobutyl)-4-(4-chlorophenyl)-2,3-dihydropyridazin-3-one 18b

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 4-chloro benzene boronic acid (70.7 mg, 0.45 mmol, 2 equiv.) the title compound was obtained (masse=45.2 mg, yield=67%).

$^1$H NMR (400 MHz, $CDCl_3$) δ 7.84 (d, J=4.2 Hz, 1H), 7.78-7.73 (m, 2H), 7.45-7.39 (m, 2H), 7.28 (d, J=4.2 Hz, 1H), 4.28 (t, J=7.1 Hz, 2H), 3.59 (t, J=6.5 Hz, 2H), 2.09-1.97 (m, 2H), 1.92-1.82 (m, 2H). $^{13}$C NMR (101 MHz, $CDCl_3$) δ 160.0, 138.6, 136.3, 135.9, 132.4, 130.2, 128.8, 127.5, 51.8, 44.5, 29.8, 25.9.

2-(4-chlorobutyl)-4-(3-chlorophenyl)-2,3-dihydropyridazin-3-one 18c

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 3-chlorophenylboronic acid (70.7 mg, 0.45 mmol, 2 equiv.) the title compound was obtained (masse=61 mg, yield=90%).

$^1$H NMR (400 MHz, $CDCl_3$) δ 7.83 (d, J=4.2 Hz, 1H), 7.81 t, J=1.9 Hz, 1H), 7.68 (dt, J=6.9 Hz, J=1.9 Hz), 7.40-7.32 (m, 2H), 7.27 (d, J=4.2 Hz, 1H), 4.27 (t, J=7.1 Hz, 2H), 3.58 (t, J=6.6 Hz, 2H), 2.01 (quin, J=7.1 Hz, 2H), 1.88-1.80 (m, 2H). $^{13}$C NMR (101 MHz, $CDCl_3$) δ 159.8, 138.3, 136.3, 135.7, 134.5, 129.8, 129.7, 128.9, 127.9, 126.9, 51.6, 44.5, 29.8, 25.8.

2-(4-chlorobutyl)-4-(2-chlorophenyl)-2,3-dihydropyridazin-3-one 18d

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 2-chlorophenylboronic acid (70.7 mg, 0.45 mmol, 2 equiv.) the title compound was obtained (masse=66 mg, yield=98%).

$^1$H NMR (400 MHz, $CDCl_3$) δ 7.82 (d, J=4.2 Hz, 1H), 7.45-7.42 (m, 1H), 7.36-7.28 (m, 3H), 7.19 (d, J=4.2 Hz, 1H), 4.25 (t, J=7.1 Hz, 2H), 3.56 (t, J=6.5 Hz, 2H), 2.0 (quin, J=7.3 Hz, 2H), 1.82 (quin, J=7.0 Hz, 2H). $^{13}$C NMR (101 MHz, $CDCl_3$) δ 159.5, 139.3, 135.7, 133.1, 133.0, 131.0, 130.5, 130.2, 130.0, 126.7, 51.4, 44.3, 29.5, 25.8.

2-(4-chlorobutyl)-4-[4-(trifluoromethyl)phenyl]-2,3-dihydropyridazin-3-one 18e Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 4-trifluoromethylphenylboronic acid (85.9 mg, 0.45 mmol, 2 equiv.) the title compound was obtained (masse=72.5 mg, yield=97%).

$^1$H NMR (400 MHz, $CDCl_3$) δ 7.84 (d, J=8.2 Hz, 2H, 7.81 (d, J=4.2 Hz, 1H), 7.63 (d, J=8.4 Hz, 2H), 7.26 (d, J=4.2 Hz, 1H), 4.23 (t, J=7.1 Hz, 2H), 3.53 (t, J=6.6 Hz, 2H), 1.97 (quin, J=7.4 Hz, 2H), 1.8 (m, 2H). $^{13}$C NMR (101 MHz, $CDCl_3$) δ 130.0, 138.3, 137.4, 136.1, 131.3 (q, J=32.4 Hz), 129.1, 128.2, 125.3 (q, J 3.7 Hz), 125.2 (q, J=265.6 Hz), 51.6, 44.3, 29.5, 25.5.

$^{19}$F (376 MHz, $CDCl_3$)—62.70

2-(4-chlorobutyl)-4-(thiophen-3-yl)-2,3-dihydropyridazin-3-one 18f

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 3-thiopheneboronic acid (57.9 mg, 0.45 mmol, 2 equiv.) the title compound was obtained (masse=53.7 mg, yield=88%).

$^1$H NMR (400 MHz, $CDCl_3$) δ 8.61 (dd, J=3.0, 1.3 Hz, 1H), 7.82 (d, J=4.3 Hz, 1H), 7.53 (dd, J=5.1, 1.3 Hz, 1H), 7.42 (d, J=4.3 Hz, 1H), 7.38 (dd, J=5.2, 3.1 Hz, 1H), 4.30 (t, J=7.1 Hz, 2H), 3.59 (t, J=6.6 Hz, 2H), 2.10-1.97 (m, 2H), 1.93-1.80 (m, 2H). $^{13}$C NMR (101 MHz, $CDCl_3$) δ 159.8, 136.4, 134.0, 133.7, 129.3, 126.2, 125.8, 124.9, 51.8, 44.6, 29.8, 25.9.

2-(4-chlorobutyl)-4-(furan-3-yl)-2,3-dihydropyridazin-3-one 18g

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 3-furanboronic acid (50.6 mg, 0.45 mmol, 2 equiv.) the title compound was obtained (masse=43.8 mg, yield=77%).

$^1$H NMR (400 MHz, $CDCl_3$) δ 8.66 (t, J=1.2 Hz, 1H), 7.80 (d, J=4.3 Hz, 1H), 7.52-7.47 (m, 1H), 7.29 (d, J=4.3 Hz, 1H), 6.73 (dd, J=2.0, 0.8 Hz, 1H), 4.29 (t, J=7.1 Hz, 2H), 3.58 (t, J=6.5 Hz, 2H), 2.08-1.96 (m, 2H), 1.90-1.78 (m, 2H). $^{13}$C NMR (101 MHz, $CDCl_3$) δ 159.2, 146.2, 143.4, 136.2, 132.5, 123.8, 119.0, 107.5, 51.6, 44.5, 29.8, 25.9.

4-(1-benzofuran-2-yl)-2-(4-chlorobutyl)-2,3-dihydropyridazin-3-one 18h

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and benzofuran-2-boronic acid (73.2 mg, 0.45 mmol, 2 equiv.) the title compound was obtained (masse=43.4 mg, yield=63%).

$^1H$ NMR (400 MHz, $CDCl_3$) δ 8.04 (d, J=1.0 Hz, 1H), 7.90 (d, J=4.3 Hz, 1H), 7.79 (d, J=4.3 Hz, 1H), 7.67 (ddd, J=7.7, 1.3, 0.7 Hz, 1H), 7.50 (dq, J=8.3, 0.9 Hz, 1H), 7.37 (ddd, J=8.4, 7.2, 1.3 Hz, 1H), 7.30-7.22 (m, 1H), 4.33 (t, J=7.1 Hz, 2H), 3.61 (t, J=6.5 Hz, 2H), 2.06 (tt, J=8.7, 6.8 Hz, 2H), 1.93-1.83 (m, 2H). $^{13}C$ NMR (101 MHz, $CDCl_3$) δ 157.8, 155.0, 148.9, 136.3, 129.1, 126.5, 123.5, 122.6, 112.9, 111.2, 51.6, 44.5, 29.8, 25.9.

2-(4-chlorobutyl)-4-(pyridin-3-yl)-2,3-dihydropyridazin-3-one 18i

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 3-pyridylboronic acid (55.6 mg, 0.45 mmol, 2 equiv.) the title compound was obtained (masse=53.1 mg, yield=89%).

$^1H$ NMR (400 MHz, $CDCl_3$) δ 8.86 (dd, J=2.3 Hz, J=0.9 Hz, 1H), 8.60 (dd, J=4.9 Hz, J=1.6 Hz, 1H), 8.21 (dt, J=8.0 Hz, J=2.4 Hz, 1H), 7.83 (d, J=4.2 Hz, 1H), 7.34 (ddd, J=8.0 Hz, J=4.9 Hz, J=0.9 Hz, 1H), 7.31 (d, J=4.2 Hz, 1H), 4.25 (t, J=7.0 Hz, 2H), 3.55 (t, J=6.7 Hz, 2H), 1.99 (quin, J=7.3 Hz, 2H), 1.82 (quin, J=6.9 Hz, 2H). $^{13}C$ NMR (101 MHz, $CDCl_3$) δ 159.7, 150.4, 149.0, 136.6, 136.4, 136.2, 129.9, 127.7, 123.0, 51.4, 44.2, 29.5, 25.7.

2-(4-chlorobutyl)-4-(3,5-dichlorophenyl)-2,3-dihydropyridazin-3-one 18j

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and 3,5-dichlorophenylboronic acid (43.1 mg, 0.23 mmol, 1 equiv.) at 85° C. under classical heat (3h) the title compound was obtained as a brown oil (masse=52.6 mg, yield=70%). $^1H$ NMR (400 MHz, $CDCl_3$) δ. 7.84 (d, J=4.2 Hz, 1H), 7.69 (d, J=1.9 Hz, 2H), 7.39 (t, J=1.9 Hz, 1H), 7.27 (d, J=4.2 Hz, 1H), 4.26 (t, J=7.1 Hz, 2H), 3.57 (t, J=6.5 Hz, 2H), 2.05-1.96 (m, 2H), 1.88-1.79 (m, 2H). $^{13}C$ NMR (101 MHz, $CDCl_3$) δ 159.4, 136.9, 136.6, 136.0, 135.1, 129.5, 128.1, 127.1, 51.8, 44.4, 29.6, 25.7.

2-(4-chlorobutyl)-4-[(E)-2-phenylethenyl]-2,3-dihydropyridazin-3-one 19a

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and (E)-styrylboronic acid (66.9 mg, 0.45 mmol, 2 equiv.) the title compound was obtained (masse=52.9 mg, yield=81%).

$^1H$ NMR (400 MHz, $CDCl_3$) δ 7.83 (d, J=16.3 Hz, 1H), 7.76 (d, J=4.3 Hz, 1H), 7.59-7.53 (m, 2H), 7.40-7.34 (m, 2H), 7.34-7.28 (m, 1H), 7.24-7.20 (m, 2H), 7.17 (d, J=0.7 Hz, 0H), 4.26 (t, J=7.1 Hz, 2H), 3.59 (t, J=6.6 Hz, 2H), 2.02 (ddt, J=8.5, 7.2, 6.1 Hz, 2H), 1.91-1.81 (m, 2H). $^{13}C$ NMR (101 MHz, $CDCl_3$) δ 160.1, 137.0, 136.6, 136.4, 136.4, 129.1, 128.9, 127.5, 124.8, 121.6, 51.4, 44.5, 29.7, 25.9.

2-(4-chlorobutyl)-4-(cyclohex-1-en-1-yl)-2,3-dihydropyridazin-3-one 22a

Using the same procedure than described for preparation of compound 18a and starting from 4-chloro-2-(4-chlorobutyl)-2,3-dihydropyridazin-3-one 17 (50 mg, 0.23 mmol, 1.0 equiv.) and (cyclohex-1-en-1-yl) boronic acid (57.0 mg, 0.45 mmol, 2 equiv.) the title compound was obtained as a yellow oil (masse=29.6.9 mg, yield=49%).

$^1H$ NMR (400 MHz, $CDCl_3$) δ 7.68 (d, J=4.4 Hz, 1H), 7.04 (tt, J=4.1 Hz, J=1.5 Hz, 1H), 6.96 (d, J=4.3 Hz, 1H), 4.19 (t, J=7.1 Hz, 2H), 3.54 (t, J=6.6 Hz, 2H), 2.33-2.27 (m, 2H), 2.27-2.20 (m, 2H), 2.00-1.90 (m, 2H), 1.84-1.77 (m, 2H), 1.75-1.69 (m, 2H), 1.66-1.58 (m, 2H). $^{13}C$ NMR (101 MHz, $CDCl_3$) δ 160.2, 140.6, 136.3, 134.6, 131.6, 124.3, 51.2, 44.2, 29.4, 26.7, 25.7, 22.6, 21.7.

Example A-3: Preparation of 4-(4-methoxyphenyl)-2-[4-(morpholin-4-yl)butyl]-2,3-dihydro pyridazin-3-one, 11j To a solution of 2-(4-chlorobutyl)-4-(4-methoxyphenyl)-2,3-dihydropyridazin-3-one 18a (55.3 mg, 0.19 mmol) in MeCN (1.05 mL) and under argon was added morpholine (82.3 mg, 83.1 μL, 0.94 mmol), $Na_2CO_3$ (40.2 mg, 0.38 mmol, 2 equiv.) and NaI (3.7 mg, 10 mol %) and the reaction mixture was heated at 80° C. overnight under argon. The mixture was then quenched with $H_2O$ (15 mL) and extracted twice with EtOAc (10 mL). The combined organic layers were dried over $Na_2SO_4$, filtered and evaporated to dryness. The resulting residue was purified by silica gel flash chromatography using a gradient of 0% to 10% of MeOH in EtOAc to give the title compound (masse=43.3 mg, yield=67%). Salification and lyophilization led to the corresponding hydrochloride salt.

$^1H$ NMR (400 MHz, $CDCl_3$) δ 7.84-7.77 (m, 3H), 7.24 (d, J=4.2 Hz, 1H), 6.98-6.93 (m, 2H), 4.26 (t, J=7.3 Hz, 2H), 3.85 (s, 3H), 3.70 (t, J=4.7 Hz, 4H), 2.43 (t, J=4.6 Hz, 4H), 2.42-2.34 (m, 2H), 1.89 (p, J=7.5 Hz, 2H), 1.63-1.52 (m, 2H). $^{13}C$ NMR (101 MHz, $CDCl_3$) δ 160.9, 160.3, 139.2, 136.4, 130.3, 126.5, 126.2, 114.0, 67.1, 58.7, 55.5, 53.9, 52.5, 26.4, 23.9.

LC/MS (M+H)=344.19

4-(4-chlorophenyl)-2-[4-(morpholin-4-yl)butyl]-2,3-dihydropyridazin-3-one 11k

Using the same procedure than described for preparation of compound 11j and starting from 2-(4-chlorobutyl)-4-(4-chlorophenyl)-2,3-dihydropyridazin-3-one 18b (45 mg, 0.15 mmol, 1.0 equiv.) and morpholine (65.9 mg, 66.6 μL 0.75 mmol, 5 equiv.) the title compound was obtained (masse=18.1 mg, yield=34%). Salification and lyophilization led to the corresponding hydrochloride salt.

$^1H$ NMR (400 MHz, $CDCl_3$) δ 7.82 (d, J=4.2 Hz, 1H), 7.78-7.71 (m, 2H), 7.44-7.38 (m, 2H), 7.27 (d, J=4.2 Hz, 1H), 4.26 (t, J=7.3 Hz, 2H), 3.71 (t, J=4.7 Hz, 4H), 2.49-2.42 (m, 4H), 2.42-2.35 (m, 2H), 1.89 (quint, J=7.5 Hz, 2H), 1.58 (tdd, J=9.4, 6.7, 5.5 Hz, 2H). $^{13}C$ NMR (101 MHz, $CDCl_3$) δ 159.9, 138.5, 136.2, 135.8, 132.5, 130.1, 128.8, 127.4, 67.0, 58.6, 53.8, 52.6, 26.4, 23.8.

LC/MS (M+H)=348.15

4-(3-chlorophenyl)-2-[4-(morpholin-4-yl)butyl]-2,3-dihydropyridazin-3-one 11l

Using the same procedure than described for preparation of compound 11j and starting from 2-(4-chlorobutyl)-4-(3-chlorophenyl)-2,3-dihydropyridazin-3-one 18c (72 mg, 0.24 mmol, 1.0 equiv.) and morpholine (105.5 mg, 106.6 μL 1.21 mmol, 5 equiv.) the title compound was obtained (masse=62.0 mg, yield=74%). Salification and lyophilization led to the corresponding hydrochloride salt.

$^{1}$H NMR (400 MHz, $CDCl_3$) δ 7.76 (d, J=4.2 Hz, 1H), 7.75-7.72 (m, 1H), 7.60 (dt, J=6.8 Hz, J=1.9 Hz, 1H), 7.34-7.26 (m, 2H), 7.20 (d, J=4.2 Hz, 1H), 4.14 (t, J=7.3 Hz, 2H), 3.63 (t, J=4.6 Hz, 4H), 2.40-2.29 (m, 6H), 1.77 (quin, J=7.6 Hz, 2H), 1.48 (m, 2H). $^{13}$C NMR (101 MHz, $CDCl_3$) δ 159.6, 138.1, 135.6, 134.3, 129.6, 129.5, 128.7, 127.7, 126.8, 67.0, 58.5, 53.7, 52.4, 26.3, 23.7.

LC/MS (M+H)=348.14

4-(2-chlorophenyl)-2-[4-(morpholin-4-yl)butyl]-2,3-dihydropyridazin-3-one 11m

Using the same procedure than described for preparation of compound 11j and starting from 2-(4-chlorobutyl)-4-(2-chlorophenyl)-2,3-dihydropyridazin-3-one 18d (65 mg, 0.22 mmol, 1.0 equiv.) and morpholine (95.3 mg, 96.2 μL 1.10 mmol, 5 equiv.) the title compound was obtained (masse=56.0 mg, yield=74%). Salification and lyophilization led to the corresponding hydrochloride salt.

$^{1}$H NMR (400 MHz, $CDCl_3$) δ 7.79 (d, J=4.2 Hz, 1H), 7.45-7.40 (m, 1H), 7.36-7.32 (m, 1H), 7.31-7.26 (m, 2H), 7.18 (d, J=4.2 Hz, 1H), 4.22 (t, J=7.3 Hz, 2H), 3.66 (t, J=4.7 Hz, 4H), 2.43-2.31 (m, 6H), 1.85 (quin, J=7.5 Hz, 2H), 1.54 (quin J=7.4 Hz, 2H). $^{1}$H NMR (400 MHz, $CDCl_3$) δ 159.3, 139.2, 135.6, 133.2, 132.9, 131.0, 130.4, 130.1, 129.9, 126.6, 66.9, 58.5, 53.7, 52.0, 26.3, 23.6.

LC/MS (M+H)=348.14

2-[4-(morpholin-4-yl)butyl]-4-[4-(trifluoromethyl)phenyl]-2,3-dihydropyridazin-3-one tin Using the same procedure than described for preparation of compound 11j and starting from 2-(4-chlorobutyl)-4-[4-(trifluoromethyl)phenyl]-2,3-dihydropyridazin-3-one 18e (72 mg, 0.22 mmol, 1.0 equiv.) and morpholine (94.8 mg, 95.8 μL 1.10 mmol, 5 equiv.) the title compound was obtained (masse=53.8 mg, yield=65%). Salification and lyophilization led to the corresponding hydrochloride salt.

$^{1}$H NMR (400 MHz, $CDCl_3$) δ 7.86 (d, J=8.2 Hz, 2H), 7.80 (d, J=4.1 Hz, 1H), 7.63 (d, J=8.2 Hz, 2H), 7.27 (d, J=4.1 Hz, 1H), 4.24 (t, J=7.4 Hz, 2H), 3.66 (t, J=4.8 Hz, 4H), 2.44-2.30 (m, 6H), 1.86 (quin, J=7.7 Hz, 2H), 1.54 (quin, J=7.6 Hz, 2H). $^{1}$H NMR (400 MHz, $CDCl_3$) δ 159.6, 138.2, 137.5, 136.0, 131.2 (q, J=32.9 Hz), 129.0, 128.1, 122.6, 66.9, 58.5, 53.7, 52.5, 26.2, 23.6.

LC/MS (M+H)=382.17

2-[4-(morpholin-4-yl)butyl]-4-(thiophen-3-yl)-2,3-dihydropyridazin-3-one 11o

Using the same procedure than described for preparation of compound 11j and starting from 2-(4-chlorobutyl)-4-(thiophen-3-yl)-2,3-dihydropyridazin-3-one 18f (53 mg, 0.19 mmol, 1.0 equiv.) and morpholine (85.9 mg, 86.7 μL 0.98 mmol, 5 equiv.) the title compound was obtained (masse=50.9 mg, yield=81%). Salification and lyophilization led to the corresponding hydrochloride salt.

$^{1}$H NMR (400 MHz, $CDCl_3$) δ 8.60 (dd, J=3.0, 1.3 Hz, 1H), 7.80 (d, J=4.3 Hz, 1H), 7.52 (dd, J=5.2, 1.3 Hz, 1H), 7.40 (d, J=4.4 Hz, 1H), 7.37 (dd, J=5.1, 3.0 Hz, 1H), 4.32-4.23 (m, 2H), 3.74-3.68 (m, 4H), 2.44 (t, J=4.6 Hz, 4H), 2.42-2.35 (m, 2H), 1.95-1.83 (m, 2H), 1.58 (tdd, J=9.4, 6.7, 5.5 Hz, 2H). $^{13}$C NMR (101 MHz, $CDCl_3$) δ 159.7, 136.2, 134.1, 133.6, 129.2, 126.2, 125.8, 124.8, 67.0, 58.7, 53.8, 52.5, 26.4, 23.7.

LC/MS (M+H)=320.14

4-(furan-3-yl)-2-[4-(morpholin-4-yl)butyl]-2,3-dihydropyridazin-3-one 11p

Using the same procedure than described for preparation of compound 11j and starting from 2-(4-chlorobutyl)-4-(furan-3-yl)-2,3-dihydropyridazin-3-one 18g (43 mg, 0.17 mmol, 1.0 equiv.) and morpholine (74.1 mg, 74.9 μL 0.85 mmol, 5 equiv.) the title compound was obtained (masse=34.3 mg, yield=66%). Salification and lyophilization led to the corresponding hydrochloride salt.

$^{1}$H NMR (400 MHz, $CDCl_3$) δ 8.68-8.62 (m, 1H), 7.78 (d, J=4.2 Hz, 1H), 7.48 (t, J=1.8 Hz, 1H), 7.28 (d, J=4.3 Hz, 1H), 6.72 (dd, J=2.0, 0.8 Hz, 1H), 4.26 (t, J=7.3 Hz, 2H), 3.72-3.66 (m, 4H), 2.45-2.40 (m, 4H), 2.39-2.33 (m, 2H), 1.87 (p, J=7.6 Hz, 2H), 1.62-1.51 (m, 2H). $^{13}$C NMR (101 MHz, $CDCl_3$) δ 159.1, 146.2, 143.4, 136.1, 132.5, 123.7, 119.1, 107.5, 67.1, 58.7, 53.8, 52.4, 26.4, 23.8.

LC/MS (M+H)=304.16

4-(3a,7a-dihydro-1-benzofuran-2-yl)-2-[4-(morpholin-4-yl)butyl]-2,3-dihydropyridazin-3-one 11q Using the same procedure than described for preparation of compound 11j and starting from 2-(4-4-(1-benzofuran-2-yl)-2-(4-chlorobutyl)-2,3-dihydropyridazin-3-one 18h (43.4 mg, 0.14 mmol, 1.0 equiv.) and morpholine (62.4 mg, 63.1 μL 0.72 mmol, 5 equiv.) the title compound was obtained (masse=36.9 mg, yield=72%). Salification and lyophilization led to the corresponding hydrochloride salt.

$^{1}$H NMR (400 MHz, $CDCl_3$) δ 7.94 (d, J=1.0 Hz, 1H), 7.78 (d, J=4.4 Hz, 1H), 7.66 (d, J=4.4 Hz, 1H), 7.56 (dt, J=7.7, 1.1 Hz, 1H), 7.39 (dq, J=8.2, 0.9 Hz, 1H), 7.26 (ddd, J=8.4, 7.2, 1.3 Hz, 1H), 7.20-7.11 (m, 1H), 4.21 (dd, J=7.9, 6.8 Hz, 2H), 3.65-3.55 (m, 4H), 2.37-2.32 (m, 4H), 2.31-2.26 (m, 2H), 1.81 (p, J=7.7 Hz, 2H), 1.49 (tdd, J=9.4, 6.7, 5.5 Hz, 2H). $^{13}$C NMR (101 MHz, $CDCl_3$) δ 157.7, 154.9, 148.9, 136.0, 129.1, 128.6, 126.4, 123.4, 122.5, 112.7, 111.2, 67.0, 58.6, 53.8, 52.4, 26.4, 23.8.

LC/MS (M+H)=354.18

2-[4-(morpholin-4-yl)butyl]-4-(pyridin-3-yl)-2,3-dihydropyridazin-3-one 11r

Using the same procedure than described for preparation of compound 11j and starting from 2-(4-chlorobutyl)-4-(pyridin-3-yl)-2,3-dihydropyridazin-3-one 18i (53.1 mg, 0.20 mmol, 1.0 equiv.) and morpholine (87.7 mg, 88.6 μL 1.00 mmol, 5 equiv.) the title compound was obtained (masse=20.1 mg, yield=32%). Salification and lyophilization led to the corresponding hydrochloride salt.

$^{1}$H NMR (400 MHz, $CDCl_3$) δ 8.78 (dd, J=2.3, 0.9 Hz, 1H), 8.53 (dd, J=4.8, 1.7 Hz, 1H), 8.14 (dt, J=8.0, 2.0 Hz, 1H), 7.75 (d, J=4.2 Hz, 1H), 7.26 (ddd, J=8.0, 4.9, 0.9 Hz, 1H), 7.22 (d, J=4.2 Hz, 1H), 4.22-4.11 (m, 2H), 3.65-3.53 (m, 4H), 2.37-2.30 (m, 4H), 2.30-2.22 (m, 2H), 1.78 (p, J=7.5 Hz, 2H), 1.47 (tdd, J=10.3, 6.7, 5.5 Hz, 2H). $^{13}$C NMR (101 MHz, $CDCl_3$) δ 159.8, 150.5, 149.1, 136.7, 136.5, 136.1, 130.1, 127.7, 123.1, 67.1, 58.6, 53.8, 52.6, 26.4, 23.8.

LC/MS (M+H)=315.18

2-[4-(morpholin-4-yl)butyl]-4-[(E)-2-phenylethenyl]-2,3-dihydropyridazin-3-one 20a Using the same procedure than described for preparation of compound 11j and starting from 2-(4-chlorobutyl)-4-[(E)-

2-phenylethenyl]-2,3-dihydropyridazin-3-one 19a (52.9 mg, 0.18 mmol, 1.0 equiv.) and morpholine (79.8 mg, 80.6 µL 1.00 mmol, 5 equiv.) the title compound was obtained (masse=40.5 mg, yield=73%). Salification and lyophilization led to the corresponding hydrochloride salt.

$^1H$ NMR (400 MHz, $CDCl_3$) δ 7.83 (d, J=16.4 Hz, 1H), 7.76 (d, J=4.3 Hz, 1H), 7.60-7.53 (m, 2H), 7.37 (ddt, J=8.1, 5.7, 1.9 Hz, 2H), 7.34-7.28 (m, 1H), 7.23 (d, J=4.3 Hz, 1H), 7.20 (d, J=16.4 Hz, 1H), 4.25 (dd, J=7.7, 6.9 Hz, 2H), 3.74-3.68 (m, 4H), 2.43 (t, J=4.8 Hz, 4H), 2.41-2.34 (m, 2H), 1.94-1.82 (m, 2H), 1.63-1.53 (m, 2H). $^{13}C$ NMR (101 MHz, $CDCl_3$) δ 160.1, 137.0, 136.7, 136.5, 136.3, 129.1, 128.9, 127.5, 124.8, 121.7, 67.1, 58.7, 53.9, 52.3, 26.5, 23.8.

LC/MS (M+H)=340.20

2-[4-(morpholin-4-yl)butyl]-4-(2-phenylethyl)-2,3-dihydropyridazin-3-one 21a Pd/C 10% (3.6 mg) and MeOH (10 mL) were placed into the reactor (20 mL capacity) equipped with a magnetic stirrer. 2-[4-(morpholin-4-yl)butyl]-4-[(E)-2-phenylethenyl]-2,3-dihydropyridazin-3-one 20a (36.7 mg, 0.11 mmol), was added, and the micro-reactor was purged by flushing first with argon than four times with hydrogen at atmospheric pressure. The resulting mixture was magnetically stirred overnight at room temperature. The catalyst particles were removed from the solution by filtration through celite, the volatiles were evaporated to give the title compound (36.8 mg, 99%). Salification and lyophilization led to the corresponding hydrochloride salt.

$^1H$ NMR (400 MHz, $CDCl_3$) δ 7.68 (d, J=4.0 Hz, 1H), 7.38-7.31 (m, 2H), 7.30-7.22 (m, 3H), 6.93 (dd, J=4.0, 1.0 Hz, 1H), 4.27 (t, J=7.2 Hz, 2H), 3.77 (t, J=4.8 Hz, 4H), 3.04-2.92 (m, 4H), 2.54-2.47 (m, 4H), 2.47-2.41 (m, 2H), 1.92 (quint, J=7.8 Hz, 2H), 1.66-1.58 (m, 2H). $^{13}C$ NMR (101 MHz, $CDCl_3$) δ 161.2, 143.0, 140.9, 135.9, 128.5, 128.5, 127.8, 126.3, 67.1, 58.6, 53.8, 51.8, 33.4, 32.2, 26.4, 23.7.

LC/MS (M+H)=342.22

Method 4: Introduction of Secondary Aliphatic Amines on Position 4

In an alternative method, the 4- aryl group of the pyridazone moiety could be replaced by secondary aliphatic amines $NR_7R_8$ as illustrated in scheme 4. A first N-alkylation of 4-halogeno pyridazinones with appropriate alkyl-dihalides with the use of NaH in DMF led to intermediates 17 as illustrated in scheme 3. A nucleophilic substitution reaction was then performed with appropriate aliphatic amines $NHR_3R_4$ leading to 24. Finally, a $S_NAr$ reaction with the mean of $HNR_7R_8$ provided compounds of general formula 25.

Scheme 4

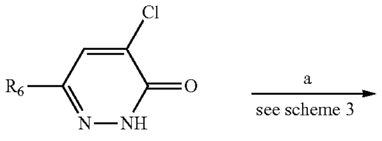

$R_6$ = H, ($C_1$—$C_4$) alkyl group
n' = 0-3

-continued

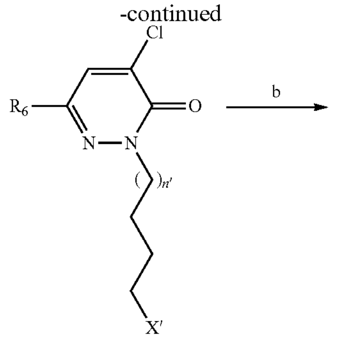

X' = Cl, Br
17

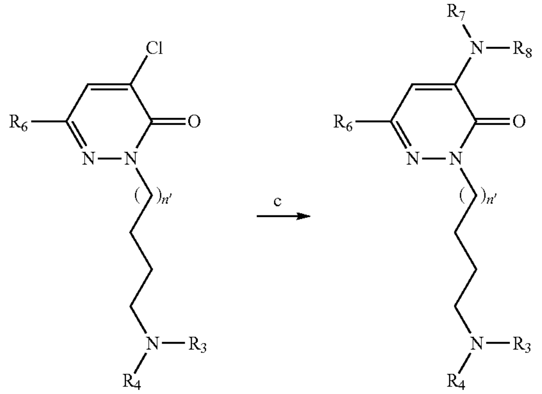

24 25

Conditions: a) $Br(CH_2)_{n'+3}$—X, NaH, DMF, 0° C. → 25° C., 12h; b) $HNR_3$,$R_4$, NaI, $K_2CO_3$, MeCN, 80° C., overnight c) $HNR_7R_8$, $K_2CO_3$, MeCN, 80° C., 18 h. Where-$NR_7R_8$ can form a nitrogen-containing heterocycloalkyl, as defined above.

4-chloro-2-[4-(morpholin-4-yl)butyl]-2,3-dihydropyridazin-3-one 24a

Using the same procedure described for 10d and starting from 4-chloro-2-(4-chlorobutyl)-2,3-dihydropyridazin-3-one 17 (100 mg, 0.45 mmol, 1 equiv.) and morpholine (78.8 mg, 0.90 mmol, 2 equiv.), NaI (6.8 mg, 0.04 mmol, 0.1 equiv.), $K_2CO_3$ (125.0 mg, 0.90 mmol, 2.0 equiv.), the title compound was obtained after purification by silica gel chromatography using (EtOAc/MeOH/$NH_4OH$ 85/13/2 as eluent (masse=63 mg, yield=51%).

$^1H$ NMR (400 MHz, $CDCl_3$) δ 7.62 (d, J=4.2 Hz, 1H), 7.31 (d, J=4.3 Hz, 1H), 4.18 (t, J=7.3 Hz, 2H), 3.67-3.61 (m, 4H), 2.40-2.29 (m, 6H), 1.85-1.76 (m, 2H), 1.54-1.44 (m, 2H). $^{13}C$ NMR (101 MHz, $CDCl_3$) δ 157.6, 137.1, 134.8, 128.9, 66.9, 58.4, 53.7, 52.8, 26.1, 23.5.

Example A-4: Preparation of 2-(4-morpholinobutyl)-4-(piperidin-1-yl)pyridazin-3(2H)-one 25a To a solution of 4-chloro-2-[4-(morpholin-4-yl)butyl]-2,3-dihydropyridazin-3-one 24a (63 mg, 0.23 mmol) in MeCN (1.0 mL) and under argon was added piperidine (38.9 mg, 45.1 µL, 0.45 mmol), $K_2CO_3$ (63.07 mg, 0.46 mmol) and NaI (3.7 mg, 10 mol %) and the reaction mixture was heated at 80° C. for 16 h under argon. The mixture was then quenched with $H_2O$ (8 mL) and extracted twice with EtOAc (10 mL). The combined organic layers were dried over $Na_2SO_4$, filtered and evaporated to dryness. The resulting residue was purified by silica gel flash chromatography using EtOAc/MeOH/$NH_4OH$: 85/15/0.1 as eluent to give the title compound 25a after salification and lyophilization (masse=52 mg, yield=71%).

$^1H$ NMR (400 MHz, $CDCl_3$) δ 7.55 (d, J=5.0 Hz, 1H), 6.22 (d, J=5.0 Hz, 1H), 4.14 (t, J=7.3 Hz, 2H), 3.74 (dd, J=5.3 Hz, J=4.1 Hz, 4H), 3.37 (dd, J=6.3 Hz, J=4.2 Hz, 4H), 2.53-2.41 (m, 6H), 2.1 (quin, J=7.3 Hz, 2H), 1.73-1.68 (m, 4H), 1.66-1.54 (m, 4H). $^{13}C$ NMR (101 MHz, $CDCl_3$) δ 158.2, 148.7, 137.5, 108.1, 68.9, 58.8, 53.8, 52.1, 49.4, 26.4, 25.8, 24.7, 23.6.

LC/MS (M+H)=312.23

Method 5: Introduction of Heterocyclic Aromatic Amines in Positions 4

In an alternative method, the 4-aryl group of the pyridazone moiety could be replaced by heterocyclic aromatic amines (pyrrole, pyrazole, and imidazole). A Buchwald-Hartwig cross-coupling reaction with the mean of $Pd_2(dba)_3$ and RuPhos can be performed starting from intermediates 17 previously described. Next, nucleophilic substitution reaction was performed with appropriate aliphatic amines $NHR_3R_4$ leading to compounds of general formula 27. The use of pyrrole provided an example of the present invention.

Scheme 5

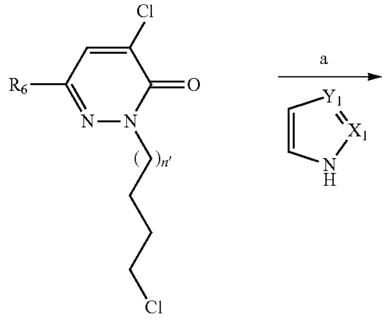

17

$R_6$ = H, ($C_1$—$C_4$) alkyl group n' = 0-3

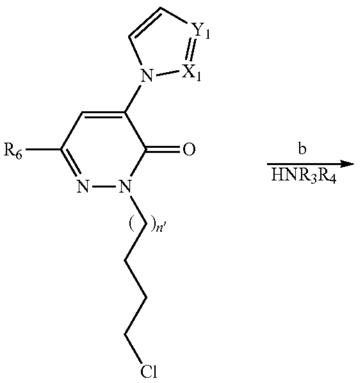

26

$X_1$ = N, CH $Y_1$ = CH, N

-continued

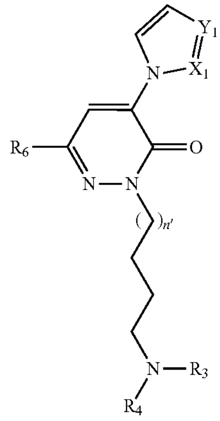

27

Conditions: a) $Pd_2(dba)_3$, (5 mol %), RuPhos (20 mol %), $Cs_2CO_3$ (2.5 equiv.), dioxane, 100° C., 18 h; b) $NHR_3R_4$, NaI, $Na_2CO_3$, MeCN, 80° C., overnight.

2-(4-chlorobutyl)-4-(1H-pyrrol-1-yl)-2,3-dihydropyridazin-3-one 26a

A microwave vial (oven-dried and under argon) was charged with 4-chloro-2-(4-chlorobutyl)-2,3-dihydropyridazin-3-one 17 (60 mg, 0.27 mmol, 1.0 equiv.), pyrrole (36.4 mg, 0.54 mmol, 2.0 equiv.), $Cs_2CO_3$ (223.3 mg, 0.68 mmol, 2.5 equiv.). Tris ((1E,4E)-1,5-diphenylpenta-1,4-dien-3-one) dipalladium (12.8 mg, 5 mol %) and RuPhos (25.3 mg, 20 mol %) was then added, followed by dioxane (1.5 mL). The vial was properly capped and the mixture vessel was evacuated and backfilled with argon (process repeated 3 times) and heated at 100° C. until complete conversion of the starting material. The reaction conversion was monitored by HPLC and was usually completed within 18 hours. After cooling to room temperature, the reaction mixture was evaporated to dryness. The crude was partitioned through EtOAc (30 mL) and $H_2O$ (50 mL). The aqueous phase was extracted twice with EtOAc (20 mL). The organic phases were combined, washed with brine and dried ($Na_2SO_4$) and evaporated. The crude material was purified by flash chromatography using Hept/EtOAc: 5/1 as eluent to give the title compound 26a as an orange oil (masse=40.8 mg, yield=60%).

$^1H$ NMR (400 MHz, $CDCl_3$) δ 7.78 (d, J=4.6 Hz, 1H), 7.49 (t, J=2.3 Hz, 2H), 7.03 (d, J=4.6 Hz, 1H), 6.33 (t, J=2.3 Hz, 2H), 4.27 (t, J=7.1 Hz, 2H), 3.57 (t, J=6.5 Hz, 2H), 2.01 (quin, J=7.1 Hz, 2H), 1.87-1.76 (m, 2H). $^{13}C$ NMR (101 MHz, $CDCl_3$) δ 156.6, 137.1, 137.0, 120.9, 115.6, 111.8, 51.7, 44.2, 29.5, 25.7.

Example A-5: Preparation of 2-[4-(morpholin-4-yl)butyl]-4-(1H-pyrrol-1-yl)-2,3-dihydropyridazin-3-one 27a Using the same procedure described for 10d and starting from 2-(4-chlorobutyl)-4-(1H-pyrrol-1-yl)-2,3-dihydropyridazin-3-one 26a (40.8 mg, 0.16 mmol, 1 equiv.) and morpholine (70.6 mg, 71.3 μL, 0.81 mmol, 5 equiv.), NaI (2.4 mg, 0.016 mmol, 0.1 equiv.), $Na_2CO_3$ (34.5 mg, 0.32 mmol, 2 equiv.), the title compound was obtained after purification by silica gel flash chromatography using a gradient of 0% to 15% of MeOH in EtOAc (masse=40 mg, yield=80%). Salification and lyophilization led to the corresponding hydrochloride salt.

$^1$H NMR (400 MHz, $CDCl_3$) δ 7.74 (d, J=4.7 Hz, 1H), 7.47 (t, J=2.3 Hz, 2H), 7.01 (d, J=4.7 Hz, 1H), 6.31 (t, J=2.3 Hz, 2H), 4.23 (t, J=7.3 Hz, 2H), 3.66 (t, J=4.8 Hz, 4H), 2.42-2.31 (m, 6H), 1.84 (m, J=7.7 Hz), 1.53 (m, J=6.9 Hz, 2H).

LC/MS (M+H)=303.18

Method 6

In an alternative method, the 4-aryl group of the pyridazone moiety could be replaced by aryl sulfides or arylalkoxides as illustrated in scheme 5. Starting from the above described 4-chloropyridazinone 24, reaction with sodium arylthiolate or sodium aryloxyde under nucleophilic aromatic substitution conditions led respectively to compounds of general formula 28 and 29. The use of thiophenol and phenol provided examples of the present inventions.

Scheme 6

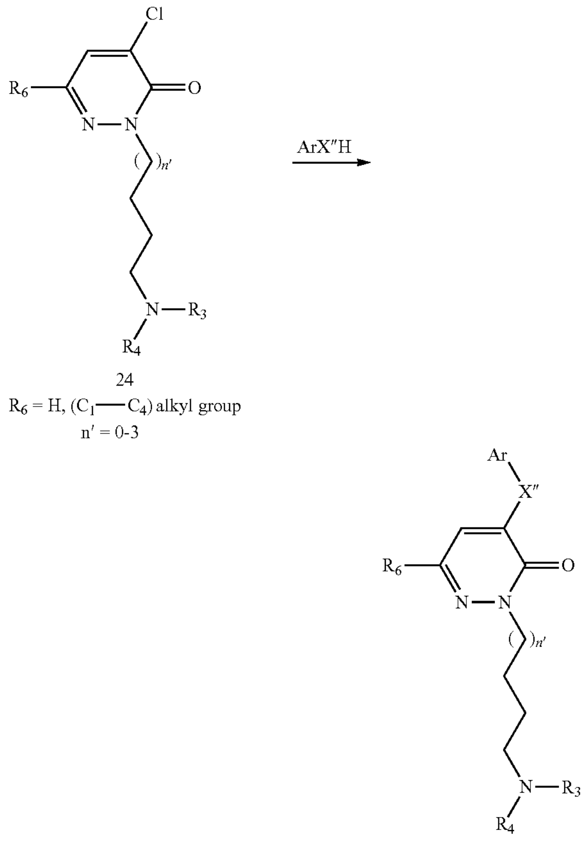

24

$R_6$ = H, ($C_1$—$C_4$) alkyl group n′ = 0-3

X″ = O,S

28: X″ = S

29: X″ = O

Conditions: NaH, DMF, 45° C., 0° C., 30 min, then addition of 25, 45° C., 3 h

Example A-6: 2-[4-(morpholin-4-yl)butyl]-4-(phenylsulfanyl)-2,3-dihydropyridazin-3-one 28a The reaction was performed in anhydrous conditions under argon atmosphere. To a solution of 4-chloro-2-[4-(morpholin-4-yl)butyl]-2,3-dihydropyridazin-3-one 24a (62.9 mg, 0.23 mmol, 1 equiv.) in dry DMF (1.0 mL) cooled to 0° C. was added portionwise NaH (5.8 mg, 0.24 mmol, 1.05 equiv.) and the mixture was stirred at 0° C. for 30 min. Then, thiophenol (28.0 mg, 0.25 mmol, 1.1 equiv.) was added dropwise at 0° C. and the mixture heated at 45° C. for 3 h. The mixture was quenched with $H_2O$ (15 mL) and extracted twice with EtOAc (2×15 mL). The combined organic layers were washed with brine, dried over $Na_2SO_4$, filtered and concentrated to dryness. After evaporation to dryness the residue was purified by silica gel flash chromatography using a gradient of 0% to 10% of MeOH in EtOAc (masse=31.5 mg, yield=39%). Salification and lyophilization led to the corresponding hydrochloride salt.

$^1$H NMR (400 MHz, $CDCl_3$) δ 7.54-7.50 (m, 2H), 7.48-7.44 (m, 3H), 7.43 (d, J=4.5 Hz, 1H), 6.25 (d, J=4.5 Hz, 1H), 4.18 (t, J=7.3 Hz, 2H), 3.67 (t, J=4.8 Hz, 4H), 2.44-2.30 (m, 6H), 1.83 (quint, J=7.5 Hz, 2H), 1.55-1.45 (m, 2H). $^{13}$C NMR (101 MHz, $CDCl_3$) δ 158.0, 147.0, 135.7, 135.5, 130.2, 128.5, 121.4, 67.0, 58.4, 53.6, 51.6, 26.2, 23.5.

LC/MS (M+H)=346.16

2-[4-(morpholin-4-yl)butyl]-4-phenoxy-2,3-dihydropyridazin-3-one, 29a

Using the same procedure described for 28a and starting from 4-chloro-2-[4-(morpholin-4-yl)butyl]-2,3-dihydropyridazin-3-one 24a (45.0 mg, 0.16 mmol, 1 equiv.) and phenol (18.7 mg, 17.5 μL, 0.20 mmol, 1.2 equiv.), the title compound was obtained after purification by silica gel flash chromatography using a gradient of 0% to 10% of MeOH in EtOAc (masse=39.1 mg, yield=71.7%). Salification and lyophilization led to the corresponding hydrochloride salt.

$^1$H NMR (400 MHz, $CDCl_3$) δ 7.53 (d, J=4.8 Hz, 1H), 7.44-7.38 (m, 2H), 7.28-7.22 (m, 1H), 7.12-7.07 (m, 2H), 6.20 (d, J=4.8 Hz, 1H), 4.23 (t, J=7.1 Hz, 2H), 3.69 (t, J=4.8 Hz, 1H), 2.48-2.33 (m, 6H), 1.86 (quint., J=4.7 Hz, 2H), 1.60-1.49 (m, 2H). $^{13}$C NMR (101 MHz, $CDCl_3$) δ 156.9, 155.6, 153.3, 136.3, 130.3, 126.3, 120.9, 108.1, 66.8, 58.3, 53.6, 51.6, 26.2, 23.7.

LC/MS (M+H)=330.18

Method 7

N-Alkylation of 1 with 1,3-dioxolan-methylsulfate derivative 30 with NaH in DMF afforded the diol 31 after deprotection of the dioxolane moiety in acidic medium. Chemoselective tosylation of the primary alcohol 31 with TsCl in the presence of dibutyltin oxide and $Et_3N$ yielded compound 32. Finally, a nucleophilic substitution reaction was performed with appropriate aliphatic amines $NHR_3R_4$ leading to compounds of general formula 33.

Scheme 7

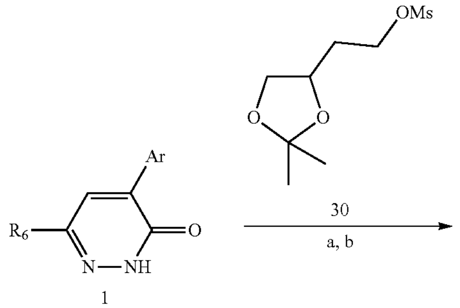

1

$R_6$ = H, ($C_1$-$C_4$)alkyl group

-continued

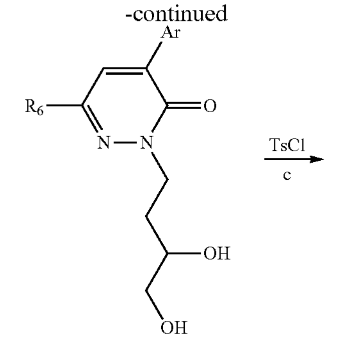

31

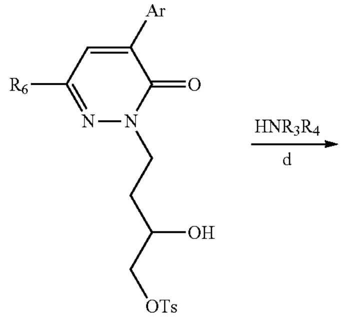

32

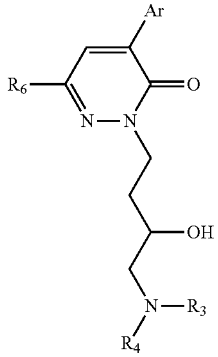

33

Conditions: a) NaH, DMF, 0° C., 30 min, then 18, 0° C. → 25° C., overnight; b) 1N HCl, 25° C., 2 h; c) $Bu_2SnO$ (4 mol %), TSCl, $Et_3N$, DCM, 25° C., 16 h; d) $NHR_3R_4$, $K_2CO_3$, KI, MeCN, 80° C., 16 h.

2-(3,4-dihydroxybutyl)-4-phenylpyridazin-3(2H)-one 31a

The reaction was performed in anhydrous conditions under argon atmosphere. To a solution of 4-phenylpyridazin-3(2H)-one 1 (172.2 mg, 0.93 mmol, 1 equiv.) in dry DMF (3.6 mL) cooled to 0° C. was added portionwise NaH (44.6 mg, 1.86 mmol, 2.0 equiv.) and the mixture was stirred at 0° C. for 30 min. Then, 2-(2,2-Dimethyl-1,3-dioxolan-4-yl) ethyl methanesulfonate 30[ref] (250 mg, 1.11 mmol, 1.2 equiv.) was added dropwise at 0° C. and the mixture was allowed to warm up to rt and stirred overnight. The mixture was quenched with $H_2O$ (15 mL) and extracted twice with EtOAc (2×15 mL). The combined organic layers were washed with brine, dried over $Na_2SO_4$, filtered and concentrated to dryness. The crude was then dissolved in THF and 1N HCl (5.2 ml, 10 equiv.) was added and the resulting mixture was stirred for 2 hours at 25° C. After evaporation to dryness the residue was purified by silica gel flash chromatography using Heptane/EtOAc (6/4) as eluent. The title compound was obtained (masse=130 mg, yield=57%).

$^1H$ NMR (400 MHz, $CDCl_3$) δ 7.92 (d, J=4.2 Hz, 1H), 7.80-7.71 (m, 2H), 7.50-7.41 (m, 3H), 7.33, (d, J=4.2 Hz, 1H), 4.72 (ddd, J=13.0 Hz, J=10.1 Hz, J=4.8 Hz, 1H), 4.18 (ddd, J=13.2 Hz, J=5.1 Hz, J=4.1 Hz, 1H), 3.67-3.57 (m, 2H), 3.56-3.48 (m, 1H), 3.21 (bs, OH), 2.03-1.94 (m, 1H), 1.91-1.81 (m, 1H).

[Ref] Eur. J. Org. Chem., 2015(27), 6075-6083; 2015

2-hydroxy-4-(6-oxo-5-phenylpyridazin-1(6H)-yl) butyl 4-methylbenzenesulfonate 32a To a solution of 2-(3,4-dihydroxybutyl)-4-phenylpyridazin-3(2H)-one 31a (148 mg, 0.57 mmol, 1 equiv.) in DCM (5.2 mL) were added $Bu_2SnO$ (5.7 mg, 0.02 mmol, 0.04 equiv), p-TsCl (195.1 mg, 1.02 mmol, 1.8 equiv), and $Et_3N$ (103.6 mg, 142 μL, 1.02 mmol, 1.8 equiv.). The reaction mixture was stirred until TLC indicated complete consumption of the starting material (about 16 h). The mixture was filtered, and the filtrate was concentrated in vacuo. The crude was purified by silica gel flash chromatography pretreated with $Et_2O/Et_3N$: 95/5. Using EtOAc/Heptane: 4/1, the title compound was obtained (masse=138 mg, 59%).

$^1H$ NMR (400 MHz, $CDCl_3$) δ 7.87 (d, J=4.2 Hz, 1H), 7.77-7.71 (m, 4H), 7.45-7.38 (m, 3H), 7.33-7.27 (m, 3H), 4.63 (ddd, J=13.3 Hz, J=10.4 Hz, J=4.5 Hz, 1H), 4.13 (ddd, J=13.5 Hz, J=5.3 Hz, J=4.4 Hz, 1H), 3.97 (d, J=5.3 Hz, 2H, 1H), 3.78-3.70 (m, 1H), 2.40 (s, 3H), 2.10-2.00 (m, 1H), 1.79 (ddt, J=14.2 Hz, J=10.6 Hz, J=4.4 Hz, 1H). $^{13}C$ NMR (101 MHz, $CDCl_3$) δ 161.0, 144.9, 139.9, 137.3, 133.5, 132.7, 129.9, 129.8, 128.7, 128.5, 128.0, 127.9, 73.1, 65.9, 48.7, 32.5, 21.7.

Example A-7: 2-(4-(benzyl(methyl)amino)-3-hydroxybutyl)-4-phenylpyridazin-3(2H)-one, 33a Using the same procedure described for 10d and starting from 2-hydroxy-4-(6-oxo-5-phenylpyridazin-1(6H)-yl) butyl 4-methylbenzenesulfonate 32a (30 mg, 0.072 mmol, 1 equiv.) and N-methylbenzylamine (17.54 mg, 18.7 μL, 0.14 mmol, 2.0 equiv.), NaI (1.0 mg, 0.1 equiv.), $K_2CO_3$ (24.0 mg, 0.17 mmol, 2.4 equiv.), the title compound was obtained after salification and lyophilization (masse=8.0 mg, yield=30%).

$^1H$ NMR (400 MHz, $CDCl_3$) δ 7.85 (d, J=4.2 Hz, 1H), 7.82-7.76 (m, 2H), 7.47-7.40 (m, 3H), 7.34-7.21 (m, 6H), 4.48 (dt, J=12.9 Hz, J=7.5 Hz, 1H), 4.37 (ddd, J=12.9 Hz, J=7.8 Hz, J=5.4 Hz), 3.82-3.75 (m, 1H), 3.65 (d, J=13.0 Hz, 1H), 3.49 (d, J=13.1 Hz, 1H), 2.49 (dd, J=12.1 Hz, J=9.6 Hz, 1H), 2.4 (dd, J=12.3 Hz, J=3.7 Hz, 1H), 2.24 (S, 3H), 2.07-1.99 (m, 1H), 1.90-1.81 (m, 1H). $^{13}C$ NMR (101 MHz, $CDCl_3$) δ 160.3, 139.7, 136.4, 134.0, 129.5, 129.0, 128.7, 128.4, 128.3, 127.5, 127.2, 64.9, 63.0, 62.5, 49.8, 42.2, 33.7.

LC/MS (M+H)=364.12

General Methods and Examples Deriving from Pyridones, Pyrimidones.

Alternatively, the pyridazinone ring can be replaced by a pyridone or pyrimidone ring of general formula 40 and 41, in a similar 4-step sequence following pathways 1 or 2 as depicted in scheme 7.

Scheme 8

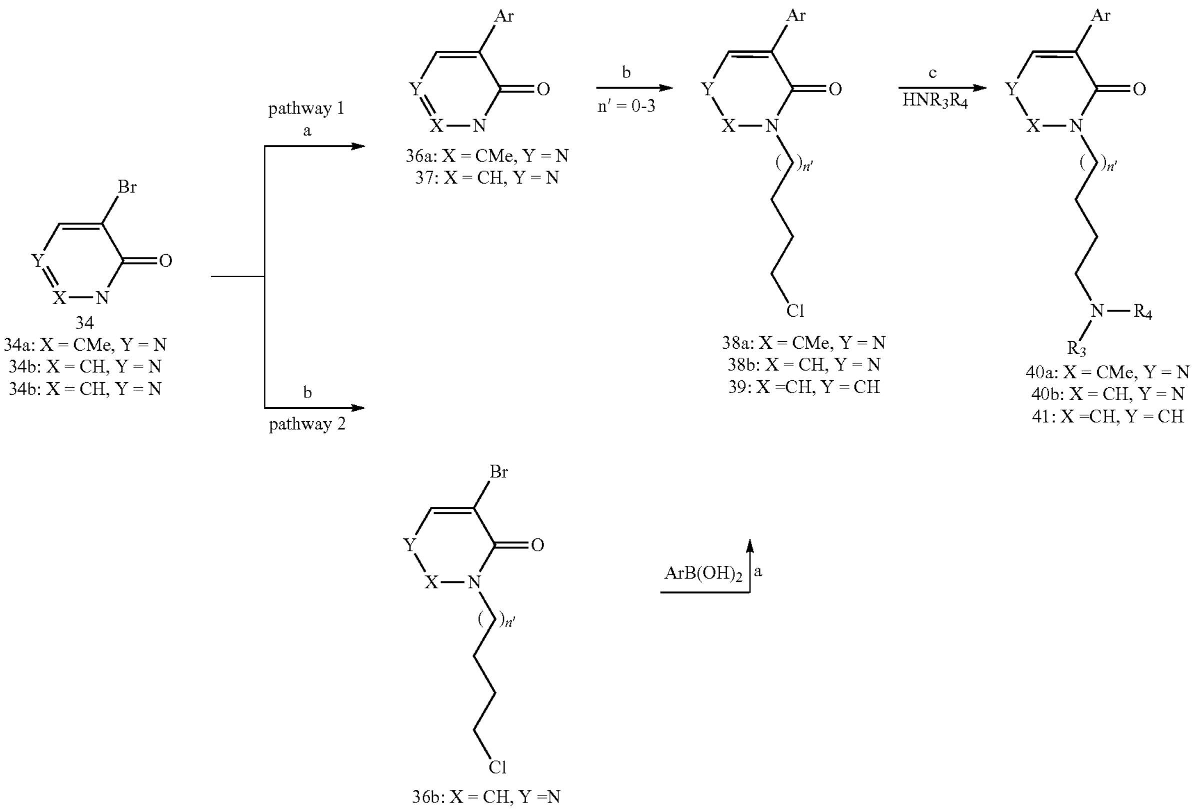

Conditions: a) $Na_2CO_3$, $Pd(PPh_3)_4$, DME, $H_2O$, μwaves, 100° C., 30 min. b) $Br(CH_2)_{n'+3}$—Cl, $K_2CO_3$, MeCN, 25° C., overnight. C) $HNR_3R_4$, $K_2CO_3$, NaI, MeCN, 80° C., 16 h.

2-methyl-5-phenylpyrimidin-4-ol 36a

A microwave vial (oven-dried and under argon) was charged with phenylboronic acid (257.4 mg, 2.12 mmol, 2.0 equiv.), 2-methyl-5-bromopyrimidin-4-ol 34a (200 mg, 1.06 mmol, 1.0 equiv.), sodium carbonate (148 mg, 1.40 mmol, 1.3 equiv.). Tetrakis(triphenylphosphine) palladium(0) (61.3 mg, 5 mol %) was then added, followed by DME (4.2 mL) and $H_2O$ (1.4 mL). The vial was properly capped and the mixture vessel was evacuated and backfilled with argon (process repeated 3 times), and heated under microwaves irradiation at 100° C. until complete conversion of the starting material. The reaction conversion was monitored by HPLC and was usually completed within 30 min. After cooling to room temperature, the reaction mixture was evaporated to dryness. The crude was partitioned through DCM (20 mL) and $H_2O$ (15 mL). The aqueous phase was extracted twice with DCM (10 mL). The organic phases were combined, washed with brine and dried ($Na_2SO_4$) and evaporated. The crude material was purified by silica gel chromatography using DCM/MeOH 95:5 as eluent to yield the title compound (masse=120 mg, yield=61%).

$^1$H NMR (400 MHz, $CDCl_3$) δ 13.27 (bs, 1H), 7.96 (s, 1H), 7.53-7.49 (m, 2H), 7.29-7.16 (m, 3H), 2.33 (s, 3H).

5-bromo-3-(4-chlorobutyl)-3,4-dihydropyrimidin-4-one 36b

The reaction was performed in anhydrous conditions under argon atmosphere. To a solution of 5-bromopyrimidin-4-ol (100 mg, 0.57 mmol, 1.0 equiv.) in dry MeCN (3.1 mL) was added 1-bromo-4-chlorobutane (196 mg, 1.14 mmol, 2 equiv.), $K_2CO_3$ (158 mg, 1.14 mmol, 2 equiv.) and the mixture was stirred at 80° C. overnight. The mixture was quenched with $H_2O$ (5 mL) and extracted with EtOAc (2×5 mL). The combined organic layers were washed with brine, dried over $Na_2SO_4$, filtered and concentrated to dryness. The crude was purified by column chromatography over silica gel (solid loading, eluent: Heptane/EtOAc: 3/1 to 1/1) to give the title compound (masse=47 mg, yield=31%).

$^1$H NMR (400 MHz, $CDCl_3$) δ 8.17 (s, 1H), 8.04 (s, 1H), 3.98 (t, J=7.3 Hz, 2H), 3.55 (t, J=6.3 Hz, 2H), 1.97-1.88 (m, 2H), 1.85-1.76 (m, 2H). $^{13}$C NMR (101 MHz, $CDCl_3$): δ 157.8, 153.9, 150.0, 114.4, 47.6, 44.0, 29.3, 26.5.

3-phenylpyridin-2-ol 37

Using the same procedure described for 36a and starting from 3-bromopyridin-2-ol 35 (400 mg, 2.23 mmol, 1.0 equiv), phenylboronic acid (336.4 mg, 2.76 mmol, 1.2 equiv.) and potassium carbonate (490.0 mg, 4.60 mmol, 2 equiv.), the title compound was obtained after purification by silica gel chromatography using a gradient of gradient of 50 to 80% of EtOAc in heptane to give the title compound as a white solid (masse=183 mg, yield=46%).

$^1$H NMR (400 MHz, $CDCl_3$) δ 12.93 (br s, 1H), 7.69 (d, J=7.3 Hz, 2H), 7.57 (dd, J=6.9, 2.0 Hz, 1H), 7.41 (t, J=7.5 Hz, 2H), 7.38-7.30 (m, 2H), 6.34 (t, J=6.7 Hz, 1H). $^{13}$C NMR (101 MHz, $CDCl_3$): δ 164.2, 139.9, 136.8, 134.0, 131.9, 128.8, 128.5, 128.0, 107.3.

3-(4-chlorobutyl)-2-methyl-5-phenyl-3,4-dihydropyrimidin-4-one 38a

To a solution of 2-methyl-5-phenylpyrimidin-4-ol 36a (110 mg, 0.59 mmol, 1 equiv.) in MeCN (4.4 mL) were added $K_2CO_3$ (245 mg, 1.77 mmol, 3 equiv.) and 1-bromo-4-chlorobutane (304 mg, 1.77 mmol, 3 equiv.) and the resulting mixture was stirred at room temperature under argon overnight. The reaction mixture was then evaporated to dryness. The crude was partitioned through EtOAc (20 mL) and $H_2O$ (15 mL). The aqueous phase was extracted twice with EtOAc (10 mL). The organic phases were combined, washed with brine and dried ($Na_2SO_4$) and evaporated. The crude material was purified by silica gel chromatography using DCM as eluent. (masse=55 mg, yield=34%).

$^1$H NMR (400 MHz, $CDCl_3$) δ 7.94 (s, 1H), 7.63-7.60 (m, 2H), 7.41-7.30 (m, 3H), 4.12 (t, J=6.1 Hz, 2H), 3.61 (t, J=6.1 Hz, 2H), 2.63 (s, 3H), 1.94-1.91 (m, 4H). $^{13}$C NMR (101 MHz, $CDCl_3$) δ 166.8, 165.8, 156.4, 133.5, 129.0, 128.6, 128.1, 119.1, 85.7, 44.7, 29.4, 26.3, 25.9.

3-(4-chlorobutyl)-5-phenyl-3,4-dihydropyrimidin-4-one 38b

Using the same procedure than described for preparation of compound 18a and starting from 5-bromo-3-(4-chlorobutyl)-3,4-dihydropyrimidin-4-one 36b (47 mg, 0.18 mmol, 1.0 equiv.) and phenylboronic acid (43.2 mg, 0.35 mmol, 2 equiv.) the title compound was obtained (masse=44.6 mg, yield=96%). $^1$H NMR (400 MHz, $CDCl_3$) δ 8.08 (s, 1H), 8.03 (s, 1H), 7.66-7.61 (m, 2H), 7.41-7.33 (m, 3H), 3.99 (t, J=7.3 Hz, 2H), 3.55 (t, J=6.3 Hz, 2H), 2.00-1.90 (m, 2H), 1.87-1.78 (m, 2H).

1-(4-chlorobutyl)-3-phenyl-1,2-dihydropyridin-2-one 39

Using the same procedure described for 38a and starting from 3-phenylpyridin-2-ol (100 mg, 0.58 mmol, 1 equiv.) and 1-bromo-4-chlorobutane (300.5 mg, 1.75 mmol, 3 equiv.), the title compound was obtained as an opaque oil (masse=84.3 mg, yield=55%). $^1$H NMR (400 MHz, $CDCl_3$) δ 7.68-7.63 (m, 2H), 7.46 (dd, J=6.9 Hz, J=2.2 Hs), 1H), 7.40-7.35 (m, 2H), 7.32-7.29 (m, 1H), 7.26 (dd, J=6.7 Hz, J=2.1 Hz, 1H), 4.02 (t, J=7.1 Hz, 2H), 3.56 (t, J=6.4 Hz, 2H), 1.99-1.90 (m, 2H), 1.89-1.80 (m, 2H). $^{13}$C NMR (101 MHz, $CDCl_3$) δ 161.5, 137.5, 136.8, 136.5, 132.0, 128.7, 128.1, 127.7, 49.3, 44.5, 29.5, 26.5.

Example A-8:2-methyl-3-(4-morpholinobutyl)-5-phenylpyrimidin-4(3H)-one 40 a

Using the same procedure described for 9b and starting from 3-(4-chlorobutyl)-2-methyl-5-phenyl-3,4-dihydropyrimidin-4-one 39 (63 mg, 0.23 mmol, 1 equiv.) and morpholine (49.6 mg, 50.1 µl, 0.57 mmol, 2.5 equiv.), NaI (0.9 mg, 0.023 mmol, 0.1 equiv), $K_2CO_3$ (62.9 mg, 0.45 mmol, 2.0 equiv.), the title compound was obtained (masse=44 mg, yield=59%). Salification and lyophilization led to the corresponding hydrochloride salt.

$^1$H NMR (400 MHz, $CDCl_3$) δ 7.93 (s, 1H), 7.64-7.58 (m, 2H), 7.41-7.29 (m, 3H), 4.10-4.05 (m, 2H), 3.70 (dd, J=5.3 Hz, J=4.3 Hz, 4H), 2.50-2.37 (m, 6H), 1.76 (quin, J=8.0 Hz, 2H), 1.62 (quin, J=7.4 Hz, 2H).

$^{13}$C NMR (101 MHz, $CDCl_3$) δ 161.3, 158.3, 149.9, 133.7, 128.6, 128.5, 128.3, 124.9, 66.9, 58.2, 53.8, 45.1, 26.2, 23.8, 23.2.

LC/MS (M+H)=328.20

3-[4-(morpholin-4-yl)butyl]-5-phenyl-3,4-dihydropyrimidin-4-one 40b

Using the same procedure described for 9b and starting from 3-(4-chlorobutyl)-5-phenyl-3,4-dihydropyrimidin-4-one 38b (44 mg, 0.16 mmol, 1 equiv.) and morpholine (72.9 mg, 73.7 µl, 083 mmol, 5.0 equiv.), NaI (2.5 mg, 0.016 mmol, 0.1 equiv), $Na_2CO_3$ (35.7 mg, 0.34 mmol, 2.0 equiv.), the title compound was obtained (masse=34 mg, yield=65%). Salification and lyophilization led to the corresponding hydrochloride salt.

$^1$H NMR (400 MHz, $CDCl_3$) δ 8.03 (s, 1H), 7.98 (s, 1H), 7.61-7.57 (m, 2H), 7.38-7.33 (m, 2H), 7.32-7.28 (m, 1H), 3.95 (t, J=7.3 Hz, 2H), 3.64 (t, J=4.6 Hz, 4H), 2.39-2.29 (m, 6H), 1.82-165 (m, 2H), 1.55-1.47 (m, 2H). $^{13}$C NMR (101 MHz, $CDCl_3$) δ 160.3, 150.7, 149.9, 133.0, 128.5, 128.4, 128.3, 127.7, 66.7, 58.2, 53.6, 47.6, 27.0, 23.2.

LC/MS (M+H)=314.19

1-[4-(morpholin-4-yl)butyl]-3-phenyl-1,2-dihydropyridin-2-one, 41a

Using the same procedure described for 9b and starting from 1-(4-chlorobutyl)-3-phenyl-1,2-dihydropyridin-2-one 36b (84 mg, 0.32 mmol, 1 equiv.) and morpholine (139.8 mg, 141 µl, 1.60 mmol, 5 equiv.), NaI (4.8 mg, 0.032 mmol, 0.1 equiv), $Na_2CO_3$ (68.0 mg, 0.64 mmol, 2.0 equiv.), the title compound was obtained (masse=84.3 mg, yield=84%). Salification and lyophilization led to the corresponding hydrochloride salt.

$^1$H NMR (400 MHz, $CDCl_3$) δ 7.67-7.63 (m, 2H), 7.45 (dd, J=6.9 Hz, J=2.1 Hz, 1H), 7.40-7.34 (m, 2H), 7.32-7.27 (m, 1H), 7.25 (dd, J J=6.9 Hz, J=2.1 Hz, 1H), 4.0 (t, J=7.6 Hz), 3.68 (J=4.8 Hz), 2.45-2.32 (m, 6H), 1.81 (quint, J=7.5 Hz, 2H), 1.55 (quint, J=7.7 Hz, 2H). $^{13}$C NMR (101 MHz, $CDCl_3$) δ 161.3, 106.0, 137.4, 136.9, 136.6, 131.9, 128.6, 128.1, 127.6, 67.0, 58.1, 53.6, 50.2, 27.0, 23.7.

LC/MS (M+H)=313.19

1-{4-[benzyl(methyl)amino]butyl}-3-phenyl-1,2-dihydropyrazin-2-one 41b

Using the same procedure described for 9b and starting from 1-(4-chlorobutyl)-3-phenyl-1,2-dihydropyridin-2-one 36b (38 mg, 0.14 mmol, 1 equiv.) and N-methylbenzylamine (26.4 mg, 28 µl, 0.22 mmol, 1.5 equiv.), NaI (2.2 mg, 0.014 mmol, 0.1 equiv), $Na_2CO_3$ (23.1 mg, 0.22 mmol, 1.5 equiv.), the title compound was obtained (masse=32.7 mg, yield=65%). Salification and lyophilization led to the corresponding hydrochloride salt.

$^1$H NMR (400 MHz, $CDCl_3$) δ 7.58-7.56 (m, 2H), 7.38 (dd, J=6.8, 1.9 Hz, 1H), 7.32-7.18 (m, 9H), 6.18 (t, J=6.9 Hz, 1H), 3.91 (t, J=7.1 Hz, 2H), 3.66 (s, 2H), 2.57 (t, J=7.2 Hz, 2H), 2.28 (s, 3H), 1.75 (quin, J=7.2 Hz, 2H), 1.69-1.61 (m, 2H). 13C NMR (101 MHz, CDCl3) δ 161.6, 137.8, 137.0, 136.9, 135.0, 131.9, 130.1, 128.9, 128.8, 128.4, 128.2, 127.8, 103.3, 61.6, 56.1, 50.1, 41.2, 26.9, 23.4.

LC/MS (M+H)=347.15

General Methods and Examples Deriving from Pyrazinones

Alternatively, the pyridazinone ring can be replaced by a pyrazinone ring as depicted in scheme 8. Starting from 2,3-$Cl_2$-pyrazine a Suzuki Miyaura reaction with the help of $Pd(PPh_3)_4$, followed by treatment with HCl let to the key intermediate 3-phenylpyrazin-2-ol 44. Alkylation of 44 with 1-bromo-4-chlorobutane in presence of NaH in DMF led to intermediates 45. Finally a nucleophilic substitution reaction was performed with appropriate aliphatic amines $NHR_3R_4$ leading to compounds of general formula 46.

Scheme 9

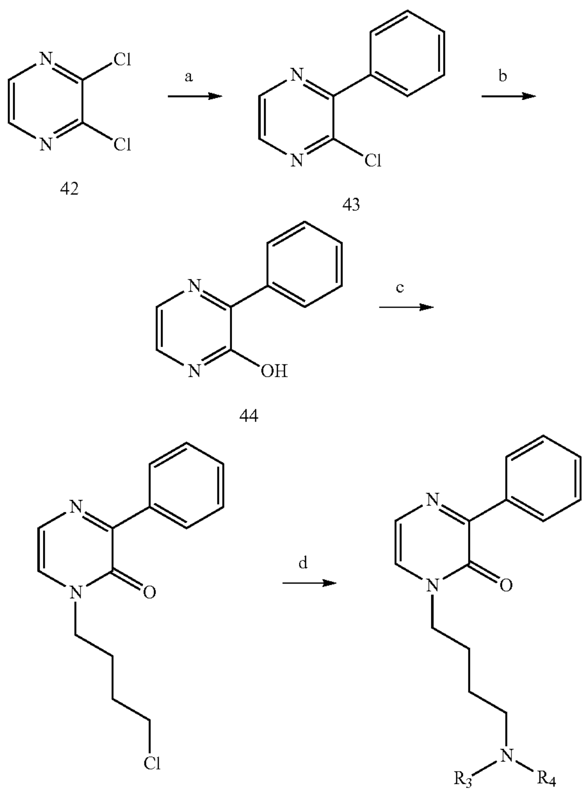

42 43 44 45 46

Conditions: a) $ArB(OH)_2$, $Na_2CO_3$, $Pd(PPh_3)_4$, DME/$H_2O$, 85° C., 16 h; b) HCl 15%, 85° C., 5 h. c) NaH, $Br(CH_2)_4Cl$, RT, 3 h; d) $HNR_3R_4$, $Na_2CO_3$, NaI cat, MeCN, 80° C., 16 h.

2-chloro-3-phenylpyrazine 43

A microwave vial (oven-dried and under argon) was charged with 4 2,3-dichloropyrazine 42 (116 mg, 0.78 mmol, 1.0 equiv.), phenylboronic acid (94.9 mg, 0.78 mmol, 1.0 equiv.), $Na_2CO_3$ (82.9 mg, 0.78 mmol, 1.0 equiv.). Tetrakis(triphenylphosphine)palladium (45.4 mg, 5 mol %) was then added, followed by DME (2.7 mL) and water (1.16 mL). The vial was properly capped and the mixture vessel was evacuated and backfilled with argon (process repeated 3 times) and heated at 85° for 16 hours. The crude was partitioned through EtOAc (30 mL) and $H_2O$ (50 mL). The aqueous phase was extracted twice with EtOAc (20 mL). The organic phases were combined, washed with brine and dried ($Na_2SO_4$) and evaporated. The crude material was purified by flash chromatography using Hept/EtOAc: 6/1 as eluent to give the title compound 43 (masse=84.0 mg, yield=57%).

$^1H$ NMR (400 MHz, $CDCl_3$) δ 8.61 (d, J=2.4 Hz, 1H), 8.36 (d, J=2.4 Hz, 1H), 7.81-7.79 (m, 2H), 7.50-7.44 (m, 3H).

3-phenylpyrazin-2-ol 44

2-chloro-3-phenylpyrazine (57 mg, 0.3 mmol) was suspended in HCL 15% (6 mL) and the resulting mixture was heated under reflux for 5 hours. After cooling the solution was treated with NaOH 2N until pH reached approximately 5-6. The aqueous layer was then extracted with DCM (3×). The organic phases were collected, dried over $Na_2SO_4$, filtered and the solvent removed in vacuo to yield a white solid (m=46 mg, yield=89%). The solid was used in the next step without further purification.

$^1H$ NMR (400 MHz, $CDCl_3$) δ 13.24 (broad s, 1H) 8.12-8.06 (m, 2H), 7.43 (d, J=4.0 Hz, 1H), 7.30-7.22 (m, 3H), 7.02 (d, J=4.0 Hz, 1H). $^{13}C$ NMR (101 MHz, $CDCl_3$) δ 157.7, 153.8, 135.7, 130.1, 128.8, 128.2, 125.1, 124.8.

1-(4-chlorobutyl)-3-phenyl-1,2-dihydropyrazin-2-one 45

The reaction was performed in anhydrous conditions under argon atmosphere. To a solution of 3-phenylpyrazin-2-ol 44 (45 mg, 0.26 mmol, 1 equiv.) in dry DMF (0.9 mL) cooled to 0° C. was added portionwise NaH (1.5 eq., 9.4 mg, 0.39 mmol, 1.5 equiv.) and the mixture was stirred at 0° C. for 30 min. Then, 1-bromo-4-chlorobutane (134.4 mg, 91 μL, 0.78 mmol, 3.0 equiv.) was added at 0° C. and the mixture was allowed to warm up to rt and stirred for 3 h. The mixture was quenched with $H_2O$ (5 mL) and extracted with EtOAc (2×5 mL). The combined organic layers were washed with brine, dried over $Na_2SO_4$, filtered and concentrated to dryness. The crude was purified by column chromatography over silica gel (solid loading, eluent: Heptane/EtOAc: 1/2) to give the title compound (masse=25.6 mg, yield=37%).

$^1H$ NMR (400 MHz, $CDCl_3$) δ 8.15-8.07 (m, 2H), 7.30-7.23 (m, 1H), 6.94 (d, J=4.2 Hz, 1H), 3.84 (t, J=7.3 Hz, 2H), 3.42 (t, J=6.3 Hz, 2H), 1.86-1.77 (m, 2H), 1.73-1.65 (m, 2H). $^{13}C$ NMR (101 MHz, $CDCl_3$) δ 155.5, 153.7, 135.9, 129.9, 129.0, 128.0, 127.7, 123.4, 49.2, 44.2, 29.4, 26.1.

Example A-9: 1-[4-(morpholin-4-yl)butyl]-3-phenyl-1,2-dihydropyrazin-2-one 46a

Using the same procedure described for 9b and starting from 1-(4-chlorobutyl)-3-phenyl-1,2-dihydropyrazin-2-one 45 (25.6 mg, 0.97 mmol, 1 equiv.) and morpholine (42.4 mg, 42.9 μl, 0.48 mmol, 2.5 equiv.), NaI (1.5 mg, 0.001 mmol, 0.1 equiv), $Na_2CO_3$ (20.8 mg, 0.19 mmol, 2.0 equiv.), the title compound was obtained (masse=22.9 mg, yield=75%). Salification and lyophilization led to the corresponding hydrochloride salt.

$^1H$ NMR (400 MHz, $CDCl_3$) δ 8.31-8.20 (m, 2H), 7.45-7.34 (m, 4H), 7.08 (d, J=4.2 Hz), 3.96 (t, J=7.3 Hz, 2H), 3.67 (t, J=4.9 Hz), 2.43-2.30 (m, 6H), 1.82 (quint., J=7.5 Hz, 2H), 1.54 (m, J=7.4 Hz, 2H). $^{13}C$ NMR (101 MHz, $CDCl_3$) δ 155.5, 153.2, 136.1, 129.8, 128.9, 128.0, 127.8, 123.3, 66.9, 58.0, 53.0, 49.9, 26.5, 23.5.

LC/MS (M+H)=314.18

Part B. In Vitro Pharmacology: Binding Assays

Binding Assay to σ1 Receptor

The σ1 binding assays were performed according to Ganapathy et al (Ganapathy, M. E. et al. (1999), J. Pharmacol. Exp. Ther., 28:251-260). The σ1 binding assay was carried out by incubating Jurkat cell membranes (10-20 mg protein per tube) with [$^3$H](+) pentazocine a selective S1R ligand (15 nM) and a range of concentration of tested compounds, at 37° C. for 2 hours in 5 mM tris/HCl buffer (pH=7.4). The inhibition of [3H]-(+)-pentazocine binding assay is mainly used to determine the inhibition constant (Ki) of potential SIR ligands. These assays are performed with a single concentration of [$^3$H]-(+)-pentazocine at a concentration near its $K_D$ and increasing concentrations of non-radioactive ligands.

TABLE 1

| Assay | Source | Ligand | Conc | Kd | Non specific | Incubation | Detection method |
|---|---|---|---|---|---|---|---|
| Receptors | | | | | | | |
| sigma 1 (h) (agonist radioligand) | Jurkat cell (endogenous | [3H] (+)pentazocine | 15 nM | 16 nM | haloperidol (10 μM) | 120 min 37° C. | Scintillation counting |
| sigma 1 (h) (agonist radioligand) | Jurkat cells (endogenous) | [3H] DTG (+1 μM (+) Pentazocine) | 25 nM | 80.84 nM | Haloperidol (10 μM) | 60 min RT | Scintillation counting |

TABLE 2

| | Sigma-1 receptor % inhibition | |
|---|---|---|
| No | 100 nM | 10 nM |
| 9a | | 61.5 |
| 9b | | 47.4 |
| 9c | | 7.6 |
| 10a | | 87.5 |
| 10b | | 14.5 |
| 10c | 80.3 | 40.3 |
| 10d | | 28.3 |
| 10e | | 30.2 |
| 10f | | 70 |
| 10g | | 73.5 |
| 10h | | 70.8 |
| 10i | | 37.1 |
| 10j | | 4.9 |
| 10k | | 3.7 |
| 10m | | 28.8 |
| 10o | 68.3 | 25.6 |
| 10p | 9.7 | |
| 10q | 79.6 | 29.4 |
| 10r | 92.1 | 78.7 |
| 10s | | 64.6 |
| 10t | 38.2 | 9.7 |
| 10u | 26.5 | |
| 10w | 79.4 | 37.6 |
| 10x | 76.2 | 34.6 |
| 10z | | 64.2 |
| 11a | | 83.4 |
| 11b | | 73.9 |
| 11d | | 16.1 |
| 11e | | 7.4 |
| 11h | | 12 |
| 11k | | 1.9 |
| 11l | | 69.1 |
| 11m | | 5.04 |
| 11n | | 6.13 |
| 11o | | 33.4 |
| 11p | | 15.6 |
| 11v | 86.0 | |
| 11w | 53.9 | |
| 14 | | 2.1 |
| 16 | | 4.8 |
| 21a | | 1.1 |
| 25a | | 15.8 |
| 33a | | 12.3 |
| 40a | | 1.4 |
| 40b | | 1.4 |
| 41a | | 3.0 |

The invention claimed is:

1. A compound having the following formula (I):

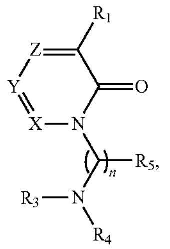

(I)

wherein:

$R_1$ represents:

an aryl($C_1$-$C_6$)alkyl group;

an aryl($C_2$-$C_6$)alkenyl group;

an aryl group;

a heteroaryl group;

a heterocycle group;

a cycloalkyl group; or a -QR group, with Q being O or S, and R being alkyl, aryl or aralkyl;

said group being optionally substituted by at least one-OH, halogen, ($C_1$-$C_6$)alkyl optionally substituted by one or more fluorine atoms, or ($C_1$-$C_6$) alkyloxy;

Z represents $CR_2$;

$R_2$ represents H, a ($C_1$-$C_4$)alkyl or a phenyl group;

X and Y are N and $CR_6$ respectively;

$R_6$ is H or a ($C_1$-$C_4$)alkyl group;

n is 3, 4, 5, or 6;

$R_3$ and $R_4$:

represent independently a radical selected from a hydrogen atom, a ($C_1$-$C_6$)alkyl, ($C_2$-$C_6$)alkenyl, cycloalkyl, heterocycle, aryl, heteroaryl, and aryl ($C_1$-$C_6$)alkyl, said radical being optionally substituted by at least one substituent selected from the group consisting of a hydroxy, a ($C_1$-$C_6$)alkyl, a ($C_1$-$C_6$)alkoxy, a cycloalkyl, a heterocycle, an aryl, and a heteroaryl; or form, together with the nitrogen to which they are bound, a nitrogen-based heterocycle, said nitrogen-based heterocycle being optionally substituted by at least one substituent selected from the group consisting of a hydroxy, oxo, ($C_1$-$C_6$)alkyl, ($C_2$-$C_6$) alkenyl, cycloalkyl, aryl, heteroaryl, heterocycle, aryl ($C_1$-$C_6$)alkyl, hydroxy($C_1$-$C_6$)alkyl, and said nitrogen-based heterocycle being optionally fused with at least one 5-14 membered ring selected from aryl and heteroaryl;

each of $R_5$ represents independently H, OH, or a ($C_1$-$C_4$) alkyl group; and wherein the heteroaryl group and heteroaryl comprise independently between 5 and 14 atoms and comprise one or two heteroatoms independently selected from the group consisting of nitrogen, oxygen and sulfur and the heterocycle group and heterocycle are independently a saturated or unsaturated mono-, bi- or tricyclic alkyl group having between 3 and 20 atoms of carbons atoms and comprising one or two heteroatoms independently selected from the group consisting of nitrogen, oxygen and sulfur;

a stereoisomer, a solvate or any pharmaceutical salt thereof.

2. The compound according to claim 1, wherein $R_1$ represents:

an aryl group;

a heteroaryl;

a heterocycle; or a group selected from cyclohexenyl, phenethyl, phenethenyl, —OPh, and —SPh.

3. The compound according to claim 1, wherein $R_2$ represents H.

4. The compound according to claim 1, wherein Y is CH.

5. The compound according to claim 1, wherein n is 4.

6. The compound according to claim 1, wherein $R_3$ and $R_4$:

represent independently a radical selected from:

a hydrogen atom, a $(C_1-C_6)$alkyl, a cycloalkyl, and an aryl$(C_1-C_6)$alkyl, said radical being optionally substituted by one or two substituents independently selected from the group consisting of:

a hydroxy, a $(C_1-C_6)$alkoxy, a heterocycle; and an aryl; or form together with the nitrogen to which they are bound a nitrogen-based heterocycle, said nitrogen-based heterocycle being optionally substituted by at most three substituents independently selected from the group consisting of:

hydroxy, oxo, $(C_1-C_6)$alkyl, aryl, aryl$(C_1-C_6)$alkyl, hydroxy$(C_1-C_6)$alkyl, and said nitrogen-based heterocycle being optionally fused with one aryl group.

7. The compound according to claim 1, wherein $R_3$ and $R_4$ form, together with the nitrogen to which they are bound, a nitrogen-based heterocycle, said nitrogen-based heterocycle being represented by the following formula (II):

(II)

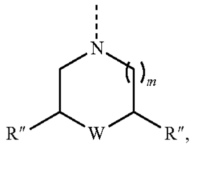

wherein m is 1 or 2;

W represents O, S, NR', $(CH_2)_2$, or CHR';

R' represents a hydrogen atom, $(C_1-C_6)$alkyl, aryl, or aryl$(C_1-C_6)$alkyl; and each R" represents independently a hydrogen atom, hydroxy, oxo, $(C_1-C_6)$alkyl, aryl, aryl$(C_1-C_6)$alkyl, or hydroxy$(C_1-C_6)$alkyl.

8. The compound according to claim 1, wherein:

$R_1$ is an aryl group;

said aryl group being optionally substituted by at least one halogen;

$R_2$ is H; and $R_5$ is H.

9. The compound according to claim 1, wherein at least one of the following features is fulfilled:

n is 4; and/or $R_6$ is H or methyl; and/or $R_1$ represents an aryl group optionally substituted by at least one —OH, halogen, $(C_1-C_6)$alkyl optionally substituted by one or more fluorine atoms, or $(C_1-C_6)$alkyloxy; and/or $R_2$ represents H, methyl or phenyl; and/or $R_3$ and $R_4$ represent independently a radical selected from:

a hydrogen atom, a $(C_1-C_6)$alkyl, a cycloalkyl, and an aryl$(C_1-C_6)$alkyl, said radical being optionally substituted by one or two substituents independently selected from the group consisting of:

a hydroxy, a $(C_1-C_6)$alkoxy, a heterocycle; and an aryl; or form together with the nitrogen to which they are bound a nitrogen-based heterocycle, said nitrogen-based heterocycle being optionally substituted by at most three substituents independently selected from the group consisting of:

hydroxy, oxo, $(C_1-C_6)$alkyl, aryl, aryl$(C_1-C_6)$alkyl, and hydroxy$(C_1-C_6)$alkyl, and said nitrogen-based heterocycle being optionally fused with one aryl group, and/or each $R_5$ is H;

and a pharmaceutical salt thereof.

10. The compound according to claim 1, wherein said compound is selected from the group consisting of:

2-(4-morpholinobutyl)-4-phenylpyridazin-3(2H)-one hydrochloride salt;

2-(3-(benzyl(methyl)amino)propyl)-4-phenylpyridazin-3(2H)-one;

2-(3-(azepan-1-yl)propyl)-4-phenylpyridazin-3(2H)-one;

2-[3-(morpholin-4-yl)propyl]-4-phenyl-2,3-dihydropyridazin-3-one;

2-(4-morpholinobutyl)-4-phenylpyridazin-3(2H)-one;

2-(4-(benzyl(methyl)amino)butyl)-4-phenylpyridazin-3(2H)-one;

2-(4-(1,4-oxazepan-4-yl)butyl)-4-phenylpyridazin-3(2H)-one;

4-phenyl-2-(4-(piperidin-1-yl)butyl)pyridazin-3(2H)-one;

2-(4-(azepan-1-yl)butyl)-4-phenylpyridazin-3(2H)-one;

2-(4-(azocan-1-yl)butyl)-4-phenylpyridazin-3(2H)-one;

2-(4-(3,4-dihydroisoquinolin-2(1H)-yl)butyl)-4-phenylpyridazin-3(2H)-one;
4-phenyl-2-(4-(1,2,4,5-tetrahydro-3H-benzo[d]azepin-3-yl)butyl)pyridazin-3(2H)-one;
2-(4-(adamantan-1-ylamino)butyl)-4-phenylpyridazin-3(2H)-one;
2-(4-(adamantan-1-yl(methyl)amino)butyl)-4-phenylpyridazin-3(2H)-one;
4-phenyl-2-(4-(1,3,3-trimethyl-6-azabicyclo[3.2.1]octan-6-yl)butyl)pyridazin-3(2H)-one;
8-(4-(6-oxo-5-phenylpyridazin-1(6H)-yl)butyl)-8-azabicyclo[3.2.1]octan-3-one;
2-(4-(benzyl((tetrahydrofuran-2-yl)methyl)amino)butyl)-4-phenylpyridazin-3(2H)-one;
2-(4-((2-methoxy-1-phenylethyl)amino)butyl)-4-phenylpyridazin-3(2H)-one;
2-(4-((2-methoxy-1-phenylethyl)(methyl)amino)butyl)-4-phenylpyridazin-3(2H)-one;
2-(4-((2-hydroxyethyl)(methyl)amino)butyl)-4-phenylpyridazin-3(2H)-one;
2-(4-(methyl((tetrahydro-2H-pyran-4-yl)methyl)amino)butyl)-4-phenylpyridazin-3(2H)-one;
4-phenyl-2-(4-(3-phenylpiperidin-1-yl)butyl)pyridazin-3(2H)-one;
4-phenyl-2-(4-(4-phenylpiperidin-1-yl)butyl)pyridazin-3(2H)-one;
2-(4-(3-(hydroxymethyl)piperidin-1-yl)butyl)-4-phenylpyridazin-3(2H)-one;
2-(4-(2-(2-hydroxyethyl)piperidin-1-yl)butyl)-4-phenylpyridazin-3(2H)-one;
4-phenyl-2-(4-(3-phenylmorpholino)butyl)pyridazin-3(2H)-one;
4-phenyl-2-(4-(2-phenylmorpholino)butyl)pyridazin-3(2H)-one;
2-(4-(2,6-dimethylmorpholino)butyl)-4-phenylpyridazin-3(2H)-one;
2-[4-(4-benzylpiperazin-1-yl)butyl]-4-phenyl-2,3-dihydropyridazin-3-one;
2-[4-(4-benzylpiperidin-1-yl)butyl]-4-phenyl-2,3-dihydropyridazin-3-one;
2-{4-[benzyl(ethyl)amino]butyl}-4-phenyl-2,3-dihydropyridazin-3-one;
2-{4-[cyclohexyl(methyl)amino]butyl}-4-phenyl-2,3-dihydropyridazin-3-one;
4-phenyl-2-[4-(4-phenylpiperazin-1-yl)butyl]-2,3-dihydropyridazin-3-one;
2-{4-[(4aR,8aS)-decahydroquinolin-1-yl]butyl}-4-phenyl-2,3-dihydropyridazin-3-one;
2-(4-{2-oxa-6-azaspiro [3.3] heptan-6-yl} butyl)-4-phenyl-2,3-dihydropyridazin-3-one;
4-phenyl-2-[4-(thiomorpholin-4-yl)butyl]-2,3-dihydropyridazin-3-one;
2-{4-[cyclohexyl(ethyl)amino]butyl}-4-phenyl-2,3-dihydropyridazin-3-one;
4-(4-fluorophenyl)-2-(4-morpholinobutyl)pyridazin-3(2H)-one;
4-(4-hydroxyphenyl)-2-(4-morpholinobutyl)pyridazin-3(2H)-one;
2-(5-morpholinopentyl)-4-phenylpyridazin-3(2H)-one;
2-[6-(morpholin-4-yl)hexyl]-4-phenyl-2,3-dihydropyridazin-3-one;
2-(4-(3-hydroxy-8-azabicyclo[3.2.1]octan-8-yl)butyl)-4-phenylpyridazin-3(2H)-one;
4-(4-methoxyphenyl)-2-[4-(morpholin-4-yl)butyl]-2,3-dihydro pyridazin-3-one;
4-(4-chlorophenyl)-2-[4-(morpholin-4-yl)butyl]-2,3-dihydropyridazin-3-one;
4-(3-chlorophenyl)-2-[4-(morpholin-4-yl)butyl]-2,3-dihydropyridazin-3-one;
4-(2-chlorophenyl)-2-[4-(morpholin-4-yl)butyl]-2,3-dihydropyridazin-3-one;
2-[4-(morpholin-4-yl)butyl]-4-[4-(trifluoromethyl)phenyl]-2,3-dihydropyridazin-3-one;
2-[4-(morpholin-4-yl)butyl]-4-(thiophen-3-yl)-2,3-dihydropyridazin-3-one;
4-(furan-3-yl)-2-[4-(morpholin-4-yl)butyl]-2,3-dihydropyridazin-3-one;
4-(3a,7a-dihydro-1-benzofuran-2-yl)-2-[4-(morpholin-4-yl)butyl]-2,3-dihydropyridazin-3-one;
2-[4-(morpholin-4-yl)butyl]-4-(pyridin-3-yl)-2,3-dihydropyridazin-3-one;
2-{4-[benzyl(methyl)amino]butyl}-6-methyl-4-phenyl-2,3-dihydropyridazin-3-one;
2-[4-(azepan-1-yl)butyl]-6-methyl-4-phenyl-2,3-dihydropyridazin-3-one;
2-[4-(morpholin-4-yl)butyl]-4-[(E)-2-phenylethenyl]-2,3-dihydropyridazin-3-one;
2-[4-(morpholin-4-yl)butyl]-4-(2-phenylethyl)-2,3-dihydropyridazin-3-one;
4-(cyclohex-1-en-1-yl)-2-[4-(morpholin-4-yl)butyl]-2,3-dihydropyridazin-3-one;
2-(4-morpholinobutyl)-4-(piperidin-1-yl)pyridazin-3(2H)-one;
2-[4-(morpholin-4-yl)butyl]-4-(1H-pyrrol-1-yl)-2,3-dihydropyridazin-3-one;
2-[4-(morpholin-4-yl)butyl]-4-(phenylsulfanyl)-2,3-dihydropyridazin-3-one;
2-[4-(morpholin-4-yl)butyl]-4-phenoxy-2,3-dihydropyridazin-3-one; and
2-(4-(benzyl(methyl)amino)-3-hydroxybutyl)-4-phenylpyridazin-3(2H)-one.

11. The compound according to claim 10, wherein said compound is selected from the group consisting of:
2-(3-(benzyl(methyl)amino)propyl)-4-phenylpyridazin-3(2H)-one;
2-(3-(azepan-1-yl)propyl)-4-phenylpyridazin-3(2H)-one;
2-(4-(benzyl(methyl)amino)butyl)-4-phenylpyridazin-3(2H)-one;
2-(4-(1,4-oxazepan-4-yl)butyl)-4-phenylpyridazin-3(2H)-one;
4-phenyl-2-(4-(piperidin-1-yl)butyl)pyridazin-3(2H)-one;
2-(4-(azepan-1-yl)butyl)-4-phenylpyridazin-3(2H)-one;
2-(4-(azocan-1-yl)butyl)-4-phenylpyridazin-3(2H)-one;
2-(4-(3,4-dihydroisoquinolin-2(1H)-yl)butyl)-4-phenylpyridazin-3(2H)-one;
4-phenyl-2-(4-(1,2,4,5-tetrahydro-3H-benzo[d]azepin-3-yl)butyl)pyridazin-3(2H)-one;
2-(4-(adamantan-1-ylamino)butyl)-4-phenylpyridazin-3(2H)-one;
2-(4-(benzyl((tetrahydrofuran-2-yl)methyl)amino)butyl)-4-phenylpyridazin-3(2H)-one;
2-(4-((2-methoxy-1-phenylethyl)(methyl)amino)butyl)-4-phenylpyridazin-3(2H)-one;
2-(4-(methyl((tetrahydro-2H-pyran-4-yl)methyl)amino)butyl)-4-phenylpyridazin-3(2H)-one;
4-phenyl-2-(4-(3-phenylpiperidin-1-yl)butyl)pyridazin-3(2H)-one;
4-phenyl-2-(4-(4-phenylpiperidin-1-yl)butyl)pyridazin-3(2H)-one;
2-(4-(2,6-dimethylmorpholino)butyl)-4-phenylpyridazin-3(2H)-one;
4-phenyl-2-(4-(2-phenylmorpholino)butyl)pyridazin-3(2H)-one;

2-[4-(4-benzylpiperazin-1-yl)butyl]-4-phenyl-2,3-dihydropyridazin-3-one;

2-[4-(4-benzylpiperidin-1-yl)butyl]-4-phenyl-2,3-dihydropyridazin-3-one;

2-{4-[benzyl(ethyl)amino]butyl}-4-phenyl-2,3-dihydropyridazin-3-one;

2-[4-(morpholin-4-yl)butyl]-4-(thiophen-3-yl)-2,3-dihydropyridazin-3-one;

4-phenyl-2-[4-(thiomorpholin-4-yl)butyl]-2,3-dihydropyridazin-3-one;

2-{4-[benzyl(methyl)amino]butyl}-6-methyl-4-phenyl-2,3-dihydropyridazin-3-one;

2-[4-(azepan-1-yl)butyl]-6-methyl-4-phenyl-2,3-dihydropyridazin-3-one; and 2-(4-morpholinobutyl)-4-(piperidin-1-yl)pyridazin-3(2H)-one (25a).

12. The compound according to claim 11, wherein said compound is selected from the group consisting of:

2-(3-(benzyl(methyl)amino)propyl)-4-phenylpyridazin-3(2H)-one;

2-(4-(benzyl(methyl)amino)butyl)-4-phenylpyridazin-3(2H)-one;

2-(4-(azocan-1-yl)butyl)-4-phenylpyridazin-3(2H)-one;

2-(4-(3,4-dihydroisoquinolin-2(1H)-yl)butyl)-4-phenylpyridazin-3(2H)-one;

4-phenyl-2-(4-(1,2,4,5-tetrahydro-3H-benzo[d]azepin-3-yl)butyl)pyridazin-3(2H)-one;

4-phenyl-2-(4-(3-phenylpiperidin-1-yl)butyl)pyridazin-3(2H)-one;

4-phenyl-2-(4-(4-phenylpiperidin-1-yl)butyl)pyridazin-3(2H)-one;

2-[4-(4-benzylpiperazin-1-yl)butyl]-4-phenyl-2,3-dihydropyridazin-3-one;

2-[4-(4-benzylpiperidin-1-yl)butyl]-4-phenyl-2,3-dihydropyridazin-3-one;

2-{4-[benzyl(ethyl)amino]butyl}-4-phenyl-2,3-dihydropyridazin-3-one;

4-phenyl-2-[4-(thiomorpholin-4-yl)butyl]-2,3-dihydropyridazin-3-one;

2-{4-[benzyl(methyl)amino]butyl}-6-methyl-4-phenyl-2,3-dihydropyridazin-3-one;

2-[4-(azepan-1-yl)butyl]-6-methyl-4-phenyl-2,3-dihydropyridazin-3-one; and, 2-(4-morpholinobutyl)-4-(piperidin-1-yl)pyridazin-3(2H)-one.

13. A pharmaceutical composition comprising an effective amount of a compound according to claim 1 and a pharmaceutically acceptable support.

14. A method of treating a disorder modulated by sigma-1 receptor comprising the administration of a therapeutically effective amount of a compound according to claim 1 or a pharmaceutical composition comprising said compound, to a subject in need of treatment, said disorder being selected from the group consisting of Alzheimer disease, Amyotrophic lateral sclerosis, and schizophrenia-related cognitive deficits.

* * * * *